(12) United States Patent
Schmidt et al.

(10) Patent No.: US 10,258,628 B2
(45) Date of Patent: Apr. 16, 2019

(54) GENERATION OF MUSCLE LINEAGE CELLS AND THERAPEUTIC USES THEREOF

(71) Applicant: Genea IP Holdings Pty Ltd, Sydney (AU)

(72) Inventors: Uli Schmidt, San Diego, CA (US); Anabel De La Garza, San Diego, CA (US); Alexander Kiselyov, San Diego, CA (US)

(73) Assignee: GENEA BIOCELLS USA (HOLDINGS), INC., San Diego, CA (US)

( * ) Notice: Subject to any disclaimer, the term of this patent is extended or adjusted under 35 U.S.C. 154(b) by 0 days.

(21) Appl. No.: 15/987,321

(22) Filed: May 23, 2018

(65) Prior Publication Data

US 2018/0263995 A1 Sep. 20, 2018

Related U.S. Application Data

(63) Continuation of application No. PCT/AU2017/051177, filed on Oct. 26, 2017.

(60) Provisional application No. 62/413,416, filed on Oct. 26, 2016.

(51) Int. Cl.
| | |
|---|---|
| *A61K 35/34* | (2015.01) |
| *A61K 45/06* | (2006.01) |
| *A61P 21/06* | (2006.01) |
| *C12N 5/077* | (2010.01) |
| *A61K 31/5377* | (2006.01) |

(52) U.S. Cl.
CPC .......... *A61K 31/5377* (2013.01); *A61K 35/34* (2013.01); *A61K 45/06* (2013.01); *A61P 21/06* (2018.01); *C12N 5/0658* (2013.01); *C12N 2501/727* (2013.01)

(58) Field of Classification Search
None
See application file for complete search history.

(56) References Cited

U.S. PATENT DOCUMENTS

| | | | |
|---|---|---|---|
| 5,143,842 | A | 9/1992 | Ham et al. |
| 5,998,209 | A | 12/1999 | Jokobovits et al. |
| 6,184,035 | B1 | 2/2001 | Csete et al. |
| 6,432,711 | B1 | 8/2002 | Dinsmore et al. |
| 8,900,572 | B2 | 12/2014 | Tremblay et al. |
| 2002/0164313 | A1 | 11/2002 | Tremblay |
| 2005/0054012 | A1 | 3/2005 | Tupler et al. |
| 2008/0206863 | A1 | 8/2008 | Dinsmore et al. |
| 2012/0141441 | A1 | 6/2012 | Calos et al. |
| 2012/0164731 | A1 | 6/2012 | Sakurai et al. |
| 2013/0040387 | A1 | 2/2013 | Heike et al. |
| 2013/0085139 | A1 | 4/2013 | Dickson et al. |
| 2013/0336935 | A1 | 12/2013 | Niedernhofer et al. |
| 2014/0080838 | A1 | 3/2014 | Wendel et al. |
| 2014/0287495 | A1 | 9/2014 | Mummery |
| 2014/0370537 | A1 | 12/2014 | Sakurai et al. |
| 2014/0377258 | A1 | 12/2014 | Stern et al. |
| 2014/0378470 | A1 | 12/2014 | Creasy et al. |
| 2015/0087636 | A1 | 3/2015 | Sverdrup et al. |
| 2015/0099747 | A1 | 4/2015 | Ma et al. |
| 2015/0111874 | A1 | 4/2015 | Castro et al. |
| 2015/0160246 | A1 | 6/2015 | Idelevich et al. |
| 2015/0225410 | A1 | 8/2015 | Castro et al. |
| 2015/0258175 | A1 | 9/2015 | Yu et al. |
| 2015/0283142 | A1 | 10/2015 | Stern et al. |
| 2015/0290207 | A1 | 10/2015 | Kutok et al. |
| 2015/0320754 | A1 | 11/2015 | Kutok et al. |
| 2015/0320779 | A1 | 11/2015 | Fillmore et al. |
| 2016/0022684 | A1 | 1/2016 | Kuo et al. |
| 2016/0024051 | A1 | 1/2016 | Genov et al. |
| 2016/0068834 | A1 | 3/2016 | Walensky |
| 2016/0113932 | A1 | 4/2016 | Stern et al. |
| 2016/0122365 | A1 | 5/2016 | Castro et al. |
| 2016/0160213 | A1 | 6/2016 | Classon et al. |

(Continued)

FOREIGN PATENT DOCUMENTS

| | | |
|---|---|---|
| AU | 2014268197 A1 | 8/2015 |
| EP | 2446886 A1 | 5/2012 |

(Continued)

OTHER PUBLICATIONS

Amsbio. Skeletal Muscle Differentiation Kit #SKM-KIT. Data sheet as captured by internet archive on May 9, 2016. 5 pages. URL:< https://web.archive.org/web/20160509153004/http://www.amsbio.com:80/datasheets/SKM-KIT.pdf.

Balog et al. Increased DUX4 expression during muscle differentiation correlates with decreased SMCHD1 protein levels at D4Z4. Epigenetics 10(12):1133-1142 (2015).

Bendall et al. IGF and FGF cooperatively establish the regulatory stem cell niche of pluripotent human cells in vitro. Nature 448(7157):1015-1021 (2007).

Borchin, et al. Derivation and FACS-mediated purification of PAX3+/PAX7+ skeletal muscle precursors from human pluripotent stem cells. Stem Cell Reports. Nov. 27, 2013;1(6):620-31. doi: 10.1016/j.stemcr.2013.10.007. eCollection 2013.

(Continued)

*Primary Examiner* — Blaine Lankford
(74) *Attorney, Agent, or Firm* — Wilson, Sonsini, Goodrich & Rosati

(57) ABSTRACT

Methods and compositions for producing mature myotubes are provided herein. In some instances, the method involves contacting a myoblast in an in vitro culture with a compound, wherein the contacting the myoblast in the in vitro culture with the compound results in generation of mature myotubes or myotube-like cells. In some cases, methods of treatment are provided involving treating a subject with a compound such as a Chk1 inhibitor in order to treat muscle deficiency. The compound may be administered as a stand-alone therapy or in combination with a cell therapy, such as introduction of muscle precursor cells such as satellite cells or myoblasts. Methods for identifying compounds that induce formation of mature myotubes or myotube-like cells from myoblasts are also provided herein, as well as methods of using the identified compounds to treat subjects.

24 Claims, 34 Drawing Sheets

(56) References Cited

U.S. PATENT DOCUMENTS

| | | |
|---|---|---|
| 2016/0194718 A1 | 7/2016 | Lane et al. |
| 2016/0222016 A1 | 8/2016 | Castro et al. |
| 2016/0244452 A1 | 8/2016 | Castro et al. |
| 2016/0305933 A1 | 10/2016 | Shigemoto et al. |
| 2016/0326596 A1 | 11/2016 | Levine et al. |
| 2016/0331750 A1 | 11/2016 | Wendel et al. |
| 2016/0340674 A1 | 11/2016 | Jin |
| 2016/0346293 A1 | 12/2016 | Keilhack |

FOREIGN PATENT DOCUMENTS

| | | |
|---|---|---|
| WO | WO-9817784 A1 | 4/1998 |
| WO | WO-2009068668 A1 | 6/2009 |
| WO | WO-2013116691 A1 | 8/2013 |
| WO | WO-2013120038 A2 | 8/2013 |
| WO | WO-2013138361 A1 | 9/2013 |
| WO | WO-2013138623 A1 | 9/2013 |
| WO | WO-2013155330 A1 | 10/2013 |
| WO | WO-2014062720 A2 | 4/2014 |
| WO | WO-2014071340 A1 | 5/2014 |
| WO | WO-2014100080 A1 | 6/2014 |
| WO | WO-2015120372 A2 | 8/2015 |
| WO | WO-2015124763 A1 | 8/2015 |
| WO | WO-2016073956 A1 | 5/2016 |
| WO | WO-2016108288 A1 | 7/2016 |
| WO | WO-2016168890 A1 | 10/2016 |
| WO | WO-2017201585 A1 | 11/2017 |
| WO | WO-2018076060 A1 | 5/2018 |

OTHER PUBLICATIONS

Bosnakovski et al. High-throughput screening identifies inhibitors of DUX4-induced myoblast toxicity. Skeletal Muscle 4:4 (2014).

Caron, et al. A Human Pluripotent Stem Cell Model of Facioscapulohumeral Muscular Dystrophy-Affected Skeletal Muscles. Stem Cells Transl Med. Sep. 2016;5(9):1145-61. Epub May 23, 2016. doi: 10.5966/sctm.2015-0224.

Chal, et al. Differentiation of pluripotent stem cells to muscle fiber to model Duchenne muscular dystrophy. Nat Biotechnol. Sep. 2015;33(9):962-9. doi: 10.1038/nbt.3297. Epub Aug. 3, 2015.

Choi, et al. A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015. Co-pending U.S. Appl. No. 15/568,274, filed Oct. 20, 2017.

Hosoyama, et al. Derivation of myogenic progenitors directly from human pluripotent stem cells using a sphere-based culture. Stem Cells Transl Med. May 2014;3(5):564-74. doi:10.5966/sctm.2013-0143. Epub Mar. 21, 2014.

Huichalaf, et al. DNA Methylation Analysis of the Macrosatellite Repeat Associated with FSHD Muscular Dystrophy at Single Nucleotide Level. PLoS One. 2014; 9(12): e115278. Published online Dec. 29, 2014. DOI: 10.1371/journal.pone.0115278.

Hwang, et al. Directed in vitro myogenesis of human embryonic stem cells and their in vivo engraftment. PLoS One. Aug. 19, 2013;8(8):e72023. doi: 10.1371/journal.pone.0072023. eCollection 2013.

International Preliminary Report on Patentability dated Nov. 2, 2017 for International PCT Patent Application No. PCT/AU2016/000144.

International Search Report and Written Opinion dated Jul. 25, 2016 for International PCT Patent Application No. PCT/AU2016/000144.

International Search Report and Written Opinion dated Aug. 15, 2017 for International PCT Patent Application No. PCT/AU2017/050498.

Kissell et al. Pilot trial of albuterol in facioscapulohumeral muscular dystrophy. Neurology. May 1998, 50 (5) 1402-1406.

Krause et al. Activation of nicotinic acetylcholine receptors increases the rate of fusion of cultured human myoblasts. J Physiol. Dec. 15, 1995; 489(Pt 3): 779-790.

Lan et al. Reconstitution of a functional human immune system in immunodeficient mice through combined human fetal thymus/liver and CD34+ cell transplantation. Blood 108(2):487-492 (2006).

Lee, et al. Identification of Small Molecules Which Induce Skeletal Muscle Differentiation in Embryonic Stem Cells via Activation of the Wnt and Inhibition of Smad2/3 and Sonic Hedgehog Pathways. Stem Cells. Feb. 2016;34(2):299-310. doi: 10.1002/stem.2228. Epub Nov. 17, 2015.

Mahmood, et al. Enhanced differentiation of human embryonic stem cells to mesenchymal progenitors by inhibition of TGF-beta/activin/nodal signaling using SB-431542. J Bone Miner Res. Jun. 2010;25(6):1216-33. doi: 10.1002/jbmr.34.

Marg, et al. New Research Method Opens Door to Therapy with Human Muscle Stem Cells. https://www.mdc-berlin.de/43612981/en/news/2014/20140827-new_research_method_opens_door_to_therapy_. Accessed on Dec. 3, 2015. 3 pages.

Muscular Dystrophy Canada. Facioscapulohumeral Dystrophy (FSHD). Sep. 2007. 4 pages. URL:< http://muscle.ca/wp-content/uploads/2012/11/fshd_factsheet_en.pdf.

Neguembor et al. FSHD muscular dystrophy region gene 1 binds Suv4-20h1 histone methyltransferase and impairs myogenesis. Journal of molecular cell biology 5.5 (2013): 294-307.

PCT/AU2017/050498 International Search Report and Written Opinion dated Aug. 15, 2017.

PCT/AU2017/051177 International Search Report and Written Opinion dated Feb. 15, 2018.

Sebastian, et al. Extended 2D myotube culture recapitulates postnatal fibre type plasticity. BMC Cell Biology. 2015; 16: 23. Published online: Sep. 17, 2015. doi: 10.1186/s12860-015-0069-1.

Shelton, et al. Derivation and expansion of PAX7-positive muscle progenitors from human and mouse embryonic stem cells. Stem Cell Reports. Sep. 9, 2014;3(3):516-29. doi: 10.1016/j.stemcr.2014.07.001. Epub Aug. 7, 2014.

Shelton, et al. Robust generation and expansion of skeletal muscle progenitors and myocytes from human pluripotent stem cells. Methods. May 15, 2016;101:73-84. doi:10.1016/j.ymeth.2015.09.019. Epub Sep. 25, 2015.

Balog et al. Correlation analysis of clinical parameters with epigenetic modifications in the DUX4 promoter in FSHD. Epigenetics. Jun. 1, 2012;7(6):579-84.

Bao et al. Potential of antisense therapy for facioscapulohumeral muscular dystrophy. Expert Opinion on Orphan Drugs 3.12 (2015): 1365-1374.

Bortolanza et al. AAV6-mediated systemic shRNA delivery reverses disease in a mouse model of facioscapulohumeral muscular dystrophy. Molecular Therapy19.11 (2011): 2055-2064.

Bosnakovski et al. High-throughput screening identifies inhibitors of DUX4-induced myoblast toxicity.Skeletal muscle 4.1 (2014): 4.

Choi et al. DUX4 recruits p300/CBP through its C-terminus and induces global H3K27 acetylation changes. Nucleic acids research 44.11 (2016): 5161-5173.

Daxinger et al. Genetic and epigenetic contributors to FSHD. Current opinion in genetics & development 33 (2015): 56-61.

Dib et al. Correction of the FSHD myoblast differentiation defect by fusion with healthy myoblasts. Journal of cellular physiology 231.1 (2016): 62-71.

Feng et al. A feedback loop between nonsense-mediated decay and the retrogene DUX4 in facioscapulohumeral muscular dystrophy. Elife 4 (2015).

Hartweck et al. A focal domain of extreme demethylation within D4Z4 in FSHD2. Neurology 80.4 (2013): 392-399.

Himeda et al. CRISPR/dCas9-mediated transcriptional inhibition ameliorates the epigenetic dysregulation at D4Z4 and represses DUX4-fl in FSH muscular dystrophy. Molecular Therapy 24.3 (2016): 527-535.

Himeda et al. Facioscapulohumeral muscular dystrophy as a model for epigenetic regulation and disease. Antioxidants & redox signaling 22.16 (2015): 1463-1482.

Himeda et al. Myogenic enhancers regulate expression of the facioscapulohumeral muscular dystrophy-associated DUX4 gene. Molecular and cellular biology 34.11 (2014): 1942-1955.

(56) References Cited

OTHER PUBLICATIONS

Huichalaf et al. DNA methylation analysis of the macrosatellite repeat associated with FSHD muscular dystrophy at single nucleotide level. PLoS One 9.12 (2014): e115278.

Jones et al. Identifying diagnostic DNA methylation profiles for facioscapulohumeral muscular dystrophy in blood and saliva using bisulfite sequencing. Clinical epigenetics 6.1 (2014): 23.

Krom et al. Generation of isogenic D4Z4 contracted and noncontracted immortal muscle cell clones from a mosaic patient: a cellular model for FSHD. The American journal of pathology 181.4 (2012): 1387-1401.

Lefkowitz et al. Fascioscapulohumeral muscular dystrophy: a progressive degenerative disease that responds to diltiazem. Medical hypotheses 65.4 (2005): 716-721.

Lemmers et al. Digenic inheritance of an SMCHD1 mutation and an FSHD-permissive D4Z4 allele causes facioscapulohumeral muscular dystrophy type 2. Nature genetics 44.12 (2012): 1370.

Lemmers et al. Inter-individual differences in CpG methylation at D4Z4 correlate with clinical variability in FSHD1 and FSHD2. Human molecular genetics 24.3 (2014): 659-669.

Lim et al. DICER/AGO-dependent epigenetic silencing of D4Z4 repeats enhanced by exogenous siRNA suggests mechanisms and therapies for FSHD. Human molecular genetics 24.17 (2015): 4817-4828.

Morosetti et al. Isolation and characterization of mesoangioblasts from facioscapulohumeral muscular dystrophy muscle biopsies. Stem Cells 25.12 (2007): 3173-3182.

Passerieux et al. Effects of vitamin C, vitamin E, zinc gluconate, and selenomethionine supplementation on muscle function and oxidative stress biomarkers in patients with facioscapulohumeral dystrophy: a double-blind randomized controlled clinical trial. Free Radical Biology and Medicine 81 (2015): 158-169.

Sacconi et al. Facioscapulohumeral muscular dystrophy. Biochimica et Biophysica Acta (BBA)-Molecular Basis of Disease 1852.4 (2015): 607-614.

Tawil et al. Facioscapulohumeral dystrophy: the path to consensus on pathophysiology. Skeletal muscle 4.1 (2014): 12.

Van Den Boogaard et al. Mutations in DNMT3B modify epigenetic repression of the D4Z4 repeat and the penetrance of facioscapulohumeral dystrophy. The American Journal of Human Genetics 98.5 (2016): 1020-1029.

Wallace et al. RNA interference inhibits DUX4-induced muscle toxicity in vivo: implications for a targeted FSHD therapy. Molecular Therapy 20.7 (2012): 1417-1423.

Young et al. DUX4 binding to retroelements creates promoters that are active in FSHD muscle and testis. PLoS genetics 9.11 (2013): e1003947.

Zeng et al. Specific loss of histone H3 lysine 9 trimethylation and HP1γ/cohesin binding at D4Z4 repeats is associated with facioscapulohumeral dystrophy (FSHD). PLoS genetics 5.7 (2009): e1000559.

Tawil et al. A pilot trial of prednisone in facioscapulohumeral muscular dystrophy. FSH-DY Group. Neurology. Jan. 1997;48(1):46-9.

The Muscular Dystrophy Association. Facioscapulohumeral Muscular Dystrophy (FSH, FSHD). Muscular Dystrophy Association Inc. ©2018. 5 pages. URL:< https://www.mda.org/disease/facioscapulohumeral-muscular-dystrophy>.

Tidy et al. Facioscapulohumeral Muscular Dystrophy. Apr. 15, 2016. Patient: Orthopaedics and Sports Medicine. 7 pages. URL:< https://patient.info/doctor/facioscapulohumeral-muscular-dystrophy>.

Zeng et al. Genetic and Epigenetic Characteristics of FSHD-Associated 4q and 10q D4Z4 that are Distinct from Non-4q/10q D4Z4 Homologs. Human Mutation 35(8):998-1010 (2014).

BEZ235

Omipalisib

LY2228820

AZD8055

BI-D1879

Danusertib

GENERATION OF MUSCLE LINEAGE CELLS AND THERAPEUTIC USES THEREOF

RELATED APPLICATIONS

This application claims the benefit of U.S. Provisional Application No. 62/413,416, filed Oct. 26, 2016, and PCT Application No. PCT/AU2017/051177, filed Oct. 26, 2017, each of which is incorporated by reference herein in its entirety.

BACKGROUND

During healthy muscle development, myoblasts (generally, primordial muscle cells) may proliferate and/or differentiate and then fuse to form multi-nucleated fibers called myotubes. Mature or adult-like myotubes are generally highly multinucleated and are relatively thick and long, particularly when compared to immature myotubes. Mature myotubes also may form branched structures and typically have a central core occupied by nuclei and sarcoplasm, which may give the cells a tubular appearance. Interestingly, mature myotubes in vivo tend to be highly adaptable in response to changes in physiological demands or in response to disease and are able to undergo phenotypic changes in size (hypertrophy or atrophy) and in metabolic capacity (e.g., ranging from relying on highly oxidative pathways to highly glycolytic pathways).

Muscle fibers in vivo may also appear as slow-twitch or fast-twitch forms. Slow-twitch fibers tend to rely on aerobic respiration (glycolysis and Krebs cycle) to fuel muscle contraction and are ideal for long-term endurance (e.g., long-distance running) and for postural support. Slow-twitch fibers generally have relatively high oxygen requirements and generally have high numbers of mitochondria and high concentrations of myoglobin, an oxygen-binding protein found in the blood that gives muscles their reddish color. In contrast, fast-twitch fibers tend to rely on anaerobic respiration (glycolysis alone) to fuel muscle contraction and are ideal for quick contractions of short duration and are useful for rapid bursts of movement.

Muscular diseases and disorders, both developmental and degenerative, can cause the gradual or sudden loss of muscular function due to the decline or death of muscle cells, as well as lessened muscular development due to developmental diseases. Congenital myopathies are examples of muscular diseases that present these characteristics. Muscle loss may also occur from aging, from the treatment of diseases, or from a number of other causes. Examples of these types of muscle loss include sarcopenia and cachexia. There is a need in the art for therapies for the various types of muscle loss.

SUMMARY

In some aspects, the present disclosure provides a method of generating mature myotubes, the method comprising: (a) providing one or more myoblasts, wherein the myoblasts are derived from a human; and (b) culturing the one or more myoblasts in vitro in a culture comprising a medium having one or more compounds specifically selected to encourage mature myotube production, thereby producing mature myotubes exhibiting two or more of the following features: (i) greater than 15 nuclei per myotube; (ii) a length greater than 0.5 mm; (iii) a diameter larger than 6 µm; and (iv) a myotube area greater than 3,000 µm². In some embodiments, the method further comprises incubating the one or more myoblasts in the medium comprising one or more compounds specifically selected to encourage mature myotube production for at least 12 hours. In some embodiments, the method further comprises detecting the mature myotubes in the culture. In some embodiments, the mature myotubes exhibit greater than 15 nuclei per cell. In some embodiments, the mature myotubes exhibit greater than 20 nuclei per cell. In some embodiments, the mature myotubes exhibit greater than 30 nuclei per cell. In some embodiments, the mature myotubes exhibit greater than 50 nuclei per cell. In some embodiments, the mature myotubes exhibit a myotube area greater than 4,000 µm². In some embodiments, the mature myotubes exhibit a myotube area greater than 5,000 µm². In some embodiments, the culture contains myotubes with a mean myotube area greater than 1,000 µm². In some embodiments, the culture contains myotubes with a mean myotube area greater than 1,500 µm². In some embodiments, the culture contains myotubes with a mean myotube area greater than 2,000 µm². In some embodiments, the mature myotubes exhibit a diameter greater than 6 µm. In some embodiments, the mature myotubes exhibit a diameter greater than 10 µm. In some embodiments, the mature myotubes exhibit a diameter greater than 12 µm. In some embodiments, the mature myotubes exhibit a diameter larger than 14 µm. In some embodiments, the one or more compounds specifically selected to encourage mature myotube production comprise one or more compounds targeting one or more of the following pathways: cell cycle signaling pathways, DNA repair pathways, MAPK signaling pathways, RTK/PI3K/Akt signaling pathways, mTOR signaling pathways, G-protein coupled receptor (GPCR) pathways, and muscarinic acetylcholine receptor (mAChR) pathways. In some embodiments, the one or more compounds comprise a compound of Formula (I):

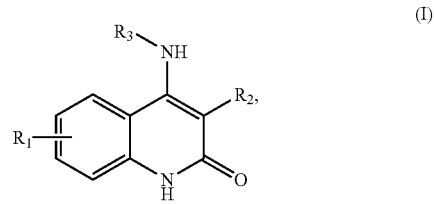

or a salt thereof, wherein R1 is selected from methyl, fluoro, chloro, trifluoromethyl, and difluoromethyl; R2 is selected from benzimidazolyl, benzoxazolyl, benzothiazolyl, 3H-indolyl, benzofuryl, benzothiophenyl, and 1H-indenyl; and R3 is selected from quinuclidinyl and 1,4-diazabicyclo[2.2.2]octanyl. In some embodiments, the one or more compounds comprise a compound of Formula (II):

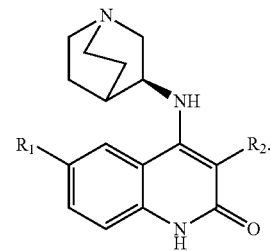

or a salt thereof, wherein R1 is selected from methyl, halogen, and halomethyl; and R2 is a 5+6 bicyclic fused ring system containing 0-4 heteroatoms independently selected from O, S or N. In some embodiments, the one or more compounds comprise a compound of Formula (III):

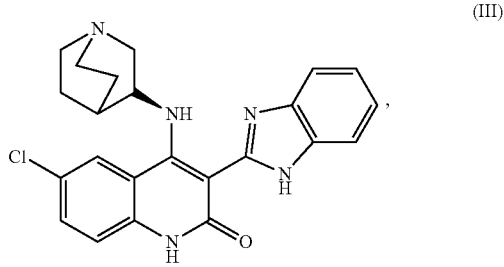

or a salt thereof. In some embodiments, the mature myotubes exhibiting the two or more features make up at least 50% of a culture in the absence of purification or selection for mature myotubes. In some embodiments, the mature myotubes exhibiting the two or more features make up at least 70% of a culture in the absence of purification or selection for mature myotubes In some embodiments, the mature myotubes exhibiting the two or more features make up at least 60% of the culture in the absence of purification or selection for mature myotubes and exhibit a diameter greater than 10 μm. In some embodiments, the mature myotubes exhibiting the two or more features make up at least 60% of the culture in the absence of purification or selection for mature myotubes and exhibit a diameter greater than 12 μm. In some embodiments, the mature myotubes exhibiting the two or more features make up at least 60% of the culture in the absence of purification or selection for mature myotubes and comprise at least 20 nuclei per myotube. In some embodiments, the one or more compounds specifically selected to encourage mature myotube production comprise one or more Chk1 inhibitors. In some embodiments, the one or more Chk1 inhibitors comprise CHIR-124. In some embodiments, the one or more compounds specifically selected to encourage mature myotube production are selected from the group consisting of: mTOR inhibitor, MEK inhibitor, Raf inhibitor, GPR119 agonist, poly ADP-ribose polymerase (PARP) inhibitor, S1P1 agonist, and mAChR agonist. In some embodiments, the one or more compounds specifically selected to encourage mature myotube production are selected from the group consisting of: rapamycin, MEK162, sorafenib, GSK1292263, TC-G 1006, pilocarpine, atropine, and talazoparib. In some embodiments, the one or more myoblasts are primary myoblasts. In some embodiments, the one or more compounds comprise pilocarbine. In some embodiments, the one or more myoblasts are generated by differentiating satellite cells in vitro. In some embodiments, the mature myotubes are mature myotube-like cells. In some embodiments, the satellite cells are generated by differentiating pluripotent stem cells in vitro. In some embodiments, the method further comprises contacting satellite cells with a compound to generate the one or more myoblasts. In some embodiments, the method further comprises contacting pluripotent stem cells with one or more compounds to generate the satellite cells. In some embodiments, the mature myotubes are generated less than 30 days from the contacting the pluripotent stem cells with the one or more compounds to generate the satellite cells. In some embodiments, the mature myotubes are generated within 25 days from the contacting the pluripotent stem cells with the one or more compounds to generate the satellite cells. In some embodiments, the mature myotubes are generated less than 30 days from the contacting the pluripotent stem cells with the one or more compounds to generate the satellite cells and wherein the mature myotubes are generated at a rate of at least five mature myotubes per pluripotent stem cell. In some embodiments, the mature myotubes are generated less than 30 days from the contacting the pluripotent stem cells with the one or more compounds to generate the satellite cells and wherein the mature myotubes are generated at a rate of at least 50 mature myotubes per pluripotent stem cell. In some embodiments, the mature myotube-like cells comprise a greater than 25%, 50%, or 100% level of fast MHC when compared to myotube cells generate in the absence of the one or more compounds.

In some aspects, the present disclosure provides for a composition produced by any one of the preceding methods. In some embodiments, the composition is a cell culture. In some embodiments, the composition comprises isolated or purified cells.

In some aspects, the present disclosure provides for a composition comprising one or more mature myotube-like cells derived from human cells, wherein the one or more mature myotube-like cells exhibit two or more of the following features: (i) greater than 15 nuclei per mature myotube-like cell; (ii) a length greater than 0.5 mm; (iii) a diameter larger than 6 μm and (iv) a myotube area greater than 3,000 μm$^2$. In some embodiments, the composition comprises myotubes with a mean myotube area greater than 1,000 μm$^2$. In some embodiments, the composition comprises myotubes with a mean myotube area greater than 2,000 μm$^2$. In some embodiments, the one or more mature myotube-like cells exhibit a myotube area greater than 3,000 μm$^2$. In another embodiment, the one or more mature myotube-like cells exhibit a myotube area greater than 4,000 μm$^2$. In some embodiments, the one or more mature myotube-like cells exhibit a myotube area greater than 5,000 μm$^2$. In some embodiments, the one or more myotube-like cells exhibit greater than 30 nuclei per cell. In some embodiments, the one or more mature myotube-like cells exhibit a diameter greater than 6 μm. In some embodiments, the one or more mature myotube-like cells exhibit a diameter greater than 10 μm. In some embodiments, the one or more mature myotube-like cells exhibit a diameter greater than 12 μm. In some embodiments, the one or more mature myotube-like cells exhibit a diameter greater than 14 μm. In some embodiments, the one or more mature myotube-like cells are generated by differentiating one or more myoblasts in vitro. In some embodiments, the one or more mature myotube-like cells are MyHC$^+$, MYOG$^+$, or both. In some embodiments, the one or more mature myotube-like cells comprise striated fibers. In some embodiments, the one or more mature myotube-like cells are capable of spontaneous twitching.

In further aspects, the present disclosure provides a method of treating a subject with a muscular deficiency (or promoting mature myotube generation in a subject with a muscular deficiency) comprising: treating the subject with one or more compounds capable of promoting mature myotube generation in the subject, thereby treating the subject with muscular deficiency. In some embodiments, the method further comprises, administering to the subject a plurality of cells selected from the group consisting of: pluripotent stem cells, satellite cells, myoblasts, satellite-like cells, myoblast-like cells, and any combination thereof. In some aspects, the present disclosure provides for a method of treating a subject with muscular deficiency comprising: (a) obtaining mature myotubes produced by any one of the methods described herein; and (b) introducing the mature myotubes into the subject with the muscular deficiency.

In some embodiments of any of the methods of treating provided herein (or of the methods of promoting mature myotube production in a subject), the method further comprises administering one or more compounds to the subject. In some embodiments, the one or more compounds comprise a checkpoint inhibitor. In some embodiments, the checkpoint inhibitor is a Checkpoint kinase 1 (Chk1) inhibitor. In some embodiments, the Chk1 inhibitor is CHIR-124. In some embodiments, the one or more compounds comprise a compound of Formula (I):

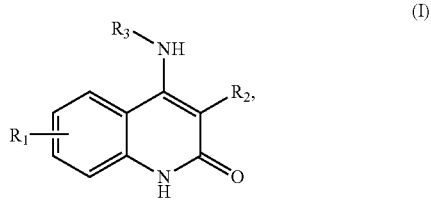

or a salt thereof, wherein R1 is selected from methyl, fluoro, chloro, trifluoromethyl, and difluoromethyl; R2 is selected from benzimidazolyl, benzoxazolyl, benzothiazolyl, 3H-indolyl, benzofuryl, benzothiophenyl, and 1H-indenyl; and R3 is selected from quinuclidinyl and 1,4-diazabicyclo[2.2.2]octanyl. In some embodiments, the one or more compounds comprise a compound of Formula (II):

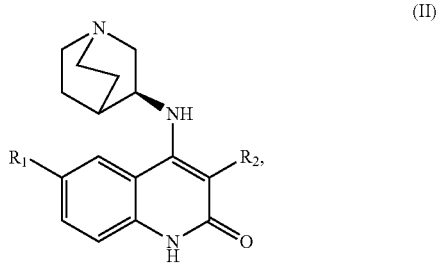

or a salt thereof, wherein R1 is selected from methyl, halogen, and halomethyl; and R2 is a 5+6 bicyclic fused ring system containing 0-4 heteroatoms independently selected from O, S or N. In another embodiment, the one or more compounds comprise a compound of Formula (III):

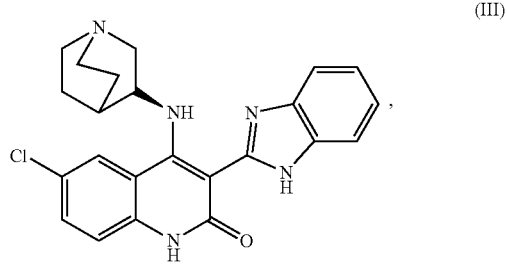

or a salt thereof. In some embodiments, the muscular deficiency is caused by muscular dystrophy. In some embodiments, the muscular deficiency is caused by Duchenne muscular dystrophy. In some embodiments, the muscular deficiency is caused by cachexia or sarcopenia. In some embodiments, the cells or the mature myotubes, where applicable, are implanted on a scaffold prior to the introduction to the subject with the muscular deficiency. In some embodiments, following the introduction of the cells or the mature myotubes to the subject with the muscular deficiency, the subject with the muscular deficiency does not mount a significant immune response against the cells. In some embodiments, the cells or the mature myotubes are derived from the subject with the muscular deficiency. In some embodiments, the one or more compounds comprise an immunosuppressant drug or an antibiotic. In some embodiments, the one or more compounds comprise at least one compound capable of differentiating myoblasts into mature myotubes in vivo. In some embodiments, the one or more compounds is at least one compound targeting one or more of the following pathways: cell cycle signaling pathways, DNA repair pathways, MAPK signaling pathways, PI3K/Akt signaling pathways, mTOR signaling pathways, G-protein coupled receptor (GPCR) pathways, and muscarinic acetylcholine receptor (mAChR) pathways. In some embodiments, the one or more compounds is selected from the group consisting of: mTOR inhibitor, MEK inhibitor, Raf inhibitor, GPR119 agonist, poly ADP-ribose polymerase (PARP) inhibitor, S1P1 agonist, and mAChR agonist. In some embodiments, the one or more compounds is selected from the group consisting of: rapamycin, MEK162, sorafenib, GSK1292263, TC-G 1006, pilocarpine, atropine, and talazoparib.

In some aspects of the invention, this disclosure provides methods of generating mature myotubes cells comprising: (a) providing one or more myoblasts, wherein the myoblasts are derived from a human; (b) culturing the one or more myoblasts in vitro in a medium comprising one or more compounds specifically selected to encourage mature myotube production; (c) incubating the one or more myoblasts in the medium comprising a compound specifically selected to encourage mature myotube production for at least 12 hours; and (d) detecting mature myotubes in the culture, wherein the mature myotubes exhibit two or more of the following features: (i) greater than 15 nuclei; (ii) a length greater than 0.5 mm; (iii) a diameter larger than 6 µm; and (iv) myotube area greater than 3,000 µm$^2$.

In some aspects of the invention, this disclosure provides methods of generating mature myotubes cells comprising: (a) providing one or more myoblasts, wherein the myoblasts are derived from a human; and (b) culturing the one or more myoblasts in vitro in a medium comprising one or more compounds specifically selected to encourage mature myotube production, thereby producing mature myotubes exhibiting two or more of the following features: (i) greater than 15 nuclei; (ii) a length greater than 0.5 mm; (iii) a diameter larger than 6 µm; and (iv) myotube area greater than 3,000 µm$^2$.

In some cases of the methods of any of the preceding, the one or more compounds specifically selected to encourage mature myotube production comprise one or more compounds targeting one or more of the following pathways: cell cycle signaling pathways, DNA repair pathways, MAPK signaling pathways, RTK/PI3K/Akt signaling pathways, mTOR signaling pathways, G-protein coupled receptor (GPCR) pathways, and muscarinic acetylcholine receptor (mAChR) pathways. In some cases of the methods of any of the preceding, the one or more compounds specifically selected to encourage mature myotube production comprise one or more Chk1 inhibitors. In some cases of the methods of any of the preceding, the one or more Chk1 inhibitors comprise CHIR-124. In some cases of the methods of any of the preceding, the one or more compounds specifically selected to encourage mature myotube production are selected from the group consisting of: mTOR inhibitor, MEK inhibitor, Raf inhibitor, GPR119 agonist, poly ADP-ribose polymerase (PARP) inhibitor, S1P1 agonist, and mAChR agonist. In some cases of the methods of any of the preceding, the one or more myoblasts are primary myoblasts. In some cases of the methods of any of the preceding, the one or more myoblasts are generated by differentiating satellite cells in vitro. In some cases of the methods of any of the preceding, the mature myotubes are mature myotube-like cells. In some cases of the methods of any of the preceding, the satellite cells are generated by differentiating pluripotent stem cells in vitro. In some cases of the methods of any of the preceding, the methods further comprise contacting satellite cells with a compound to generate the one or more myoblasts provided in step a. In some cases of the methods of any of the preceding, the methods further comprise contacting pluripotent stem cells with one or more compounds to generate the satellite cells. In some cases of the methods of any of the preceding, the mature myotubes are generated less than 30 days from the contacting the pluripotent stem cells with the one or more compounds to generate the satellite cells. In some cases of the methods of any of the preceding, the mature myotubes are generated within 25 days from the contacting the pluripotent stem cells with the one or more compounds to generate the satellite cells. In some cases of the methods of any of the preceding, the mature myotubes are generated less than 30 days from the contacting the pluripotent stem cells with the one or more compounds to generate the satellite cells and wherein the mature myotubes are generated at a rate of at least five mature myotubes per pluripotent stem cell. In some cases of the methods of any of the preceding, the mature myotubes are generated less than 30 days from the contacting the pluripotent stem cells with the one or more compounds to generate the satellite cells and wherein the mature myotubes are generated at a rate of at least 50 mature myotubes per pluripotent stem cell.

In some aspects of the compositions provided herein, this disclosure provides compositions comprising one or more mature myotube-like cells, wherein the one or more mature myotube-like cells exhibit two or more of the following features: (i) greater than 15 nuclei; (ii) a length greater than 0.5 mm; (iii) a diameter larger than 6 µm and (iv) myotube area greater than 3,000 µm$^2$. In some cases of the compositions of any of the preceding, the one or more mature myotube-like cells are MyCH$^+$ and/or MYOG$^+$. In some cases of the compositions of any of the preceding, the one or more mature myotube-like cells comprise striated fibers. In some cases of the compositions of any of the preceding, the one or more mature myotube-like cells are capable of spontaneous twitching.

In some aspects of the methods provided herein, this disclosure provides methods of treating a subject with muscular deficiency comprising: (a) obtaining mature myotubes produced by any one of the methods of claims 1-15; and (b) introducing the cells into the subject with the muscular deficiency. In some cases of the methods of any of the preceding, the muscular deficiency is caused by muscular dystrophy. In some cases of the methods of any of the preceding, the muscular deficiency is caused by Duchenne muscular dystrophy. In some cases of the methods of any of the preceding, the muscular deficiency is caused by cachexia or sarcopenia. In some cases of the methods of any of the preceding, the mature myotubes are implanted on a scaffold prior to the introduction to the subject with the muscular deficiency. In some cases of the methods of any of the preceding, following the introduction of the mature myotubes to the subject with the muscular deficiency, the subject with the muscular deficiency does not mount a significant immune response against the cells. In some cases of the methods of any of the preceding, the mature myotubes are derived from the subject with the muscular deficiency. In some cases of the methods of any of the preceding, the methods further comprise administering a drug to the subject. In some cases of the methods of any of the preceding, the drug is an immunosuppressant drug or an antibiotic. In some cases of the methods of any of the preceding, the drug comprises at least one compound capable of differentiating myoblasts into mature myotubes in vivo. In some cases of the methods of any of the preceding, the at least one compound capable of differentiating myoblasts into mature myotubes in vivo is at least one compound targeting one or more of the following pathways: cell cycle signaling pathways, DNA repair pathways, MAPK signaling pathways, PI3K/Akt signaling pathways, mTOR signaling pathways, G-protein coupled receptor (GPCR) pathways, and muscarinic acetylcholine receptor (mAChR) pathways. In some cases of the methods of any of the preceding, the at least one compound capable of differentiating myoblasts into mature myotubes in vivo comprise one or more Chk1 inhibitors. In some cases of the methods of any of the preceding, the Chk1 inhibitor is CHIR-124. In some cases of the methods of any of the preceding, the at least one compound capable of differentiating myoblasts into mature myotubes in vivo is selected from the group consisting of: mTor inhibitor, MEK inhibitor, Raf inhibitor, GPR119 agonist, poly ADP-ribose polymerase (PARP) inhibitor, and S1P1 agonist, mAChR agonist. In some cases of the methods of any of the preceding, the two or more features exhibited by the mature myotubes comprise myotube area greater than 3,000 µm$^2$. In some cases of the methods of any of the preceding, the two or more features exhibited by the mature myotubes comprise myotube area greater than 4,000 µm$^2$. In some cases of the methods of any of the preceding, the two or more features exhibited by the mature myotubes comprise myotube area greater than 5,000 µm$^2$. In some cases of the methods of any of the preceding, the mature myotubes exhibiting the two or more features make up at least 50% of a culture in the absence of purification or selection for mature myotubes. In some cases of the methods of any of the preceding, the mature myotubes exhibiting the two or more features make up at least 70% of a culture in the absence of purification or selection for mature myotubes.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Overview

Figure 1:
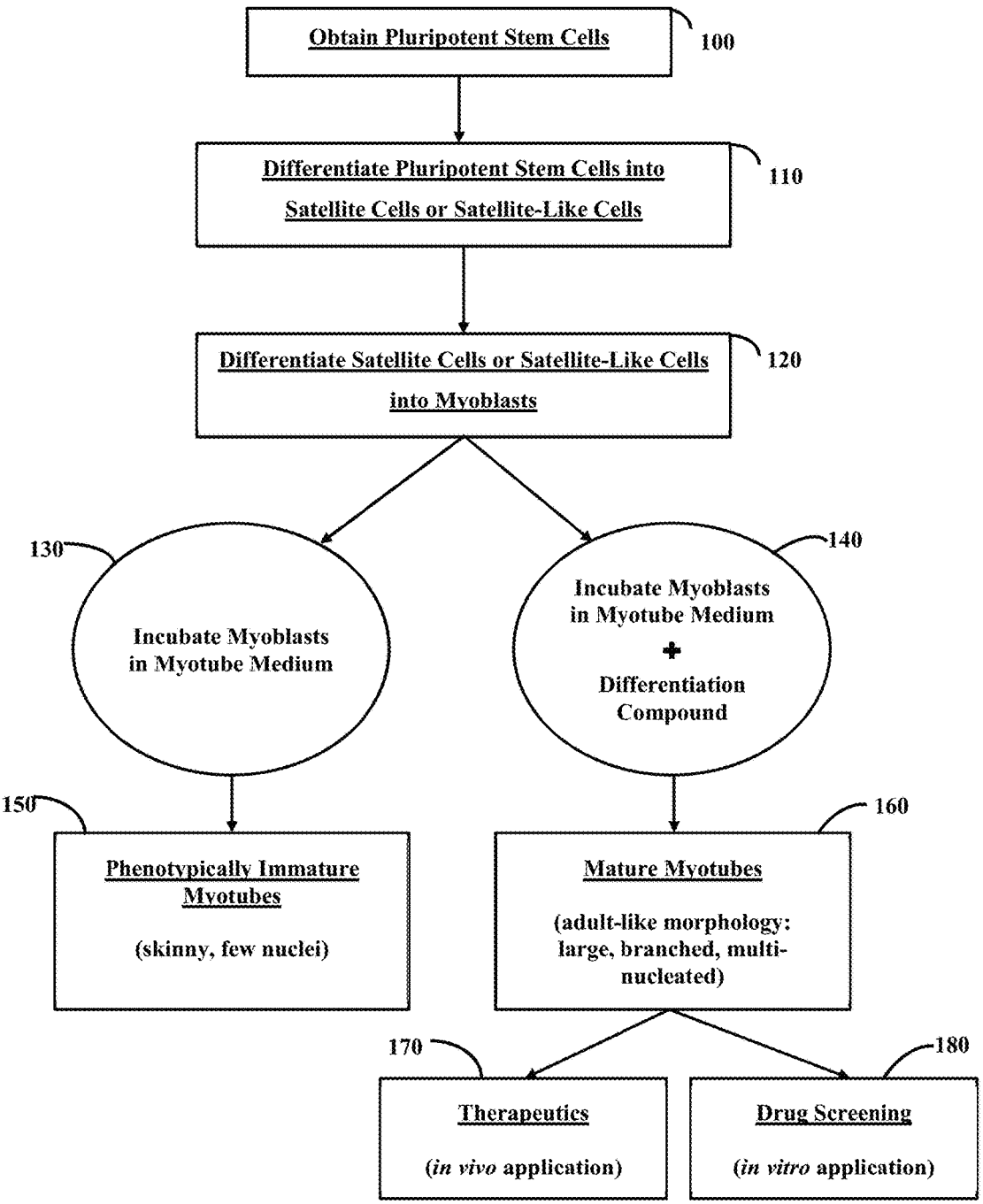
FIG. 1 is an overview depicting methods of generating mature myotubes in vitro and their uses.

The present disclosure features unique methods for generating mature myotubes, which are typically elongated, thick, multi-nucleated cells also known as skeletal muscle cells or muscle fibers. The methods generally involve contacting myoblasts with one or more compounds that cause the myoblasts to form mature myotubes, often by differentiation and/or proliferation of the myoblasts. The methods often involve a one-step process and therefore tend to be highly efficient. In some instances, the methods may comprise contacting myoblasts or myoblast-like cells (e.g., in vitro-generated myoblasts) with a differentiation medium that includes one or more differentiation compounds (e.g., a Chk1 inhibitor). Often, the one or more differentiation compounds are known signaling molecules—or target known signaling molecules—in a signaling network or pathway such as a cell-cycle signaling pathway, DNA repair pathway, receptor tyrosine kinase-mediated signaling pathway and/or G-protein coupled receptor-mediated signaling pathway, or combination thereof.

The methods provided herein tend to provide highly efficient approaches to producing mature myotubes. In some cases, the methods provided herein do not require labor-intensive manipulation such as genetic engineering or cell sorting. The methods may also be highly efficient in that they may involve use of myoblast cells, or myoblast-like cells, which are typically highly proliferative and can be expanded on a large scale by commonly used passaging methods. As a result, large numbers of myotubes may be generated with relative ease. The methods may further be highly efficient in that the total time to generate myotubes, or myotube-like cells, is often relatively short.

Clinically, the compounds described herein, as well as the mature myotubes or myotube-like cells generated by the methods herein may be extremely useful in a number of settings, including the treatment of patients such as patients with muscular degenerative diseases or muscular disorders stemming from a variety of causes, including but not limited to genetic disorders, sporadic diseases, cachexia, muscle strain, muscle injury, muscle atrophy and/or muscle wasting as exemplified by different forms of cachexia, as well as sarcopenia and the general aging process. Myotube precursor cells, or the mature myotubes or myotube-like cells provided herein, may be used in cell therapies for such patients, particularly therapies to replenish or supplement a patient's naturally-occurring skeletal muscle cells. In some cases, the therapies may involve administering a compound provided herein as a stand-alone therapy to promote the treatment of a muscle deficiency.

In some cases, the methods herein involve combining a cell therapy with a drug therapy. For example, myotube precursor cells (e.g., pluripotent cells, satellite cells, myoblast cells) or mature myotubes may be transplanted into a subject; and the subject may be administered a compound provided herein (e.g., checkpoint inhibitor, Chk1 inhibitor, CHIR-124) to encourage differentiation of the transplanted cells into myotubes. In some cases, the mature myotubes, or precursors thereof, may be transplanted or injected into a site in the patient such as a muscle site, and they may promote myogenesis and/or muscle regeneration in the patient. In some cases, the transplanted cells are genetically unmodified cells including but not limited to: primary satellite cells, primary myoblast cells, embryonic stem cells, induced pluripotent stem cells, satellite cells differentiated in vitro from stem cells, or myoblasts differentiated in vitro from satellite cells or other cell type.

In some cases, the myotubes or myotube-like cells, or myotube precursor cells, may be genetically modified, prior to being introduced into a patient. For example, the cells (e.g., pluripotent stem cells, satellite cells, myoblasts, myotubes) may be genetically modified to correct a phenotype associated with a genetic muscle disease. As a result of a cell therapy provided herein is that the patient may experience improvements in muscle tone or function, including improved muscle strength. In some instances, subjects seeking to strengthen muscle tone or function for cosmetic, athletic, or other purposes may benefit from the methods and compositions provided in this disclosure.

The methods provided herein may involve treating subjects with myotube-precursor cells, mature myotubes or myotube-like cells that are derived from genetically-modified cells. The cells that are genetically modified may be any cell involved in myogenesis (e.g., pluripotent stem cell, satellite cell, satellite-like cell, myoblast, myoblast-like cell, immature myotube or myotube-like cell, or other muscle-precursor cell). For example, a differentiated cell (e.g., skin cell, fibroblast, blood cell) can be isolated from a subject with a genetic disease (e.g., Huntington's disease, Spinal Muscular Atrophy, Duchenne muscular dystrophy, etc.). The differentiated cell may then be subjected to conditions to become a pluripotent stem cell (e.g., to become an induced pluripotent stem cell). The pluripotent stem cell may be genetically modified or altered in order to rescue or improve the disease condition. These genetically modified pluripotent cells may then be differentiated to satellite cells or satellite-like cells and then myoblast and myoblast-like cells that can be differentiated into mature myotubes according to the methods described herein. These genetically-modified cells (e.g., genetically-modified pluripotent stem cells, genetically-modified satellite cells, genetically-modified myoblasts, genetically-modified mature myotubes) can be transplanted into the subject to reduce the effects of a disease or disorder. The transplanted cells, or the myotubes differentiated therefrom, may be less likely to invoke an immune response in the subject than myotubes derived from a different subject.

In some cases, the cells and/or compounds disclosed herein (e.g., checkpoint inhibitors, Chk1 inhibitors, CHIR-124) may be used to treat patients with muscular degenerative diseases or muscular disorders stemming from a variety of causes, including, but not limited to, genetic disorders sporadic diseases, cachexia, muscle strain, muscle injury, muscle atrophy, as well as sarcopenia and the general aging process. The disclosed compounds (e.g., checkpoint inhibitors, Chk1 inhibitors, CHIR-124) may be administered to a patient by a variety of routes, including but not limited to, orally, intravenously, intramuscularly, subcutaneously, and transdermally. The compounds may promote myogenesis and/or muscle regeneration in the patient. As a result, the patient may experience improvements in muscle tone or function, including improved muscle strength. In some instances, subjects seeking to strengthen muscle tone or function for cosmetic, athletic, or other purposes may benefit from the methods and compositions provided in this disclosure.

In some embodiments, the mature myotubes or myotube-like cells provided herein (including myotubes derived from genetically-modified or unmodified pluripotent stem cells) can be used in drug-screening assays, particularly assays to identify agents for ameliorating a muscle defect. The mature myotubes or myotube-like cells may also be useful for disease modeling and other types of disease research. In some instances, mature myotubes or myotube-like cells may be differentiated from a human pluripotent stem cell that is genetically modified to have an identical or substantially similar mutation that causes a genetic disease in humans. Such mature myotubes or myotube-like cells may then be screened for agents that reverse or reduce the effects of the mutation.

II. General Methods

This disclosure provides methods and compositions for producing and culturing mature myotubes or myotube-like cells that have adult-like morphology. The disclosure further describes methods for using said mature myotubes both in vitro, such as in drug screening assays, and in vivo, by using mature myotubes as a therapeutic to treat subjects with muscular deficiencies. The disclosure also provides methods of screening and identifying compounds that modulate muscle development. This disclosure also provides methods of administering a compound provided herein to a subject (e.g., human patient) in order to encourage muscle differentiation or mature myoblast formation in vivo. In some cases, the compound is administered along with administration of myotube precursor cells (e.g., myoblasts, myoblast-like cells, satellite cells, pluripotent stem cells, etc.)

A general overview of a differentiation process that produces mature myotubes or myotube-like cells is shown in FIG. 1. Production or formation of mature myotubes may include maturation of a myotube or generation of new myotubes de novo. The methods may involve obtaining or providing pluripotent stem cells (e.g., embryonic stem cells or induced pluripotent stem cells) (100). The induced pluripotent stem cells may be obtained from differentiated cells from a human subject. The pluripotent stem cells (e.g., embryonic stem cells or induced pluripotent stem cells) may be genetically modified. The methods may also involve contacting the pluripotent stem cells with one or more compounds in a medium to differentiate the pluripotent stem cells (e.g., by chemical differentiation) into satellite cells or satellite-like cells (110), or otherwise obtaining satellite-like cells. The methods may also involve further differentiating the satellite cells or satellite-like cells into myoblasts (or myoblast-like cells) by incubating the satellite cells or satellite-like cells in a medium to differentiate the satellite cells or satellite-like cells into myoblasts or myoblast-like cells (120), or otherwise obtaining myoblasts or myoblast-like cells.

The methods provided herein generally relate to generating myotubes or myotube-like cells from myoblasts or myoblast-like cells, and often relates to producing mature myotubes or mature myotube-like cells. The myoblasts or myoblast-like cells used to produce myotubes may be obtained from any method known in the art. For example, the myoblasts may be primary myoblasts or derived from primary myoblasts. The primary myoblasts may be directly obtained from a subject, such as by surgical removal of myoblasts from the subject or from a cadaver. In some cases, the myoblasts or myoblast-like cells are generated in vitro, such as from satellite cells or satellite-like cells (e.g., by differentiating such satellite cells in vitro) (120). In preferred embodiments, such myotubes or myotube-like cells generated by the methods provided herein resemble mature myotubes and have mature morphology. In some cases, myoblasts or myoblast-like cells may be incubated in a medium capable of generating mature myotubes or myotube-like cells from the myoblasts or myoblast-like cells (140). In some cases, the medium is a medium supplemented with a compound provided herein. The medium may, in some instances, be a myotube medium (130) that on its own may cause the myoblasts or myoblast-like cells to form immature myotubes or immature myotube-like cells (150). In some cases, the myotube medium (e.g., Genea Biocells Myotube Medium) is supplemented with one or more compounds capable of causing the myoblasts or myoblast-like cells to form mature myotubes or mature myotube-like cells with adult-like morphology (160). The above-described steps of the method may occur in any order and in any combination. Interspersed amongst these steps may be steps to maintain the cells, including culturing or expanding the cells. In addition, cells may be stored after any step in the methods.

The mature myotubes, myotube-like cells, or compounds in combination with myotube precursor cells provided herein can be used in many contexts, including as cell therapies (170). In some examples of cell therapies, myotube precursor cells, myotubes, or myotube-like cells may be transplanted into a subject (e.g., a patient) and impact muscle morphology or function, such as by adding to muscle mass, promoting myogenesis and/or promoting muscle regeneration in vivo. In some cases, the transplanted cells or factors secreted therefrom may protect muscles by mitigating an inflammatory response. In some cases, the transplanted cells are cells produced from cells obtained from a different subject. In some cases, a subject receives transplanted cells that are derived from a cell sample originally obtained from the subject. In some cases, the cell sample obtained from the subject comprises differentiated cells (e.g., fibroblasts, blood cells) that are induced to form induced pluripotent stem cells. The induced pluripotent stem cells may be genetically modified, for example, to correct a phenotype.

In some cases, the mature myotubes or myotube-like cells may be used for drug screening (180). For example, the mature myotubes or myotube-like cells may exhibit a muscle-disease-related phenotype. Such cells may then be used to identify a drug candidate that reverses such muscle-disease-related phenotype.

Figure 2:
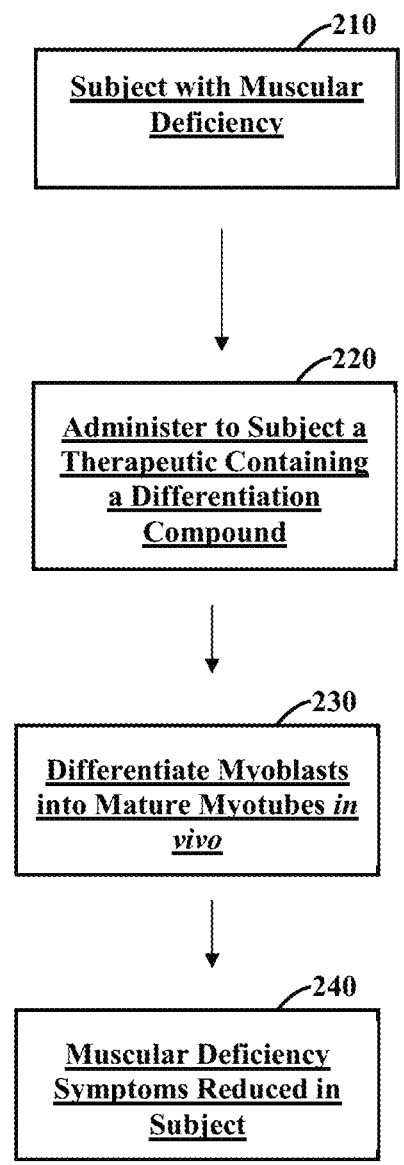
FIG. 2 is an overview of a method of treating a subject with a muscular deficiency with a compound that ameliorates the muscular deficiency.

FIG. 2 illustrates a method of treating a subject with a muscular disease or other muscular deficiency (210) with a compound (e.g., Chk1 inhibitor such as CHIR-124) (220) that at least partly ameliorates, treats, or reduces the subject's muscular deficiency symptoms (240). Without wishing to be bound by theory, the compound may cause myotubes or myotube-like cells to be generated in vivo from certain cells (e.g., myoblasts, satellite cells, myoblast-like cells, satellite-like cells) (230). The cells from which the myotube or myotube-like cells are generated may be the subject's endogenous cells, such as myoblast or satellite cells. In some cases, the cells from which the myotubes are generated are cells that have been transplanted into the subject, such as primary myoblasts or satellite cells from the subject, or myoblast-like or satellite-like cells produced from the subject's cells (e.g, by differentiating pluripotent stem cells derived from a subject). In some cases, the cells from which the myotubes are generated are induced pluripotent stem cells produced from the subject's cells or are another type of pluripotent stem cell, such as embryonic stem cell (ES Cell). The compound may be administered to the subject by various approaches, including but not limited to, orally, intravenously, buccaly, intramuscularly, topically, subcutaneously, and transdermally. The subject may experience ameliorated symptoms of muscular deficiency by experiencing improvements in muscle tone or function, including improved muscle strength. In some instances, subjects seeking to strengthen muscle tone or function for cosmetic, athletic, or other purposes may benefit from the methods and compositions provided in this disclosure.

Figure 3:
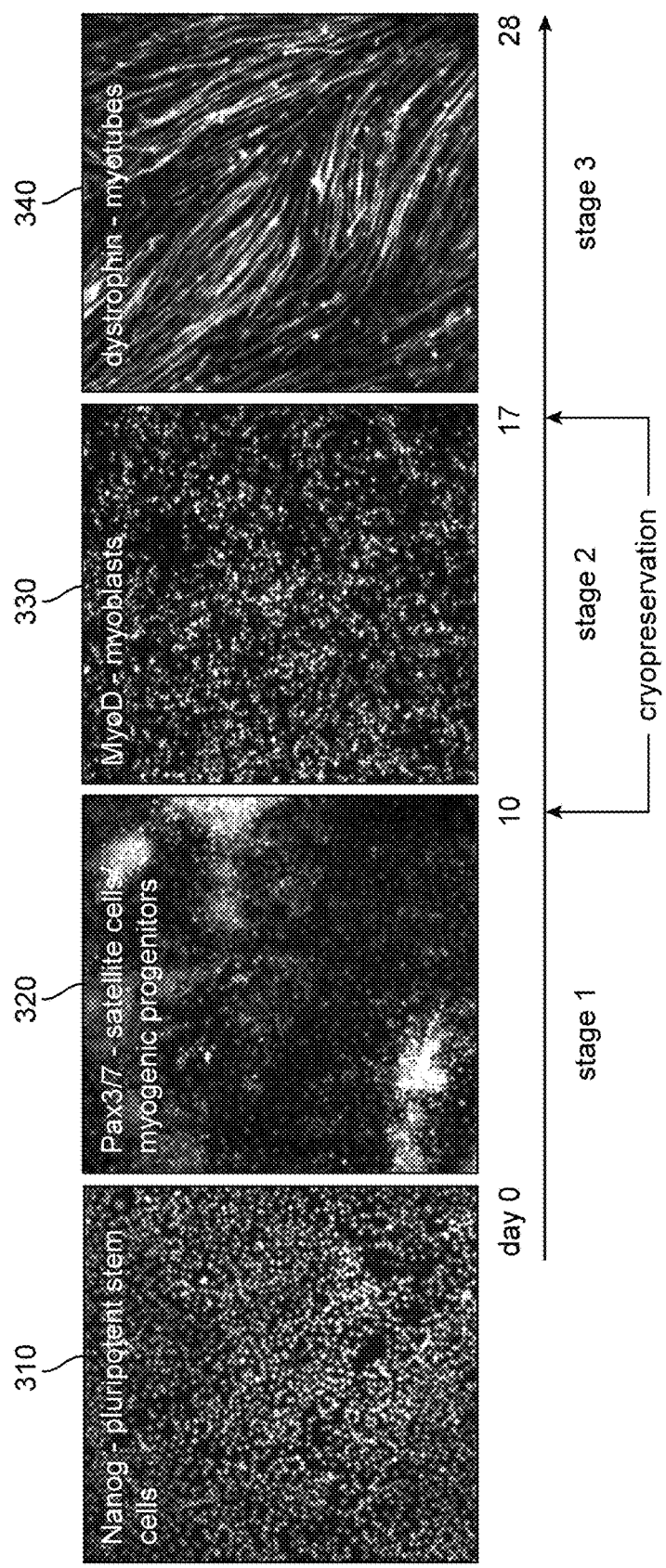
FIG. 3 is an illustration of four stages of differentiation from pluripotent stem cells to myotubes in accordance with embodiments of the present disclosure.
Figure 4A:
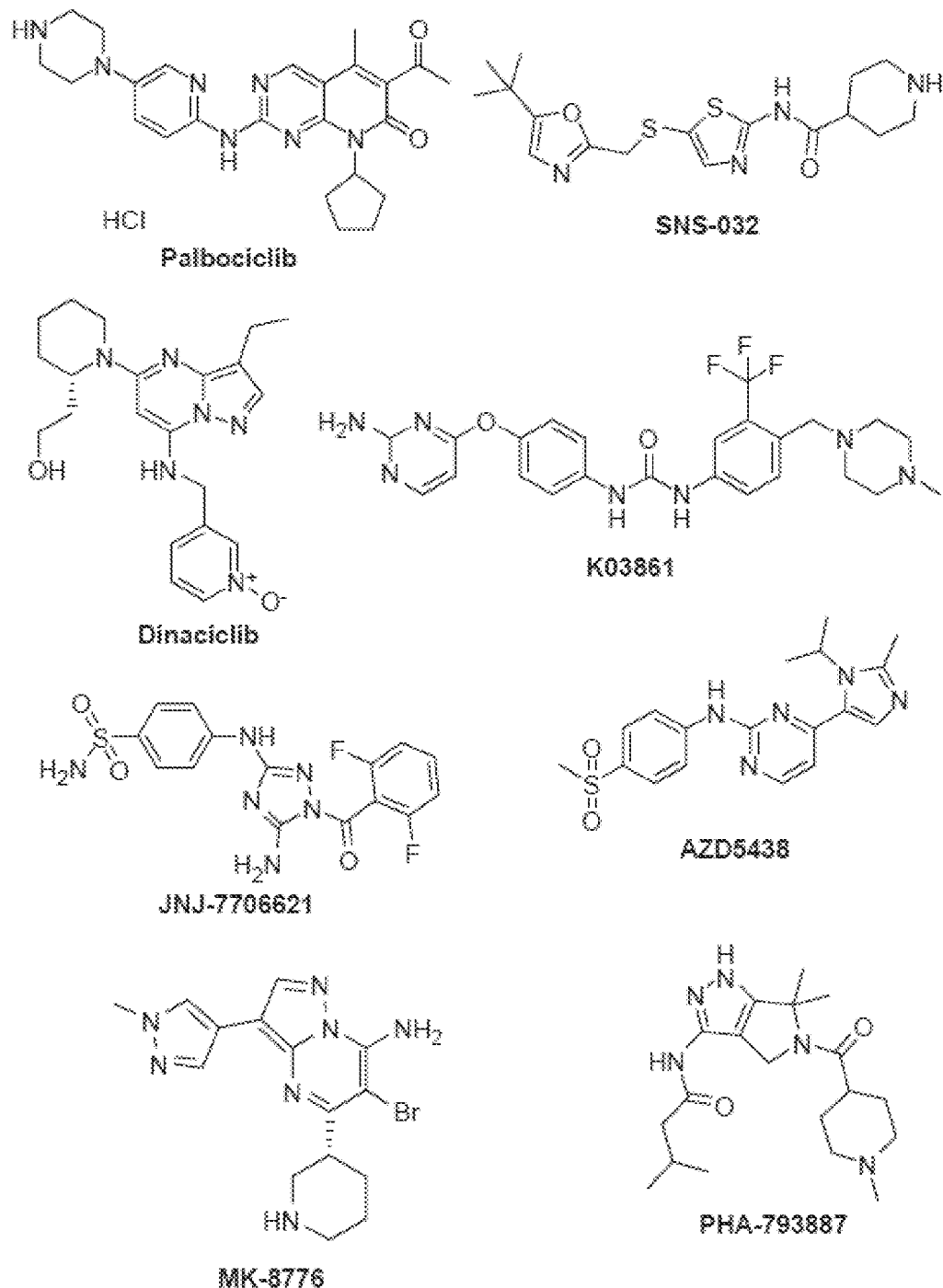
FIGS. 4A, 4B, 4C, 4D, 4E, and 4F show representative kinase inhibitor molecules used in the myotube formation assay that target kinase enzymes involved in cell cycle signaling and DNA repair pathways.
Figure 4B:
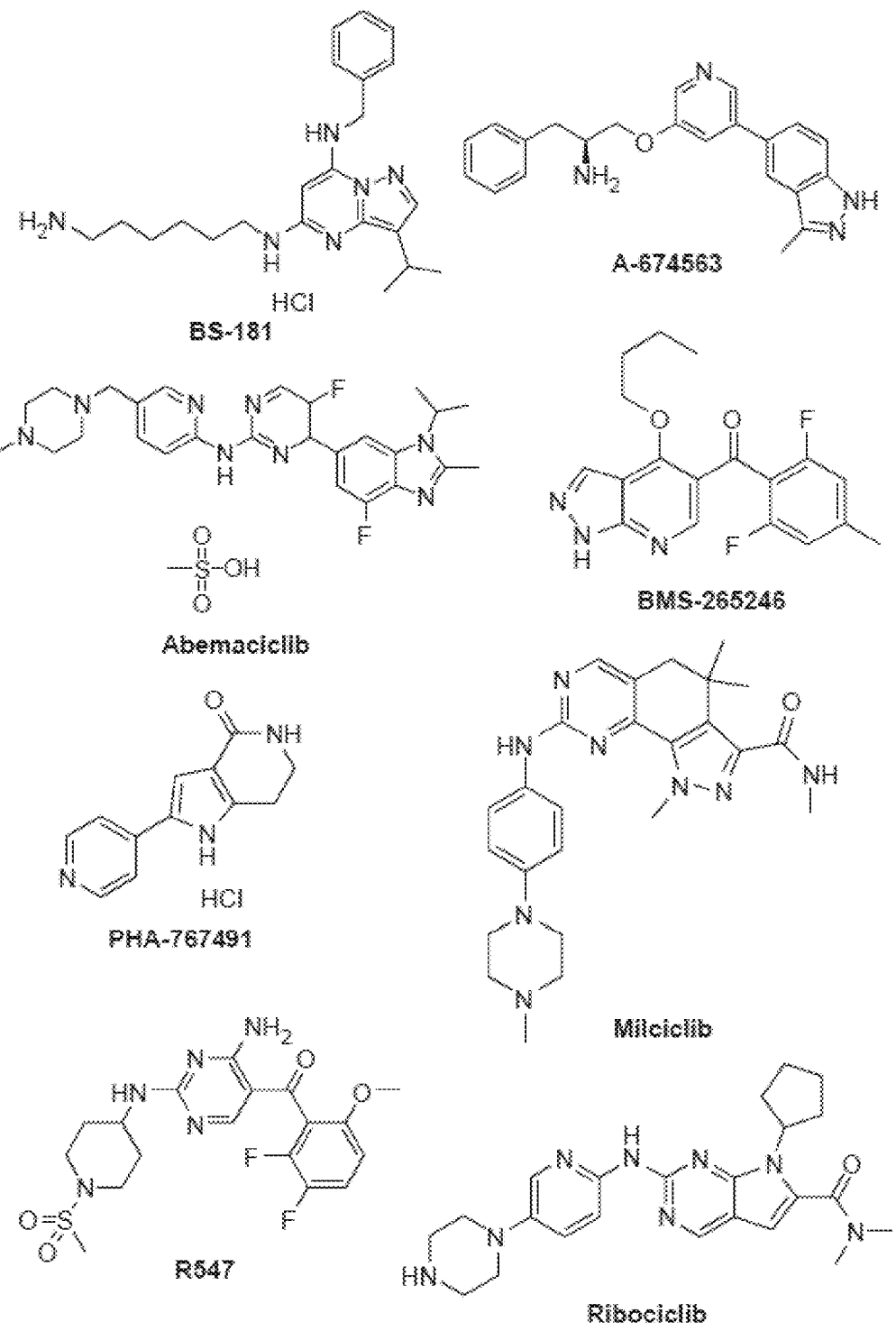
Figure 4C:
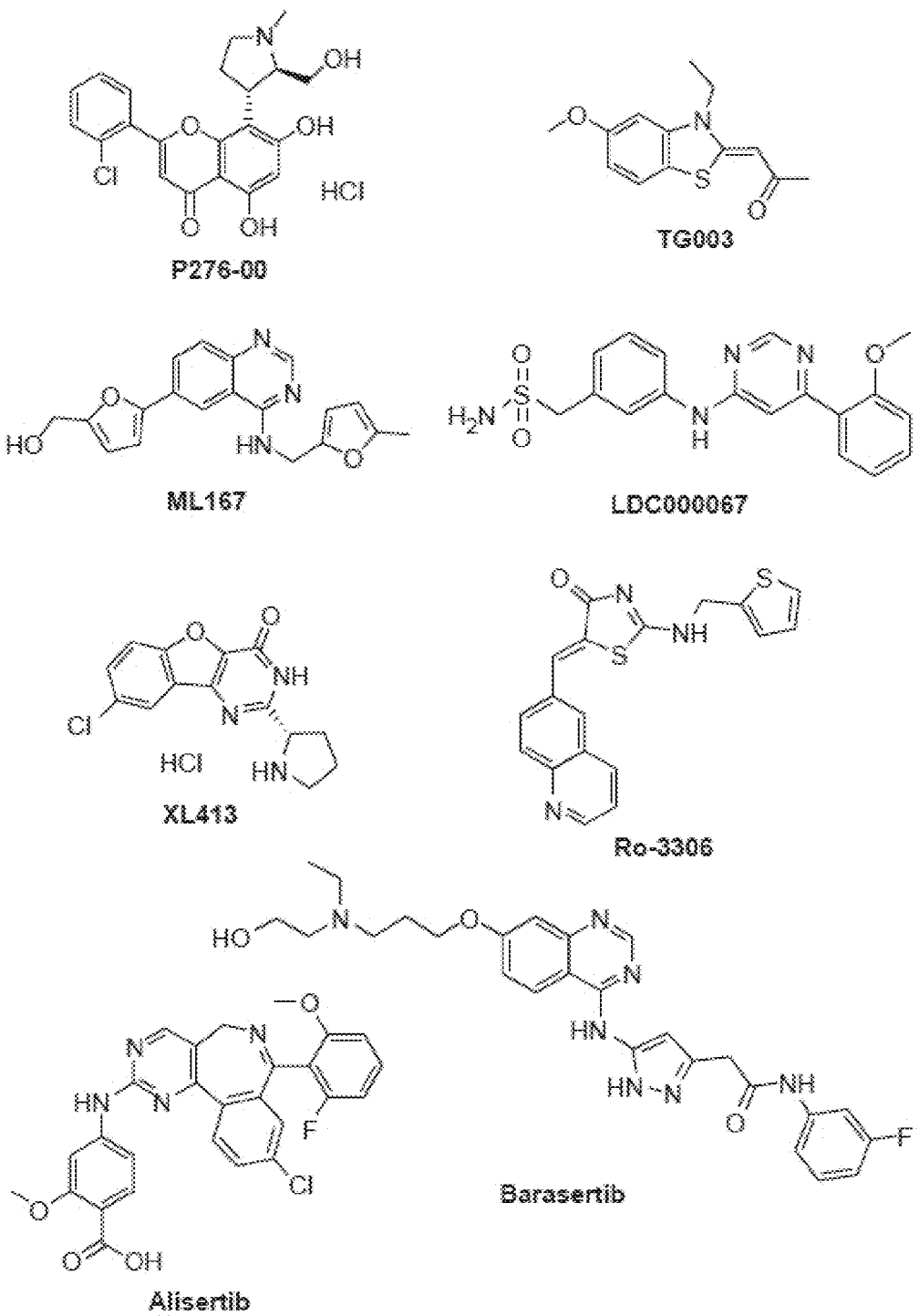
Figure 4D:
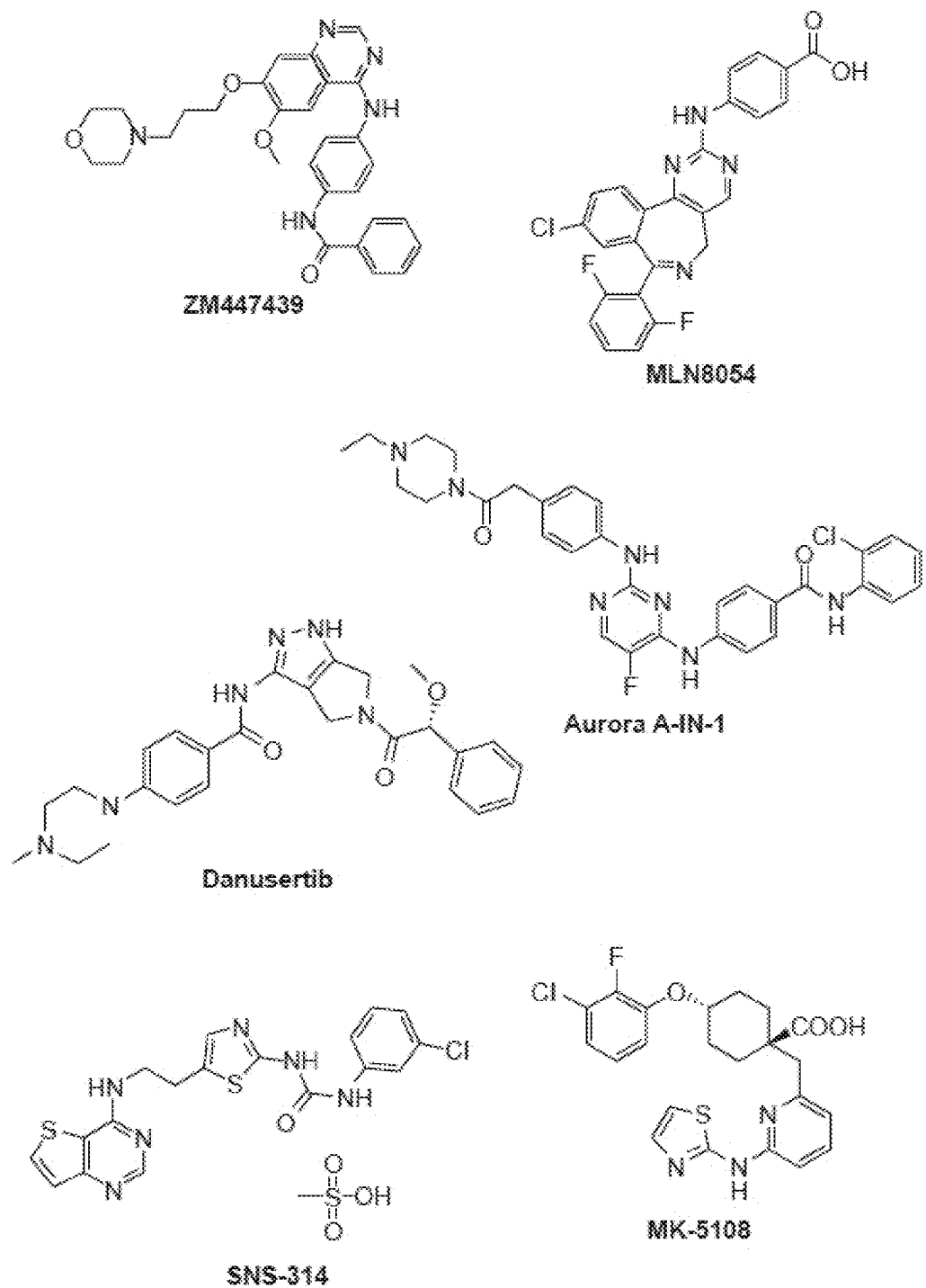
Figure 4E:
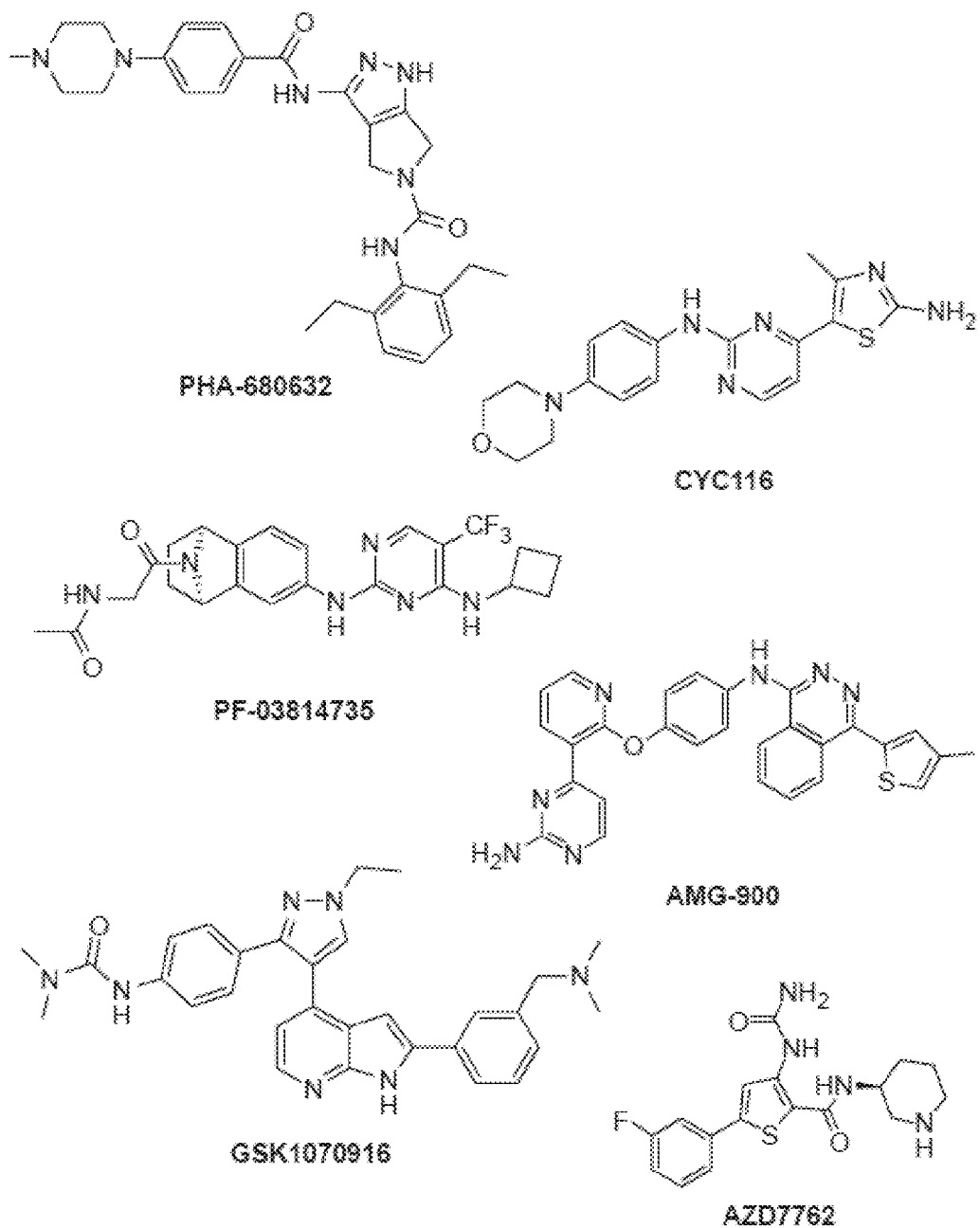
Figure 4F:
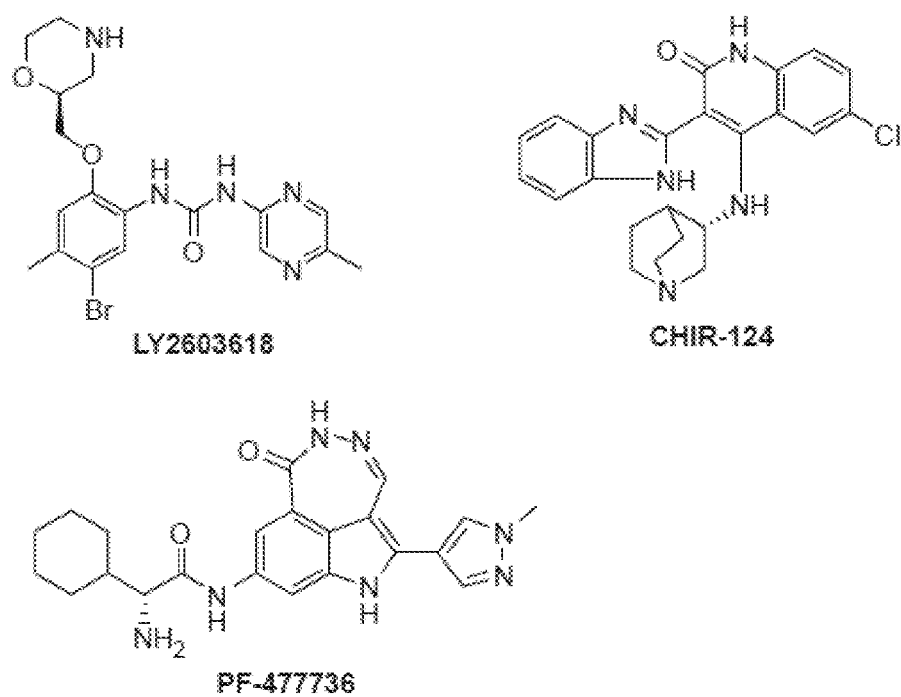

FIG. 3 illustrates four stages of differentiation from pluripotent stem cells (310) to myotubes (340). Pluripotent stem cells may be differentiated into satellite cells (320), myoblasts (330), and myotubes (340) in accordance with embodiments of the present disclosure.

Figure 5A:
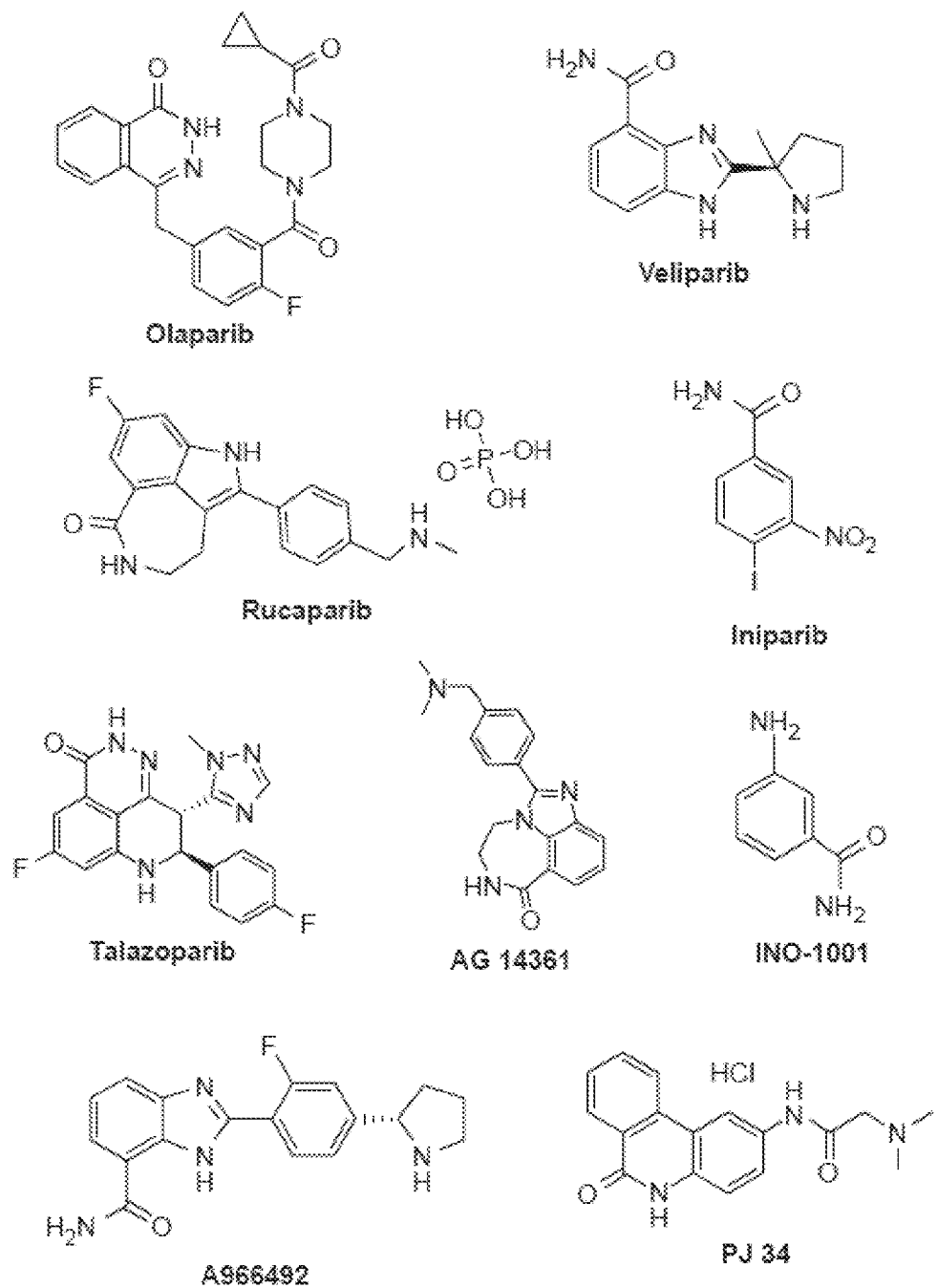
FIGS. 5A and 5B show representative poly ADP-ribose polymerase (PARP) inhibitor molecules used in the myotube formation assay.
Figure 5B:
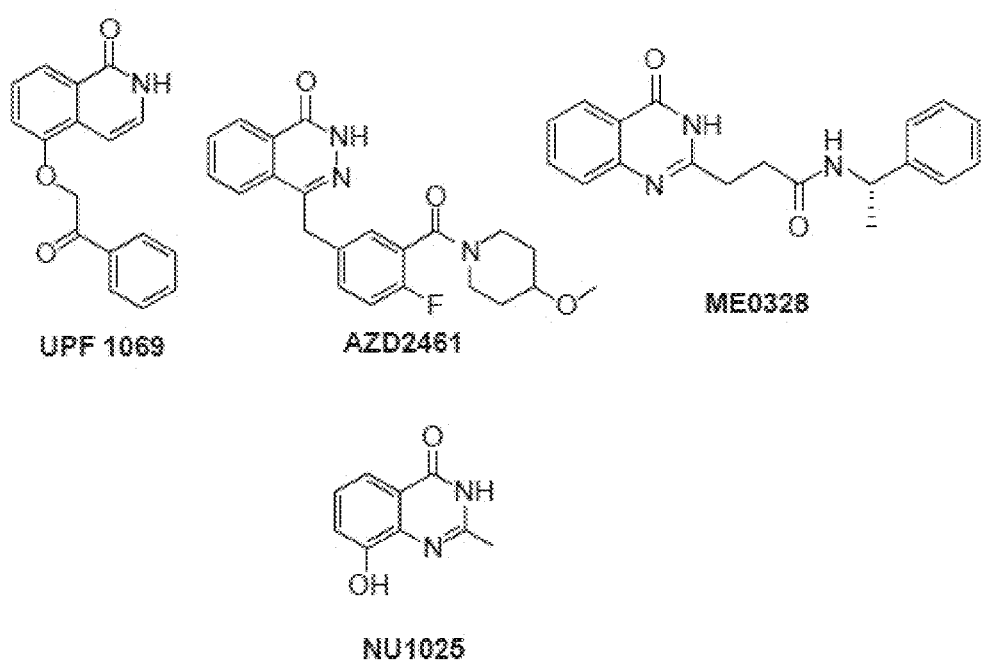
Figure 6A:
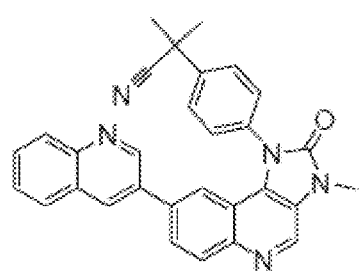
FIGS. 6A and 6B show representative small molecules used in the myotube formation assay that target molecules involved in PI3K/Akt, mTOR, and MAPK signaling pathways.
Figure 6A:
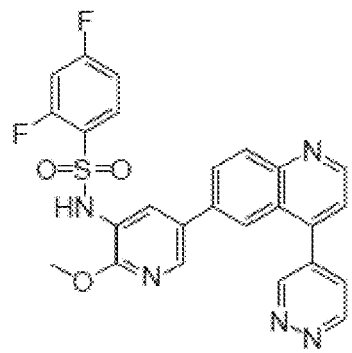
Figure 6A:
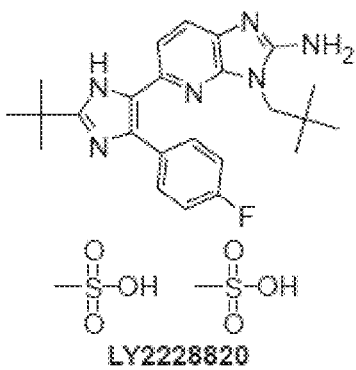
Figure 6A:
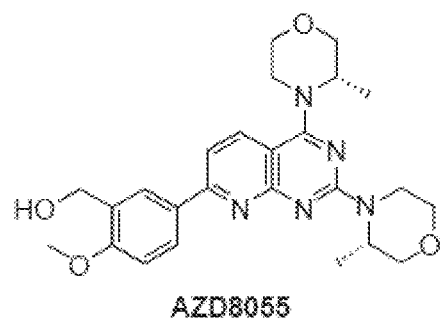
Figure 6A:
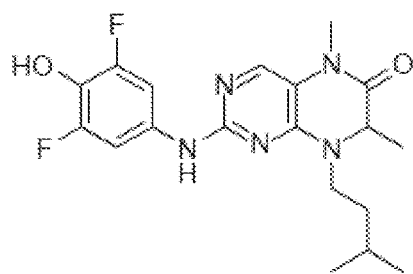
Figure 6A:
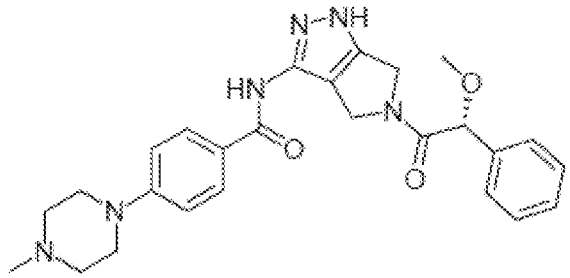
Figure 6B:
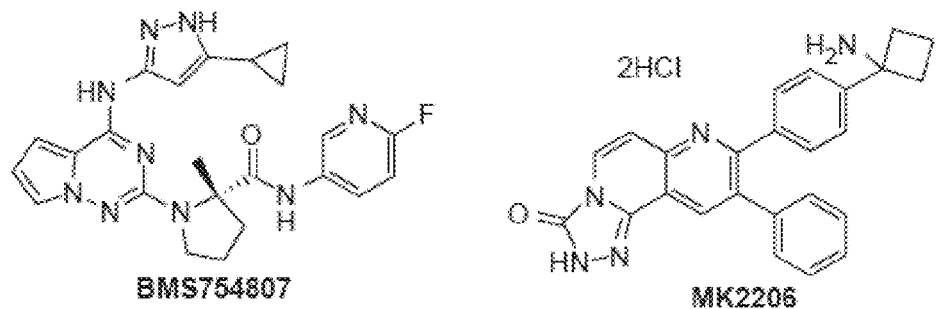
Figure 6B:
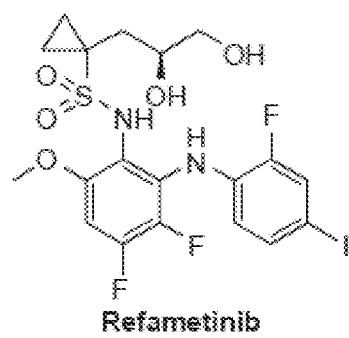
Figure 7A:
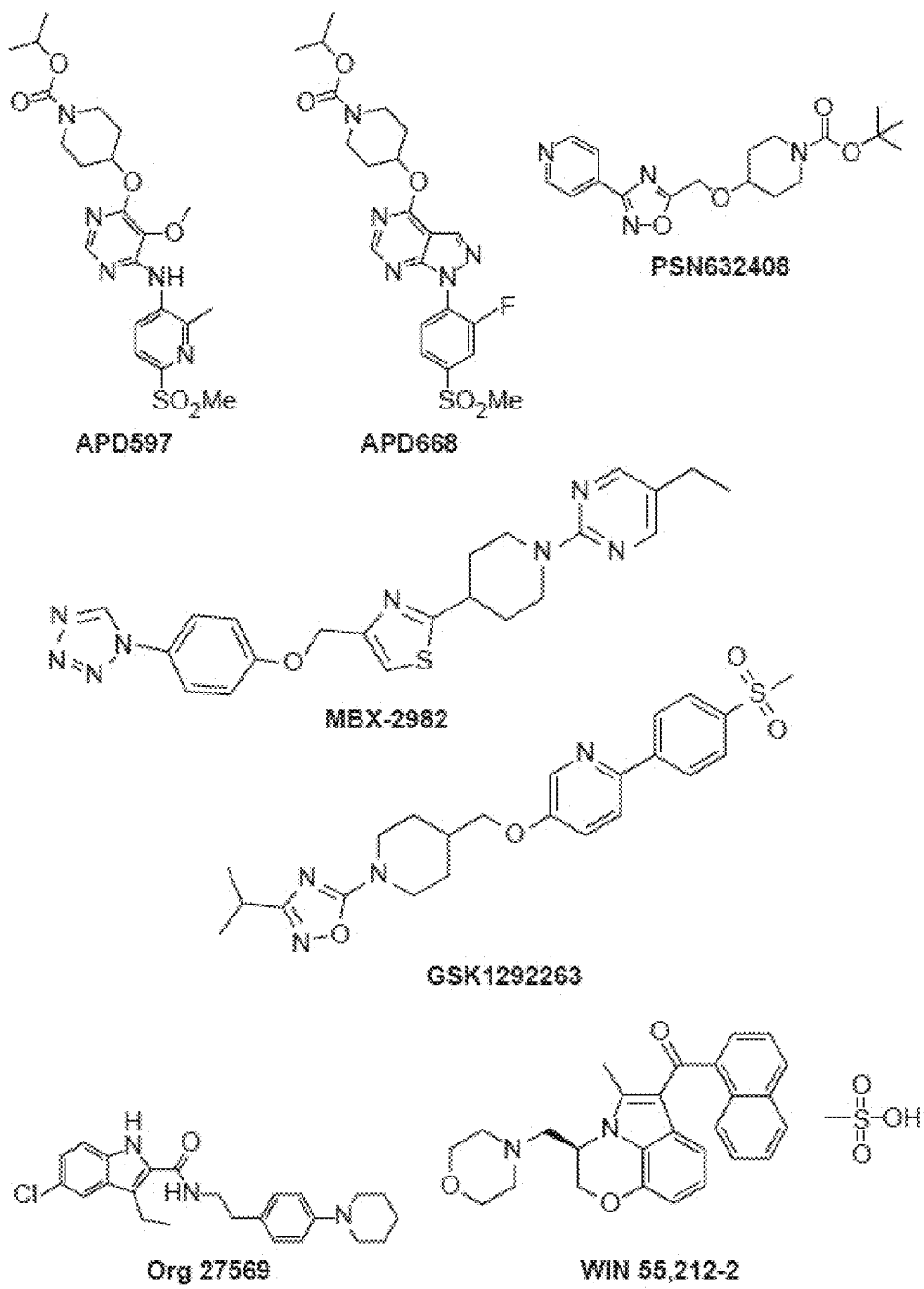
FIGS. 7A and 7B show representative small molecules used in the myotube formation assay that are modulators of G-protein coupled receptor signaling.
Figure 7B:
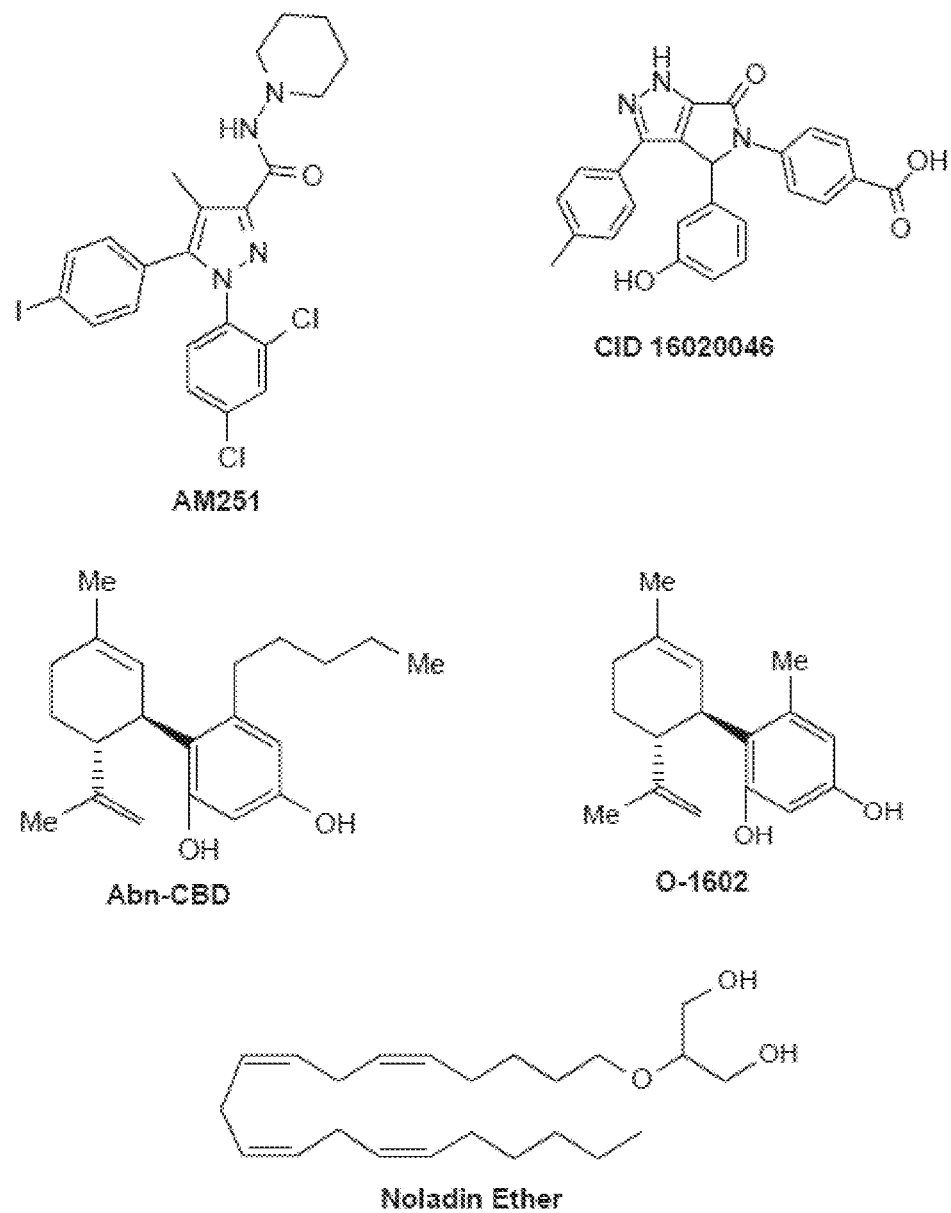
Figure 8A:
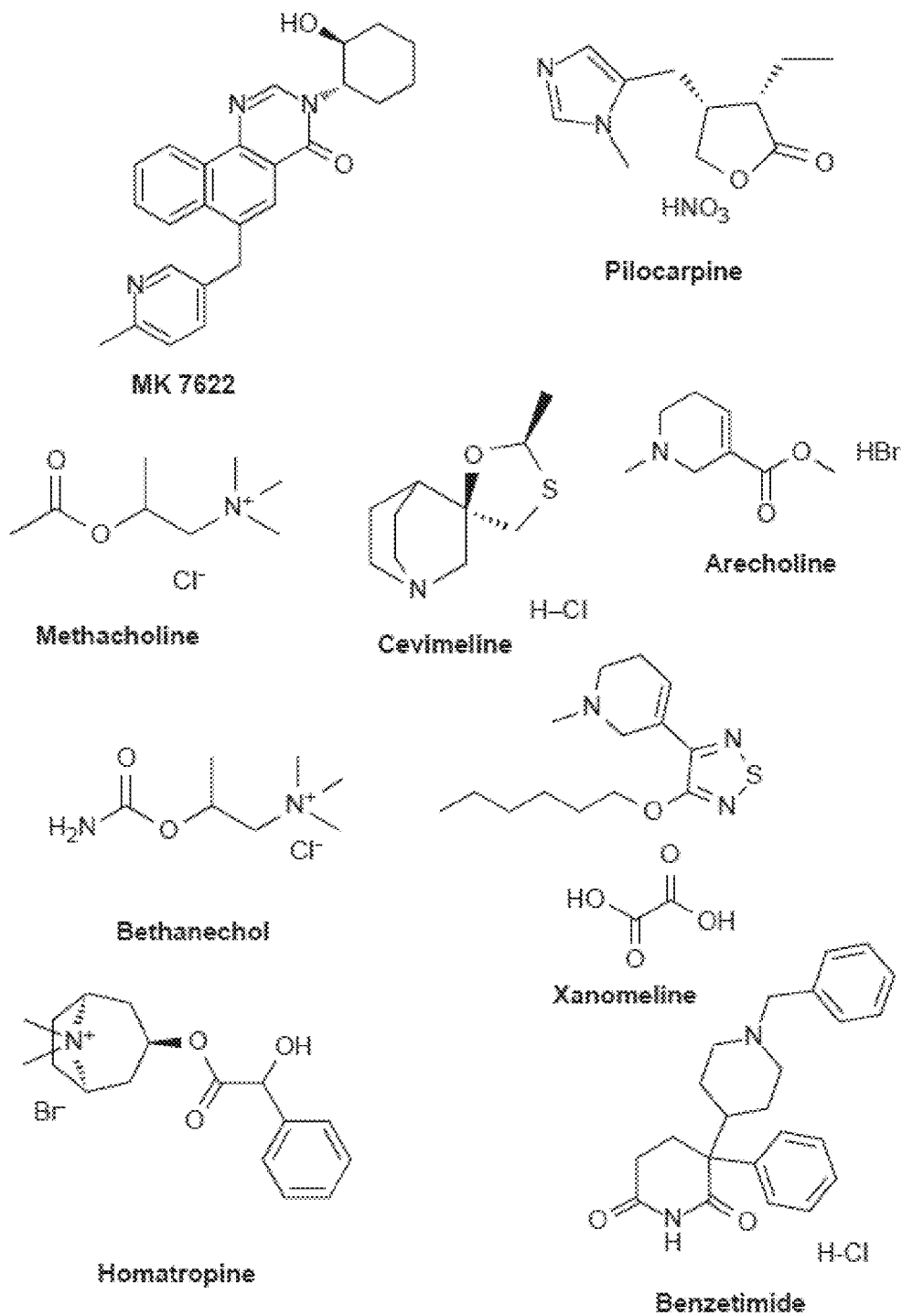
FIGS. 8A and 8B show representative small molecules used in the myotube formation assay that are modulators of muscarinic acetylcholine receptors.
Figure 8B:
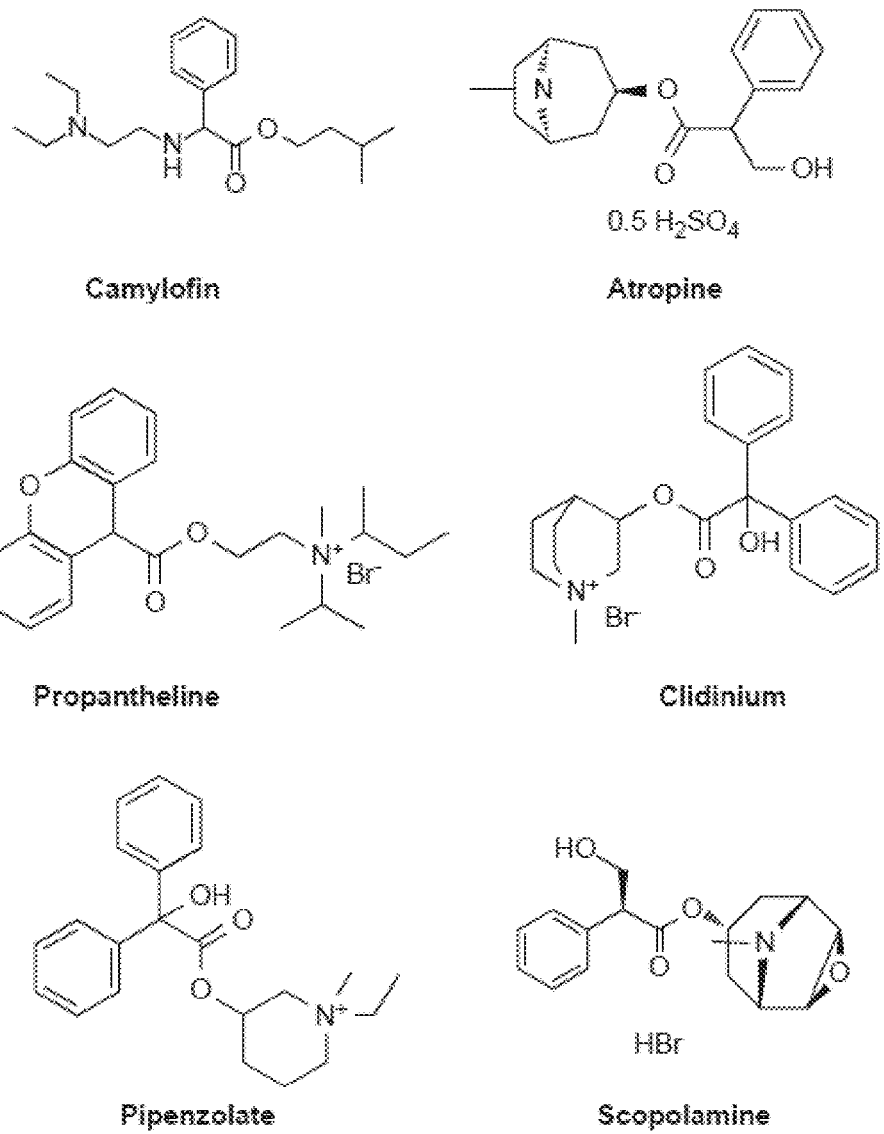

FIGS. 4A-4F, 5A-5B, 6A-6B, 7A-7B, and 8A-8B depict exemplary chemical structures of compounds that may be used to enhance formation or development of mature myotubes in a subject when administered as a monotherapy or as an adjunct to be applied with cell transplantation as described herein. FIGS. 4A, 4B, 4C, 4D, 4E, and 4F depict compounds that target enzymes in cell signaling and DNA repair pathways, such as palbociclib, SNS-032, dinaciclib, K03861, JNJ-7706621, AZD5438, MK-8776, PHA-793887, BS-181, A-674563, abemaciclib, PHA-767491, milciclib, ribociclib, R547, P276-00, TG003, ML167. LDC000067, XL413, Ro-3306, alisertib, barasertib, ZM447439, MLN8054, Danusertib, aurora A-IN-1, SNS-314, MK-5108, PHA-680632, CYC116, PF-03814735, AMG-906, GSK1070916, AZD7762, LY2603618, CHIR-124, and PF-477736. FIGS. 5A and 5B depict compounds that inhibit PARP (Poly ADP ribose polymerase), such as olaparib, veliparib, rucaparib, iniparib, talazoparib, AG14361, INO-1001, A996492, PJ34, UPF1069, AZD2461, ME0328, and NU1025. FIGS. 6A and 6B depict compounds that target PI3K/AKT, mTOR, or MAPK pathways such as BEZ235, omipalsib, LY2228820, AZD8055, BI-D1879, danusertib, BMS754807, MK2206, and refametinib. FIGS. 7A and 7B depict compounds that target GPCR signaling, such as APD597, APD668, PSN632408, MBX2982, GSK1292263, org 27569, WIN 55,212-2, AM251, CID16020046, Abn-CBD, O-1602, and noladin ether. FIGS. 8A and 8B depict compounds that modulate the mAChR (muscarinic acetylcholine receptor) GPCR class, such as MK7622, pilocarpine, methacholine, cerimeline, arecholine, xanomeline, bethanechol, homatropine, benzetimide, camylofin, atropine, propantheline, clidinium, pipenzolate, and scopolamine.

Figure 9A:
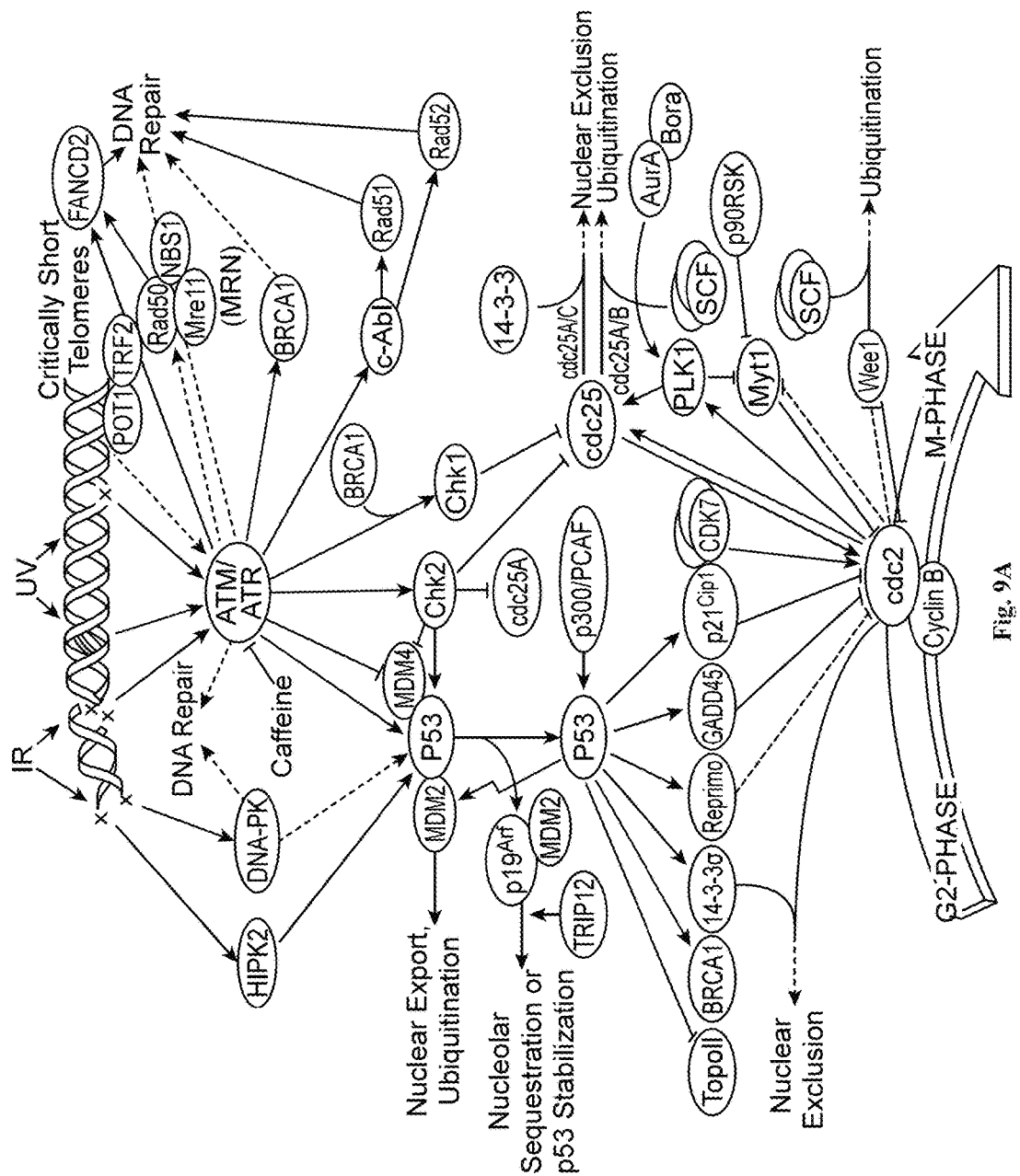
FIGS. 9A, 9B, and 9C show representative cell cycle signaling cascades 9A, GPCR signaling pathways 9B; and PIK3/Akt, mTOR, and MAPK signaling pathways 9C.
Figure 9B:
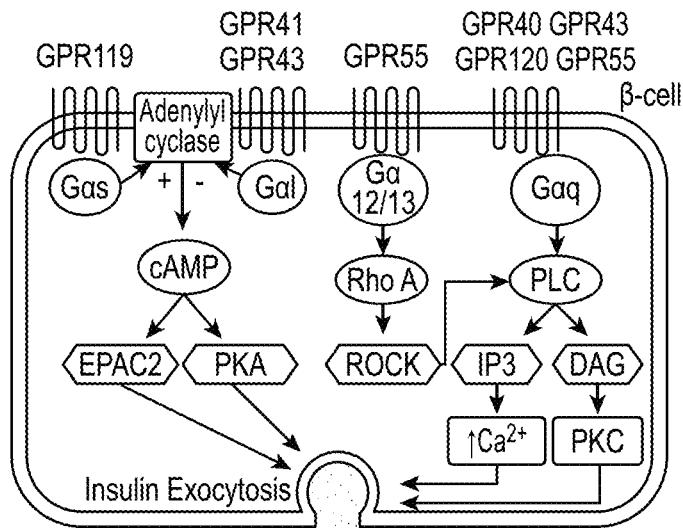
Figure 9B:
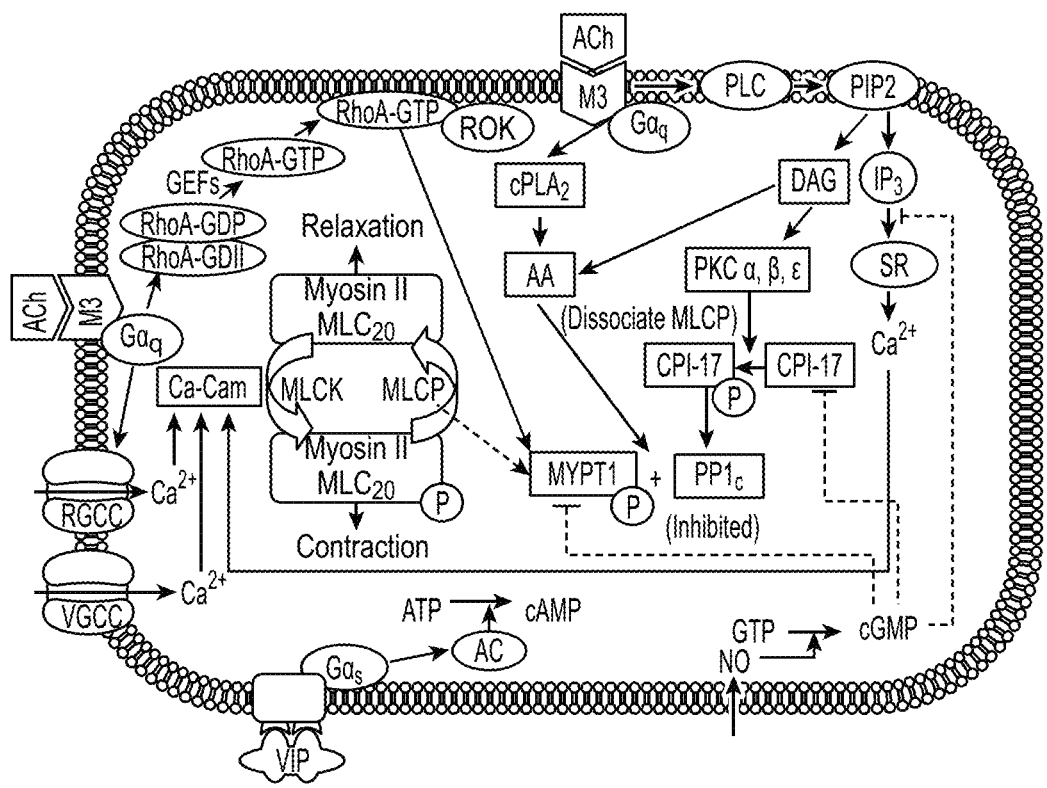
Figure 9C:
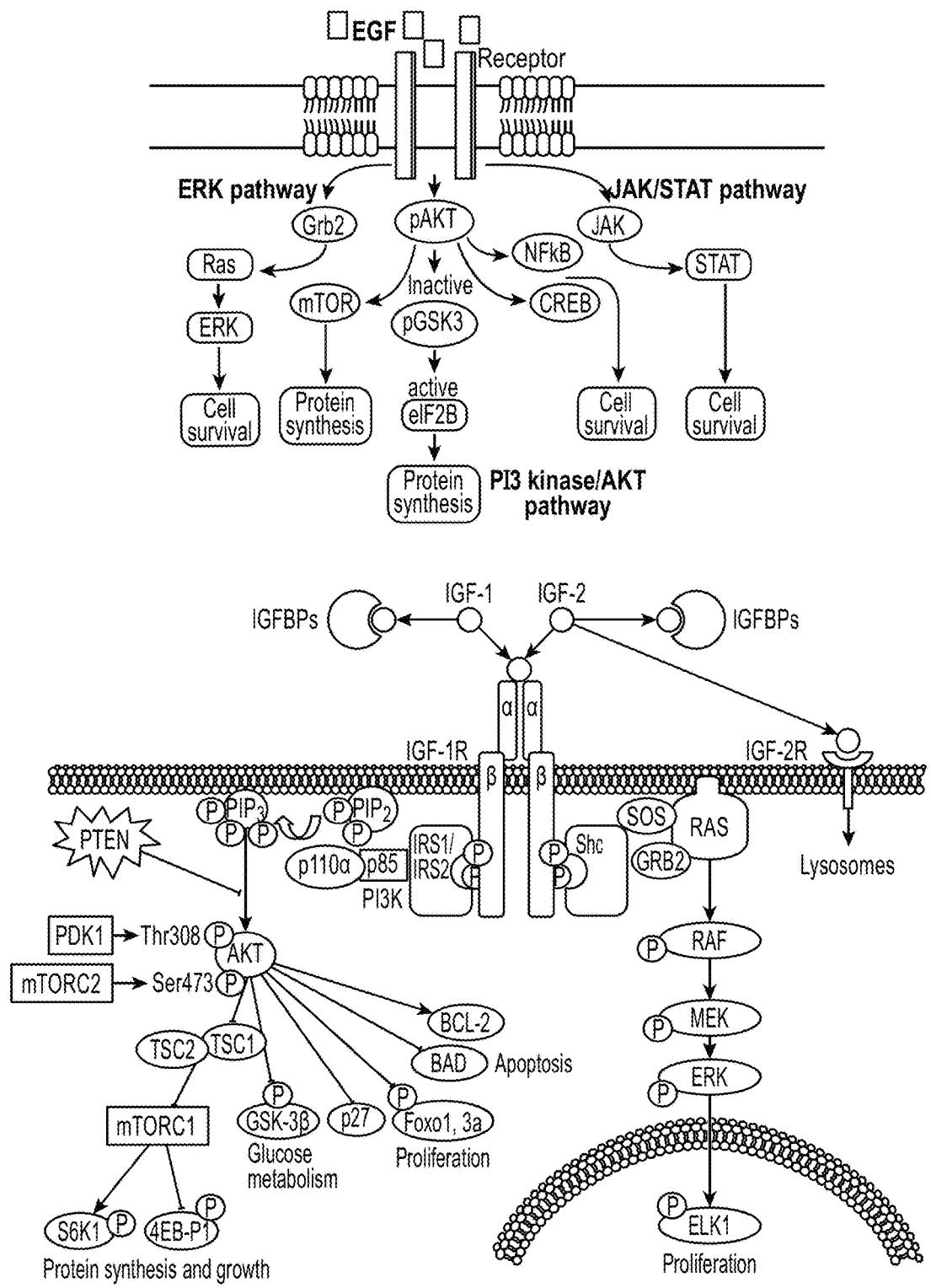

FIGS. 9A, 9B, and 9C depict pathways and protein targets within them that may be modulated by the compounds above (in FIGS. 4A-4F, 5A-5B, 6A-6B, 7A-7B, and 8A-8B) to enhance production of mature myotubes in a subject when administered as a monotherapy, or as an adjunct to be applied with cell transplantation as described herein. FIG. 9A depicts signaling relationships involved in cell-cycle progression (such as the G2- to M-phase transition) involving proteins such as p53, ATM/ATR, Chk proteins (Chk1/Chk2), Cdc25 phosphatase, and the E3 ligase MDM2. FIG. 9B depicts GPCR signaling relationships involved in exocytosis and muscle contraction/relaxation, which involve proteins such as mAChR receptors (M3 in the figure) PKCα, PKCβ, and PKCγ. FIG. 9C depicts signaling relationships of PI3K/AKT, mTOR, and MAPK proteins, which affect cellular processes such as cell survival, cell proliferation, and protein synthesis.

Figure 10A:
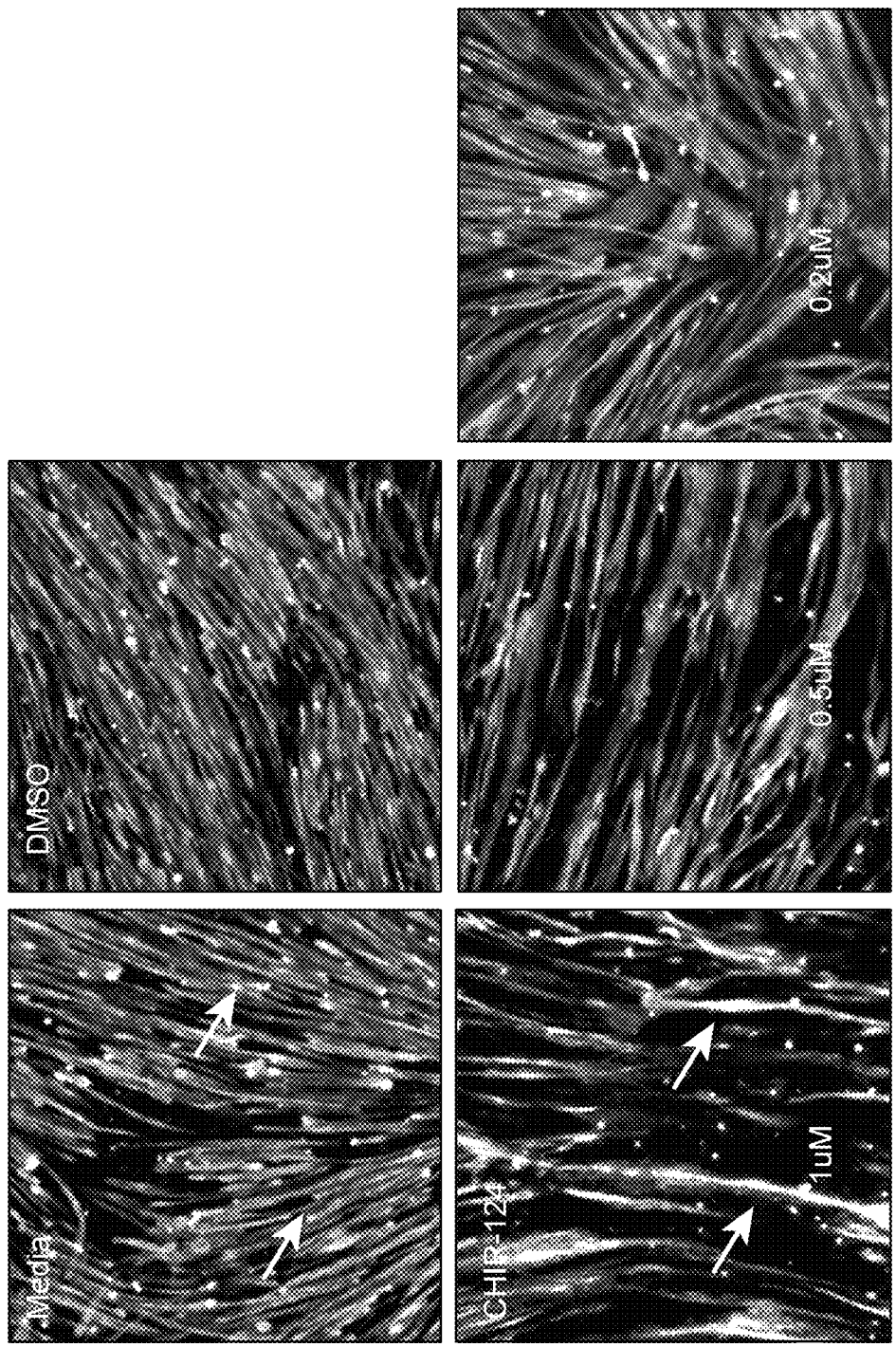
FIGS. 10A, 10B, 10C, and 10D are immunofluorescence images and accompanying graphical depictions of properties of stem cell-derived myoblasts differentiated into myotubes upon treatment with CHIR-124 (Chk1 inhibitor) tested at different doses in Myotube Medium for 5 days. Cells were fixed and stained with antibodies specific for myosin heavy chain; and nuclei were counterstained with Hoechst. The cells are shown at 20× magnification 10A. Stained cells were also quantified by image analysis; the properties depicted in bar graphs are myotube diameter 10B (upper panel), numbers of cells with multiple nuclei 10B (lower panel), breakdown of cells with multiple nuclei 10C (upper panel), total myotube area of total cells in the image 10C (lower panel), myotube area of individual cells 10D (upper panel), and mean or normalized areas of individual cells 10D (lower panel).
Figure 10B:
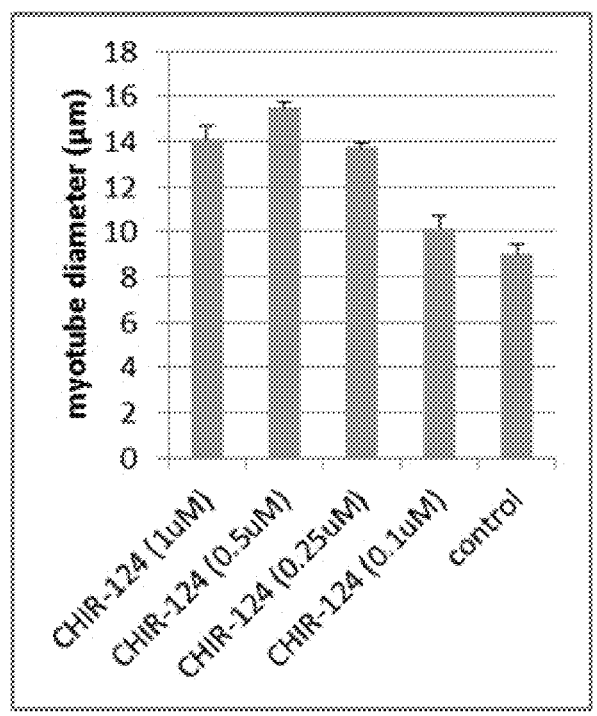
Figure 10B:
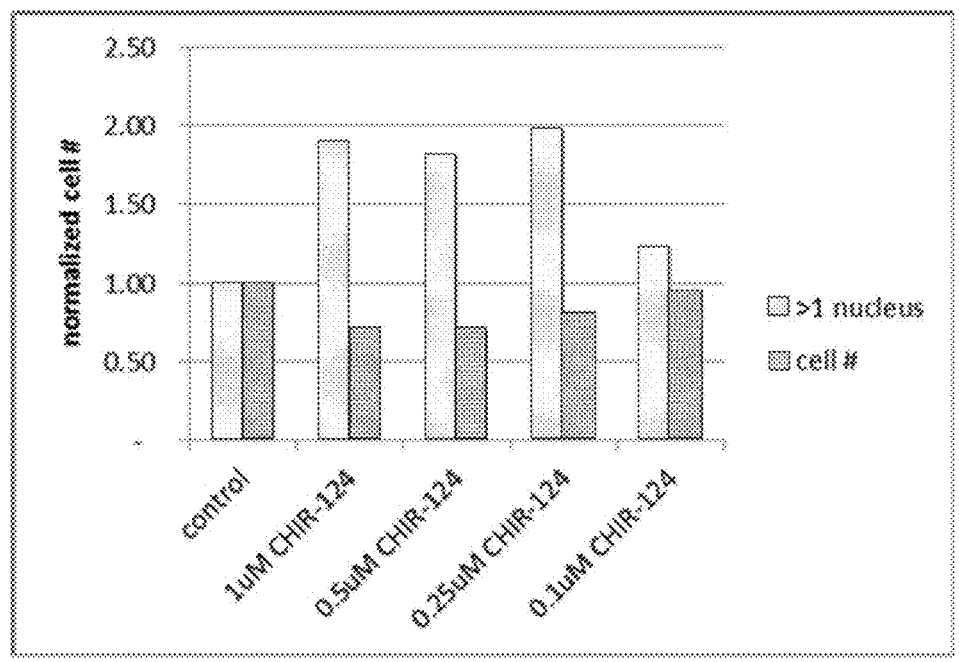
Figure 10C:
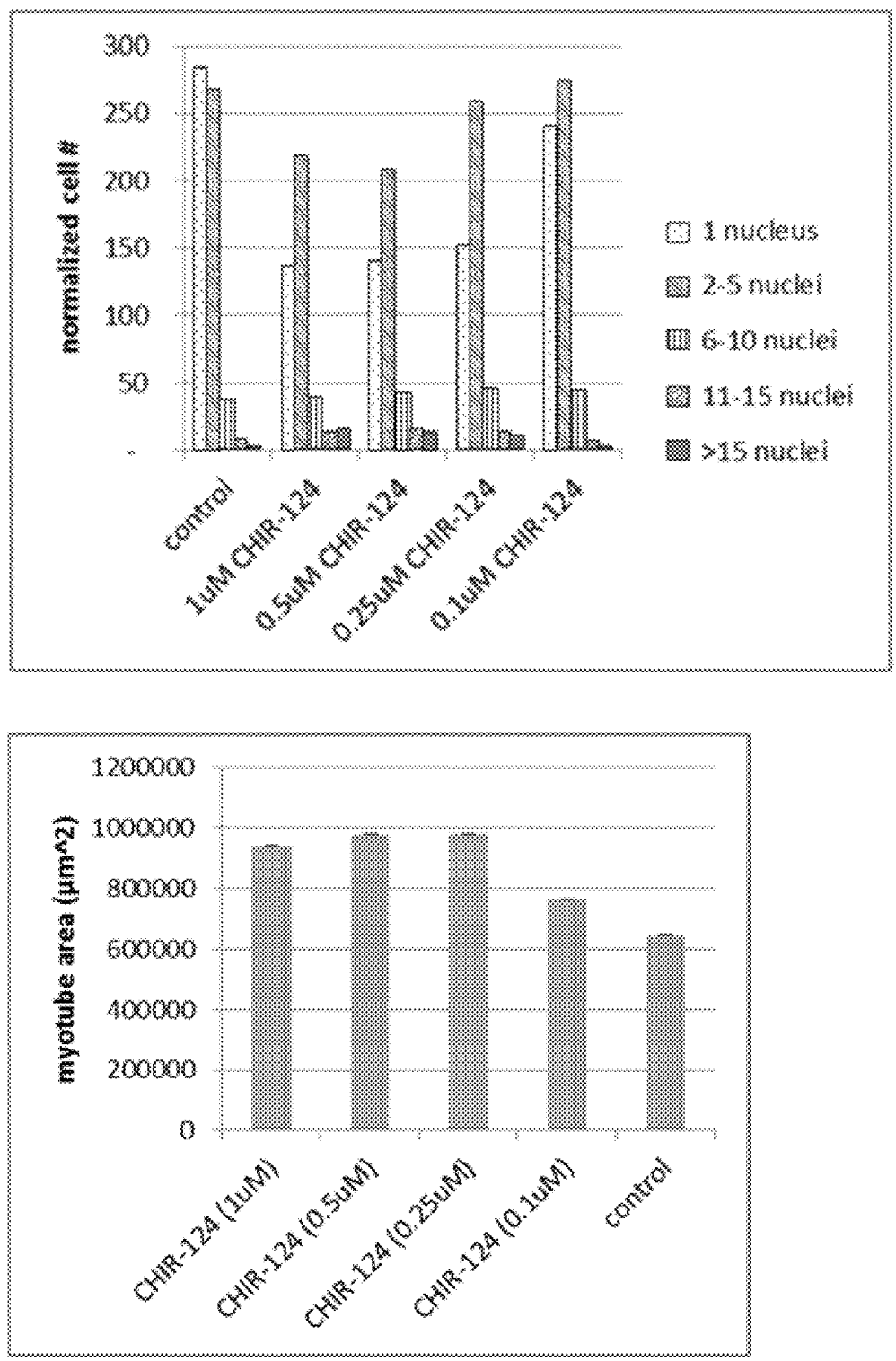
Figure 10D:
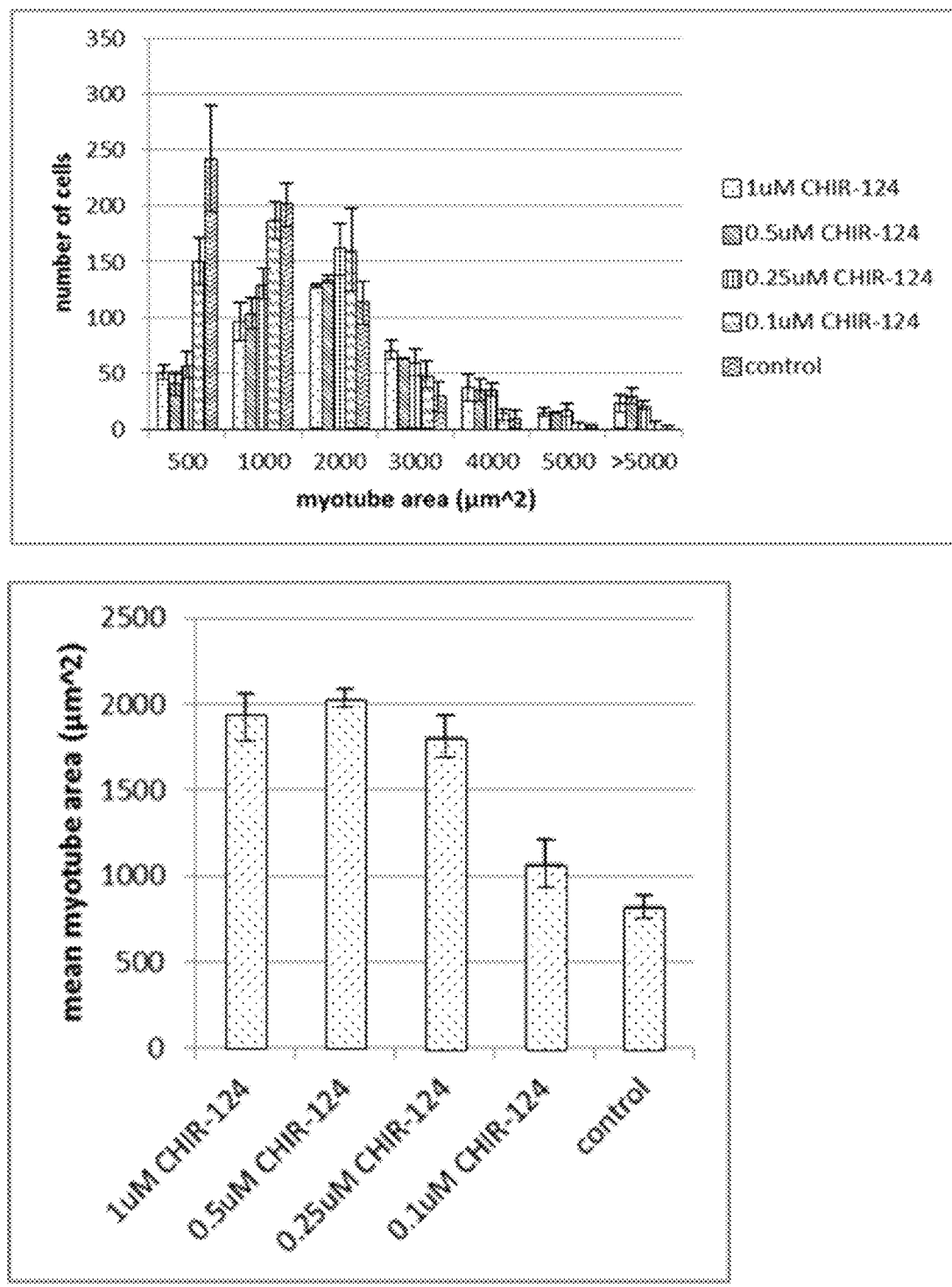
Figure 11:
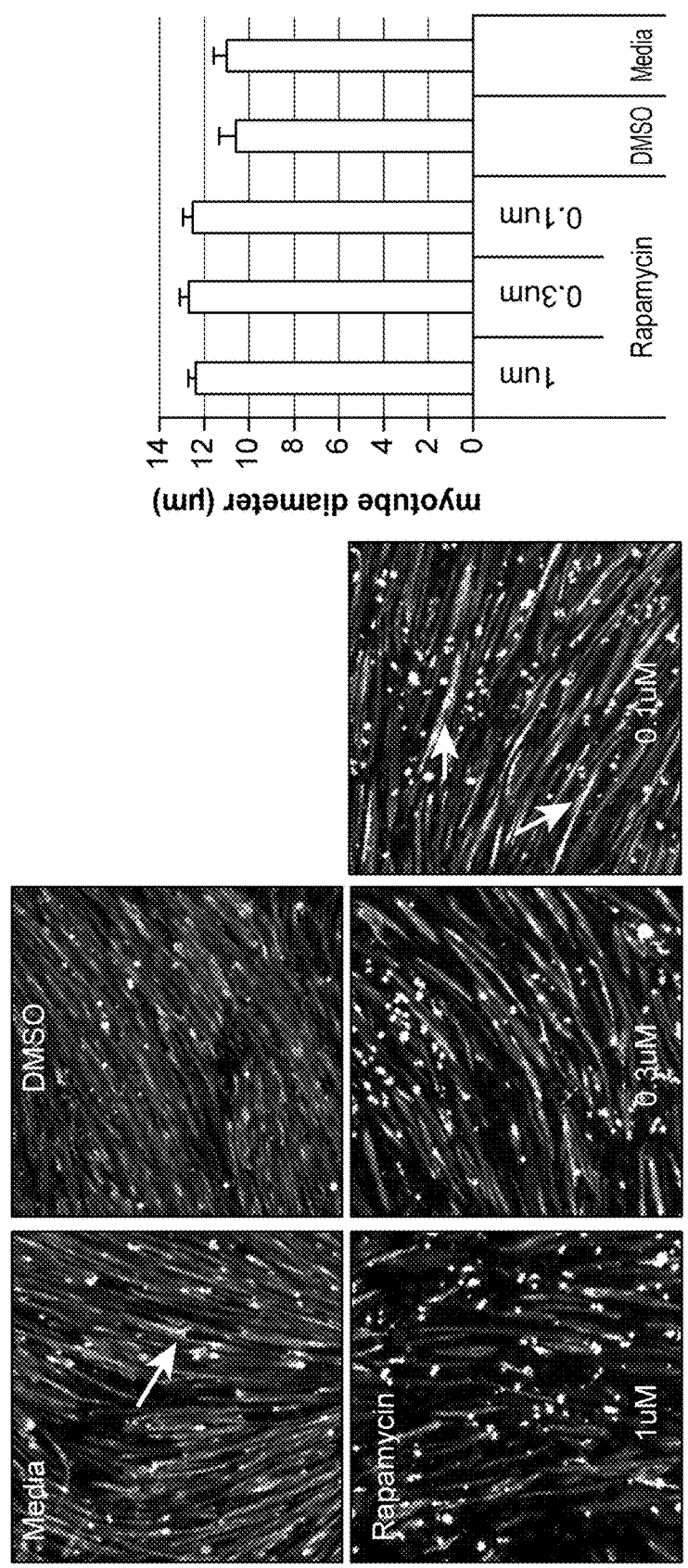
FIG. 11 depicts immunofluorescence images of stem cell-derived myoblasts differentiated into myotubes upon treatment with rapamycin (mTOR inhibitor) tested at different doses in Myotube Medium for 5 days. Cells were fixed and stained with antibodies specific for myosin heavy chain; and nuclei were counterstained with Hoechst. These cells are shown at 20× magnification (upper panel). The diameter of myotubes differentiated in the presence or absence of rapamycin was also determined by image quantitation and represented in a bar graph (lower panel).
Figure 12:
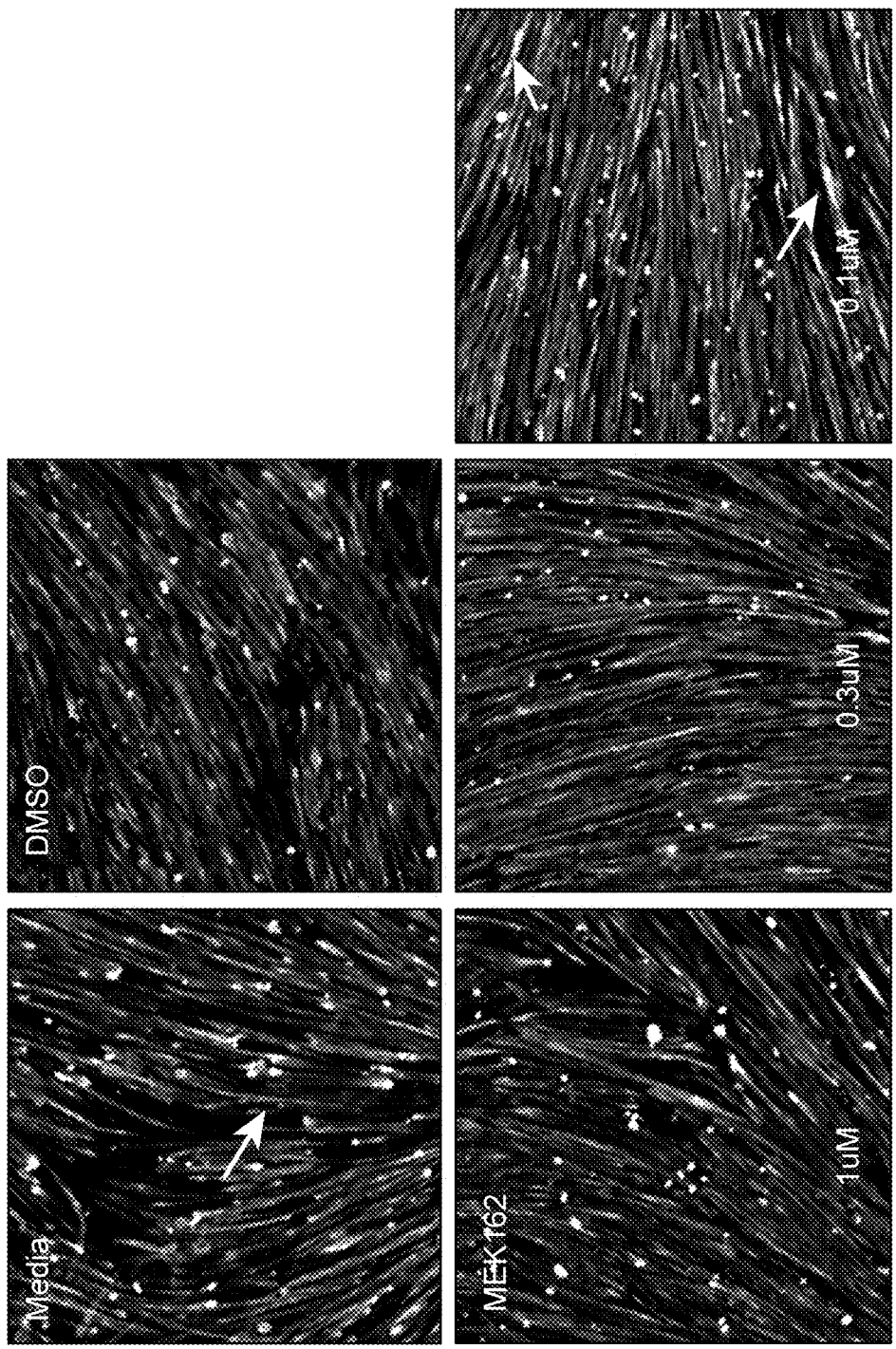
FIG. 12 depicts immunofluorescence images of stem cell-derived myoblasts differentiated into myotubes upon treatment with MEK-162 (MEK inhibitor) tested at different doses in Myotube Medium for 5 days. Cells were fixed and stained with antibodies specific for myosin heavy chain, and nuclei were counterstained with Hoechst. These cells are shown at 20× magnification.
Figure 13:
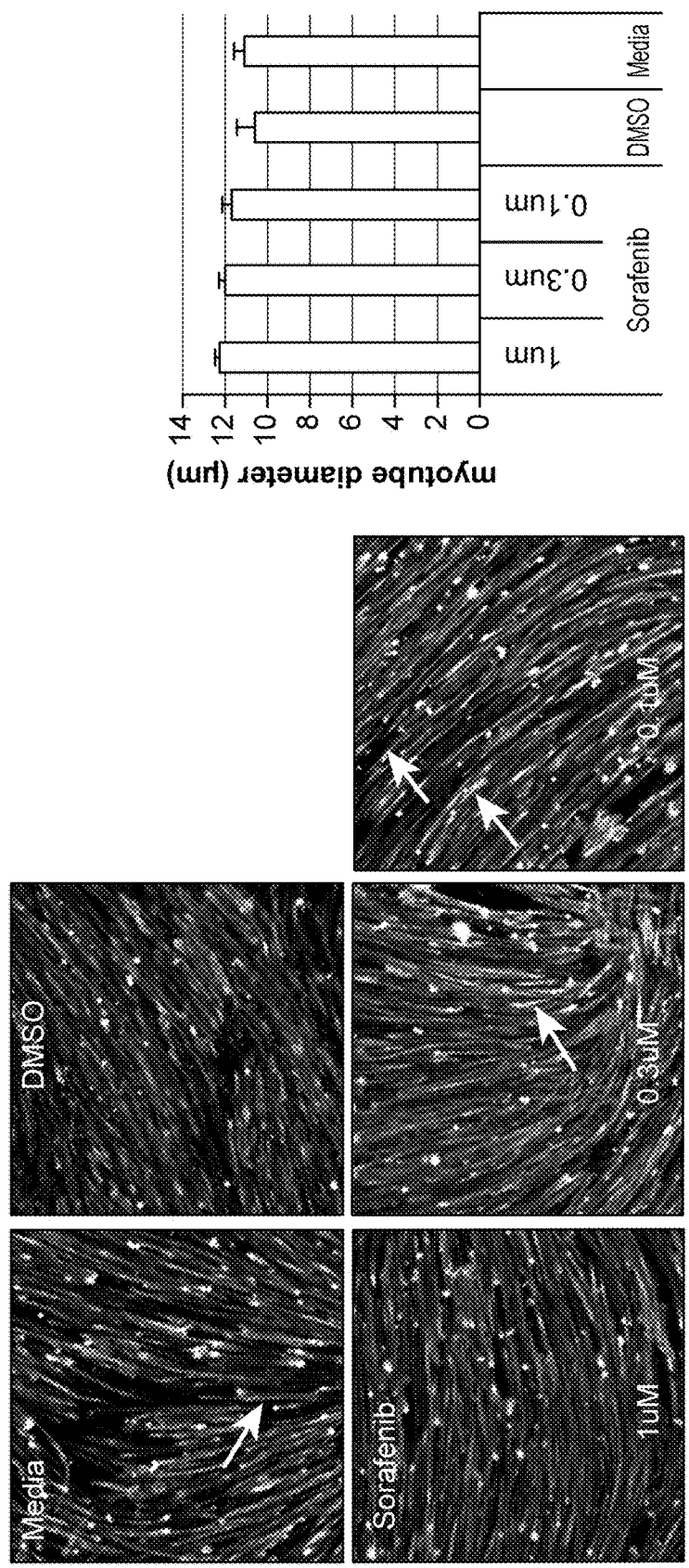
FIG. 13 depicts immunofluorescence images of stem cell-derived myoblasts differentiated into myotubes upon treatment with sorafenib (Raf inhibitor) tested at different doses in Myotube Medium for 5 days and a graphical depiction of myotube diameter for treated and untreated cells. Cells were fixed and stained with antibodies specific for myosin heavy chain and nuclei were counterstained with Hoechst. These cells are shown at 20× magnification (upper panel). The diameter of myotubes differentiated in the presence or absence of sorafenib was also determined by image quantitation and displayed as a bar graph (lower panel).
Figure 14:
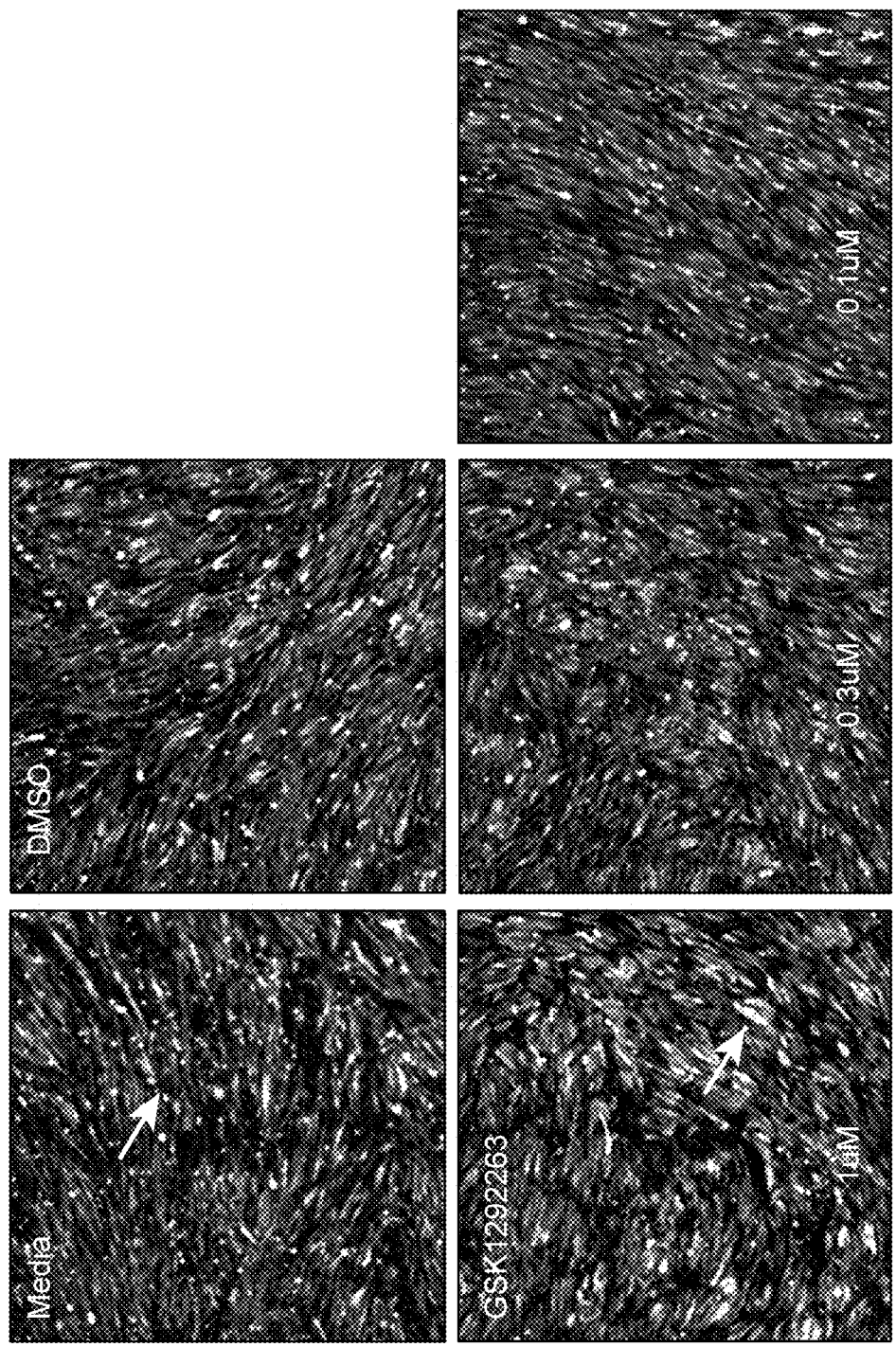
FIG. 14 depicts immunofluorescence images of stem cell-derived myoblasts differentiated into myotubes upon treatment with GSK1292263 (GPR119 agonist) tested at different doses in Myotube Medium for 5 days. Cells were fixed and stained with antibodies specific for myosin heavy chain, and nuclei were counterstained with Hoechst. These cells are shown at 20× magnification.
Figure 15:
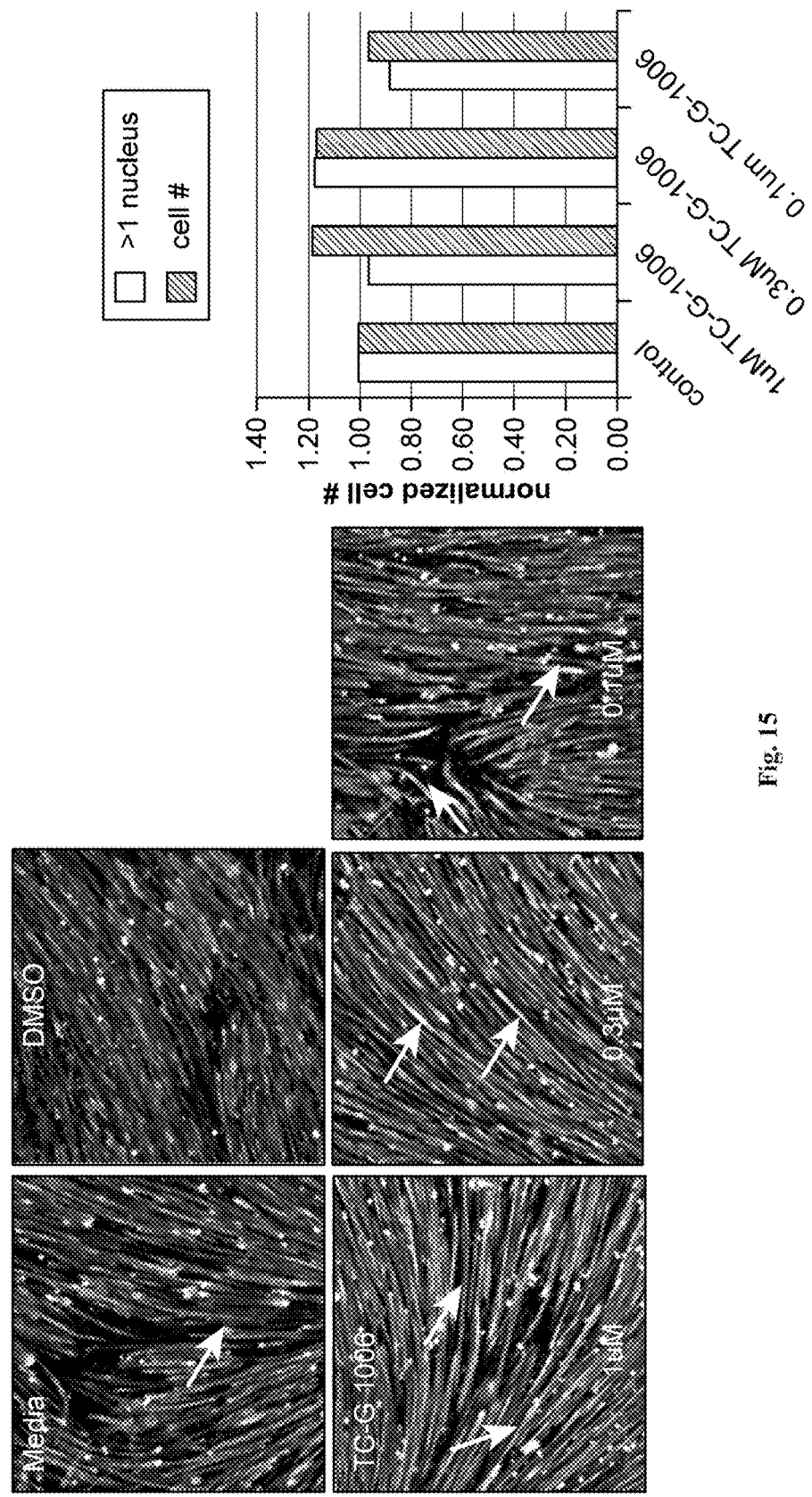
FIG. 15 depicts immunofluorescence images of stem cell-derived myoblasts differentiated into myotubes upon treatment with TC-G 1006 (S1P1 agonist) tested at different doses in Myotube Medium for 5 days (upper panel) and a graphical depiction of the number of cells with more than one nucleus (lower panel). Cells were fixed and stained with antibodies specific for myosin heavy chain and nuclei were counterstained with Hoechst. The cells are shown at 20× magnification.
Figure 16:
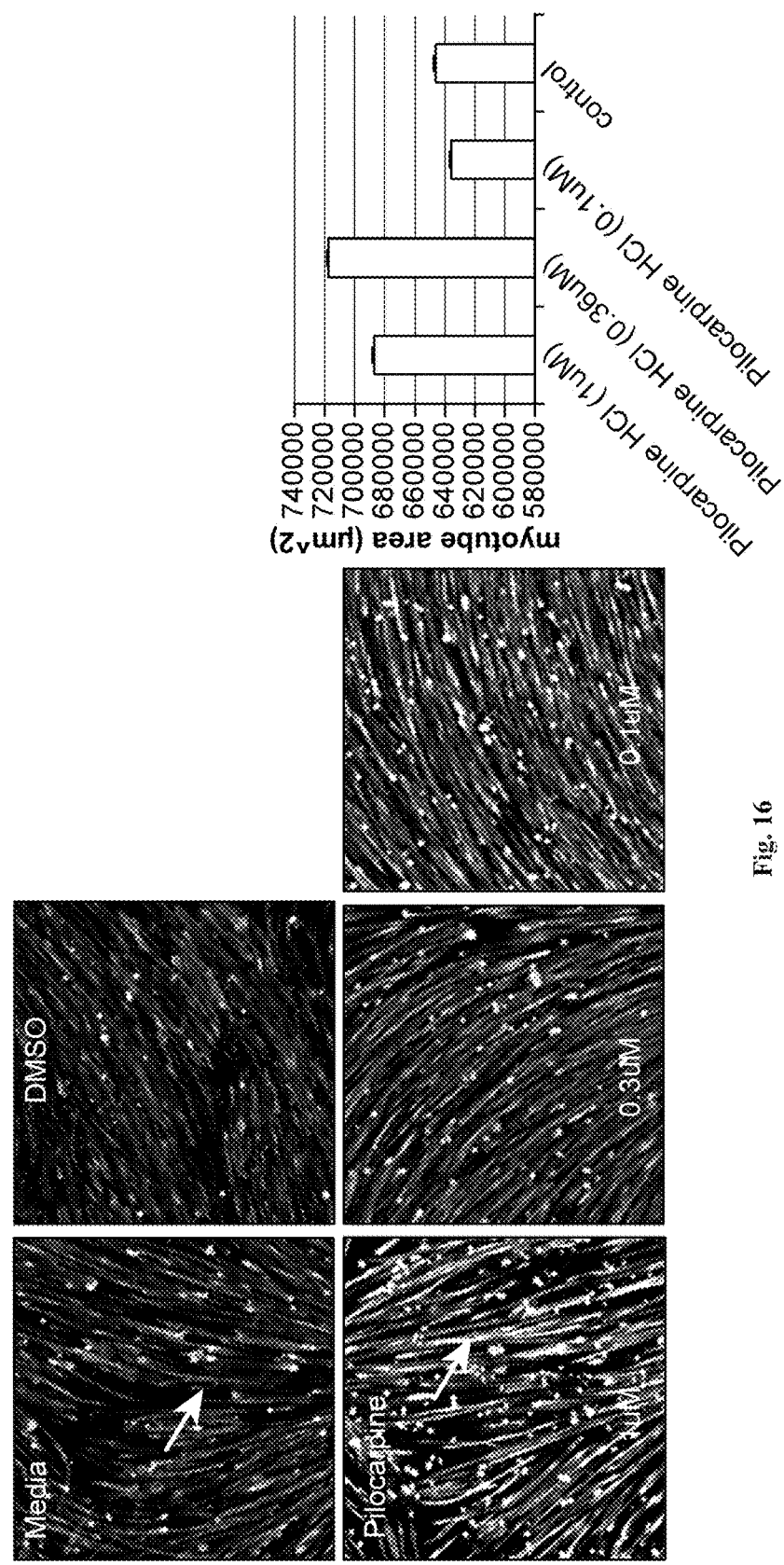
FIG. 16 depicts immunofluorescence images of stem cell-derived myoblasts differentiated into myotubes upon treatment with pilocarpine (nonspecific mAChR agonist) tested at different doses in Myotube Medium for 5 days (upper panel) and a graphical depiction of myotube area of cells treated with three different concentrations of pilocarpine (lower panel). Cells were fixed and stained with antibodies specific for myosin heavy chain, and nuclei were counterstained with Hoechst. These cells are shown at 20× magnification.
Figure 17:
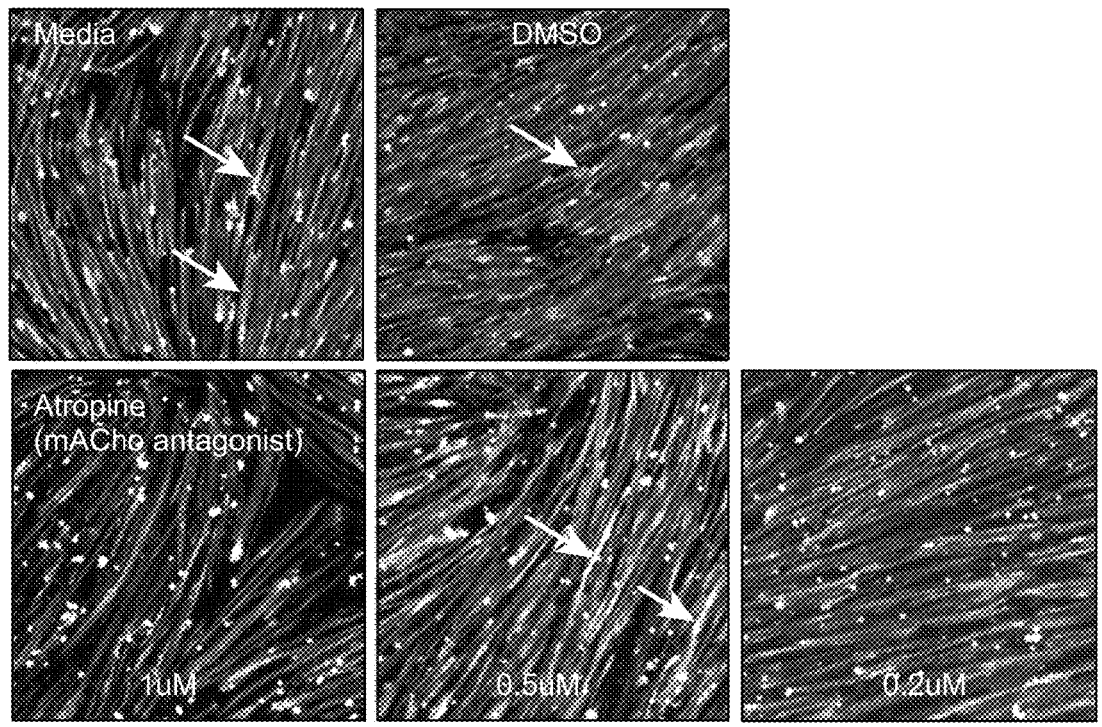
FIG. 17 depicts immunofluorescence images of stem cell-derived myoblasts differentiated into myotubes upon treatment with atropine (mAChR antagonist) tested at different doses in Myotube Medium for 5 days (upper panel) and graphical depictions of total myotube area of cells in the image (lower left panel) and of myotube diameter (lower right panel) for treated and untreated cells. Cells were fixed and stained with antibodies specific for myosin heavy chain and nuclei were counterstained with Hoechst. These cells are shown at 20× magnification.
Figure 17:
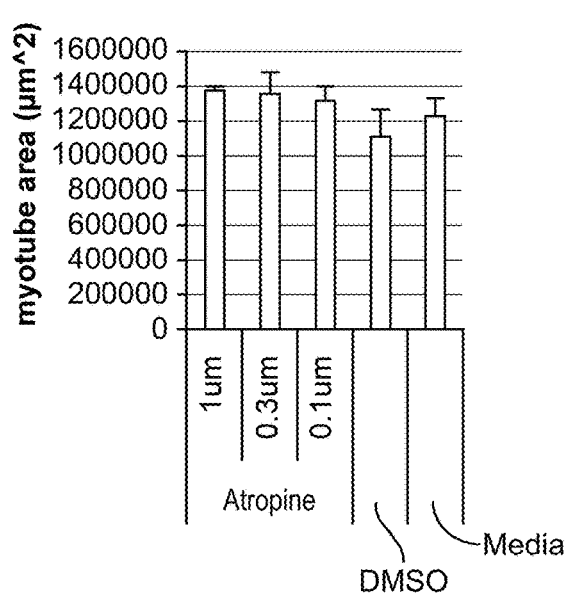
Figure 17:
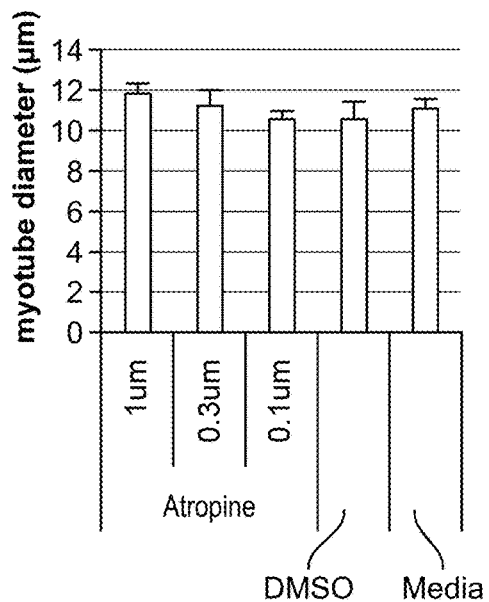
Figure 18:
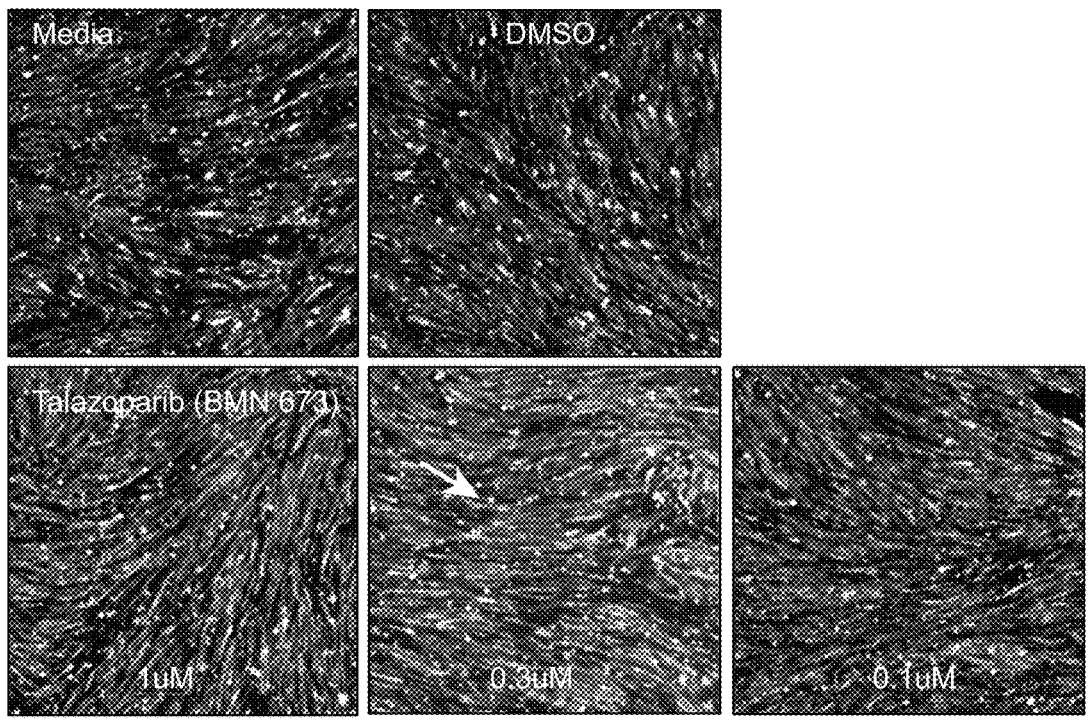
FIG. 18 depicts immunofluorescence images of stem cell-derived myoblasts differentiated into myotubes upon treatment with Talazoparib (PARP inhibitor) tested at different doses in Myotube Medium for 5 days (upper panel) and graphical depictions of total myotube area of cells in the image (lower right panel) and of myotube diameter for treated and untreated cells (lower left panel). Cells were fixed and stained with antibodies specific for myosin heavy chain and nuclei were counterstained with Hoechst. These cells are shown at 20× magnification.
Figure 18:
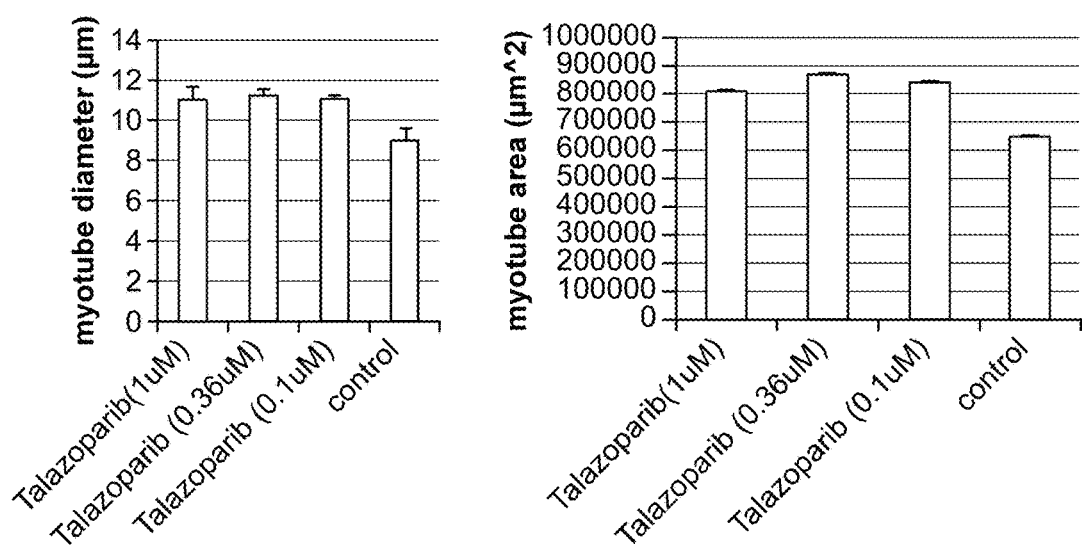

FIGS. 10A, 10B, 10C, 10D, 11, 12, 13, 14, 15, 16, 17, and 18 show the usefulness of particular classes of target inhibitors for enhancing myoblast to myotube differentiation. FIGS. 10A, 10B, 10C, and 10D show that cell cycle or Chk1 inhibition (using CHIR-124) can produce myotubes with mature features. FIG. 11 shows that mTOR inhibition (using rapamycin) can produce myotubes with mature features. FIG. 12 shows that MEK inhibition (using MEK162) can produce myotubes with mature features. FIG. 13 shows that Raf inhibition (using sorafenib) can produce myotubes with mature features. FIG. 14 shows that GPR119 GPCR activation (via application of the agonist GSK1292263) produce myotubes with mature features. FIG. 15 shows that S1P1 GPCR activation (via application of the agonist TC-G 1006) can produce myotubes with mature features. FIG. 16 shows that mAChR GPCR activation (via the agonist pilocarpine) produce myotubes with mature features. FIG. 17 shows that mAChR GPCR inhibition (via the antagonist atropine) produce myotubes with mature features. FIG. 18 shows that PARP inhibition (using talazoparib) can produce myotubes with mature features.

Figure 19:
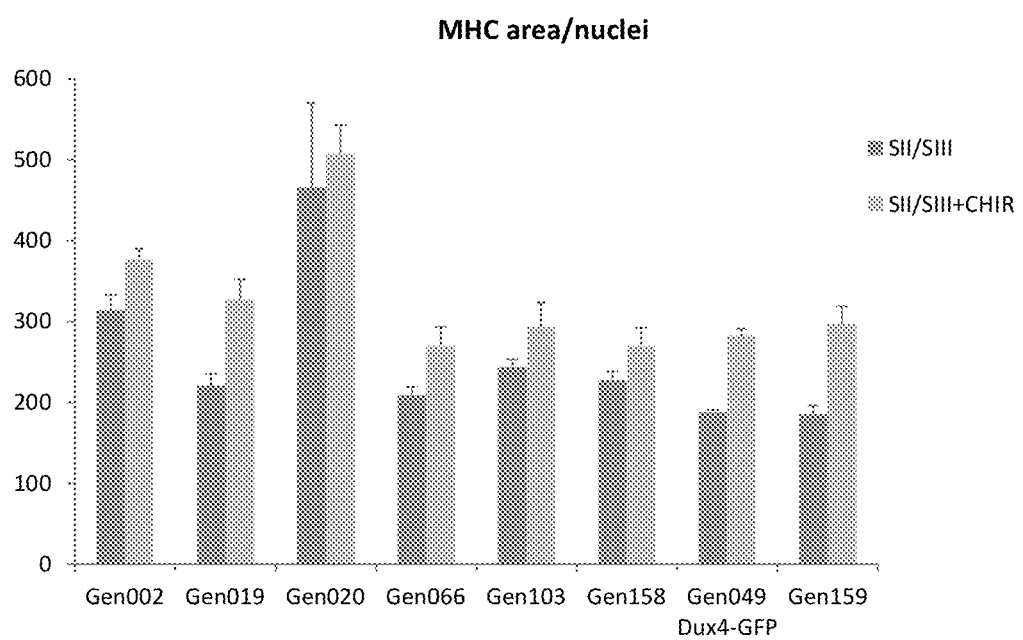
FIG. 19 is a bar graph showing myotube formation from various disease-affected stem cell lines cultured with CHIR-124 (SII/SIII+CHIR) or without CHIR-124 (SII/SIII). Shown is the ratio between area of MHC and nuclei (um$^2$), which is calculated by measuring area per field divided by the number of nuclei within that field. All cell lines tested showed a higher MHC area/nuclei ratio upon the use of CHIR124.
Figure 20:
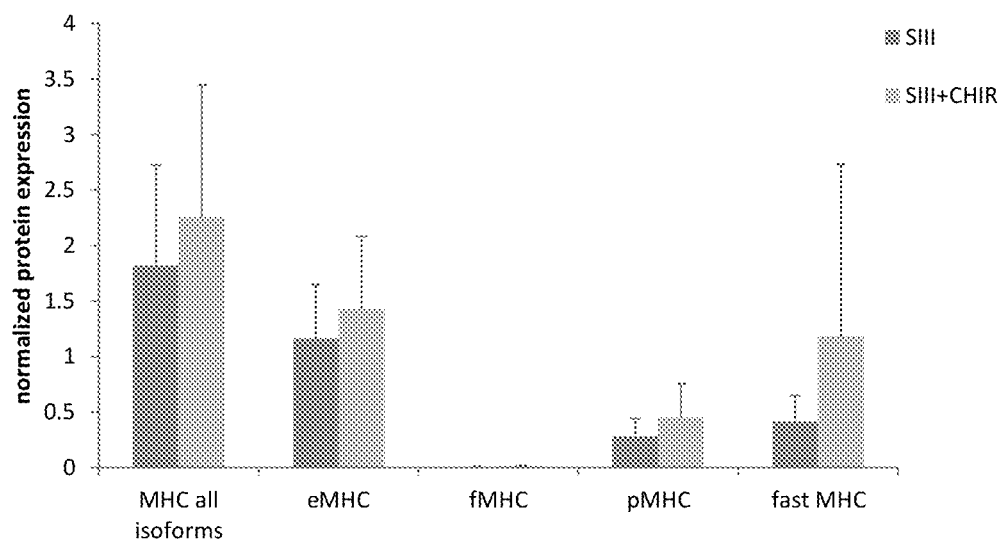
FIG. 20 is a bar graph depicting a western blot-based expression analysis of different myosin heavy chain types expressed in myotubes cultured with CHIR-124 (SII/SIII+CHIR) or without CHIR-124 (SII/SIII). eMHC, embryonic myosin heavy chain (MyH3); fMHC, foetal myosin heavy chain (MyH7); pMHC, perinatal myosin heavy chain (pMHC); fast MHC, fast myosin heavy chain, which is the most mature MHC for myotubes.

FIG. 19 depicts the usefulness of compounds as described herein (here, CHIR-124, a Chk1 inhibitor) for enhancing myotube formation—particularly mature myotube formation—from disease-affected myoblasts. FIG. 19 shows that myoblasts affected with Huntington's disease, myotonic dystrophy type II, spinal muscular atrophy, myotonic dystrophy type I, FSH muscular atrophy and Duchenne muscular dystrophy all show improvements in differentiation when treated with CHIR-124. FIG. 20 shows increased expression of the most mature forms of MHC in the presence of CHIR-124.

In some cases, the compound (e.g., checkpoint inhibitor, CHIR-124) is administered to a subject in combination with the administration of a cell therapy. In some cases, the compound (or a synergistic mixture of compounds) may be administered in combination with the introduction of a precursor to a myotube (e.g., myoblast cell, myoblast-like cell, immature myotube, satellite cell, satellite-like cell, stem cell, or other muscle-cell precursor). In some cases, the compound may be introduced to a subject in combination with administration of mature or immature myotubes or myotube-like cells provided herein.

In other examples, mature myotubes may be formed from satellite cells or satellite-like cells differentiated from disease-specific pluripotent stem cells such as an embryonic stem cell identified as carrying a mutation associated with a genetic disease or disorder or an induced pluripotent stem that is either (a) obtained from a subject with a genetic mutation or (b) genetically-altered to carry a genetic mutation. These disease-specific stem cells may then be differentiated into disease-specific satellite cells or satellite-like cells and further differentiated into disease-specific myoblast or myoblast-like cells and mature myotubes. Disease-specific myotubes may be used for drug screening and other clinical applications.

III. Subjects to be Treated

The myotubes, myotube-like cells, compounds for forming mature myotubes, or a combination of transplanted myotube precursor cells along with compounds provided herein may be used to treat or ameliorate the symptoms of a wide variety of subjects. Subjects who may generally benefit from the cells and methods provided herein are subjects with a muscular disease or disorder that affects muscle function, tone or physiology. In some cases, the subjects may have a genetic disease (e.g., Huntington's disease, muscular dystrophy); in some cases, the subjects may have an acquired disorder (e.g., muscle atrophy caused by inactivity). Additionally, subjects with muscular dystrophy may have multi-system disorders with manifestations in body systems including the heart, gastrointestinal system, nervous system, endocrine glands, eyes and brain. Subjects in need of treatment can include those who have undergone muscle strain or injury. The muscle injury may be the result of a traumatic event, such as a slip or fall during an activity such exercise. Exemplary diseases or disorders that may be exhibited by the subjects treated using the methods disclosed herein include: muscular dystrophy, Huntington's disease, Merosin deficiency 1A, nemaline myopathy, and Spinal Muscular Atrophy (SMA). Examples of muscular dystrophies that may be treated or improved by the disclosed cells include Becker, congenital, facioscapulohumeral (FSH), myotonic (type I and II), oculopharyngeal, distal, Duchenne muscular dystrophy, and Emery-Dreifuss muscular dystrophy. Duchenne and Becker muscular dystrophies are caused by a mutation of a gene located on the X chromosome and predominantly affect males, although females can sometimes have severe symptoms as well. Subjects in need of treatment may also include subjects experiencing muscle atrophy or wasting, including muscle atrophy that may occur as a result of cachexia or wasting syndrome. Cachexia may be accompanied by muscle atrophy, loss of weight, fatigue, weakness, and significant loss of weight. The methods of treatment provided herein may help reverse some of these symptoms, particularly muscle atrophy and weakness. Subjects with cachexia may include patients with cancer, acquired immune deficiency syndrome (AIDS), chronic obstructive lung disease, multiple sclerosis, congestive heart failure, tuberculosis, familial amyloid polyneuropathy, gadolinium poisoning, mercury poisoning (acrodynia) and hormonal deficiency.

In some cases, subjects in need of treatment are patients with sarcopenia, or loss of muscle mass or function associated with the aging process. The treatments provided herein may help reverse or improve the sarcopenia, or loss of muscle mass or function; in some cases, the treatments provided herein help prevent the sarcopenia, or loss of muscle mass or function, from worsening over time.

Subjects who may benefit from the disclosed compositions and methods include subjects who desire prophylactic treatment, such as subjects at risk of loss of muscle mass. Such subjects may include those about to undergo treatment regimens that can reduce muscle mass, such as chemotherapy. Such subjects also can include subjects who have been immobilized or partially immobilized for periods of time sufficient to reduce muscle mass, such as due to unconsciousness or wearing an immobilizing cast. Examples of subjects may include those who have recently undergone surgery which has damaged or reconnected muscle tissue. Examples of subjects may also include those born without a specific muscle or in need of a muscle graft. Subjects may also be subjects seeking improved muscle mass or function for cosmetic reasons or to improve athletic performance.

Subjects in need of myotube or myotube-like cell transplants or treatment with compounds that stimulate formation of mature myotubes may include men or women. Such subjects may be of a range of ages, which may include >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years. Subjects may have differing genetic backgrounds, including different racial groups or genetically admixed populations.

IV. Generating Myotubes or Myotube-Like Cells

The methods provided herein generally involve generating mature myotubes or mature myotube-like cells from myoblasts or myoblast-like cells, often by contacting the myoblasts or myoblast-like cells with one or more compounds to promote the generation of the mature myotubes or mature myotube-like cells. The methods may also include methods of generating the myoblasts or myoblast-like cells from satellite cells or satellite-like cells, as well as methods of producing the satellite cells or satellite-like cells. This disclosure also provides compositions, including compositions comprising one or more myotubes or myotube-like cells.

A. Myoblasts or Myoblast-Like Cells Capable of Differentiation into Mature Myotubes or Myotube-Like Cells The myoblasts or myoblast-like cells used to generate the myotubes or myotube-like cells provided herein may be obtained by any method known in the art. In some cases, myoblasts or myoblast-like cells may be generated in vitro according to the methods described further herein, or by another method. In some cases, primary myoblasts are used in the methods provided herein. In some cases, myoblasts derived from primary myoblasts are used in the methods provided herein. Primary myoblasts typically may be obtained directly from mammalian subjects or cadavers, such as by surgical removal of myoblasts from the subject or cadaver.

After myoblasts or myoblast-like cells have been generated or obtained, they may be expanded. Myoblasts or myoblast-like cells may be expanded by seeding the cells at a range of densities so that the cells are approximately 25-80% confluent. For example, the myoblasts or myoblast-like cells may be seeded at a density such that the cells are about 25% confluent, about 30% confluent, about 35% confluent, about 40% confluent, about 45% confluent, about 50% confluent, about 55% confluent, about 60% confluent, about 65% confluent, about 70% confluent, about 75% confluent, or about 80% confluent. In some examples, the cells may be seeded at a density of from about $1.5 \times 10^3$ cells/cm$^2$ to about $10^4$ cells/cm$^2$; from about $2 \times 10^3$ cells/cm$^2$ to about $10^4$ cells/cm$^2$; from about $3 \times 10^3$ cells/cm$^2$ out $10^4$ cells/cm$^2$ from about $4 \times 10^3$ cells/cm$^2$ to about $10^4$ cells/cm$^2$; or from about $10^3$ cells/cm$^2$ to about $9 \times 10^3$ cells/cm$^2$. In some embodiments, the cells may be seeded at a density greater than $10^4$ cells/cm$^2$, e.g., from about $1.25 \times 10^4$ cells/cm$^2$ to about $3 \times 10^4$ cells/cm$^2$. In some preferred embodiments, the myoblasts or myoblast-like cells are cultured in a monolayer.

Myoblasts or myoblast-like cells may be cultured directly on tissue culture-grade plastic as a substrate. Alternatively, myoblasts or myoblast-like cells may be cultured on a coated substrate (e.g., substrate coated with fibronectin, extracellular matrix, collagen, gelatin, matrigel, geltrex or laminin, as well as combinations thereof). The concentrations of the substances used to coat the substrate may be about 5 μg/ml, 10 μg/ml, 20 μg/ml, 40 μg/ml, 60 μg/ml, 80 μg/ml, 100 μg/ml, or 200 μg/ml, or 1 mg/ml, or other concentrations as appropriate. In some cases, myoblasts or myoblast-like cells may be cultured on a substrate coated with collagen type I.

Myoblasts or myoblast-like cells may be grown in cultures in a 37° C., 5% $CO_2$ incubator at an oxygen level equal to that of the atmosphere. In some cases, myoblasts or myoblast-like cells may be grown in cultures in a 37° C., 5% $CO_2$/5% $O_2$ incubator (e.g., under hypoxic conditions). Myoblasts or myoblast-like cells may be grown in cultures for at least about 1 day, 2 days, 3 days, 4 days, 5 days, 6 days, 7 days, 8 days, 9 days, 10 days, 11 days, 12 days, 13 days, 14 days, 3 weeks, 4, weeks, 5 weeks, or even longer.

Myoblasts or myoblast-like cells may be grown in myotube medium (e.g., Genea Biocells Myotube Medium). In some cases, myotube medium may be serum-free. For example, the myotube medium may contain DMEM, MCDB or RPMI 1640 medium.

In some cases, the myotube medium may comprise serum. For example, the serum may be horse serum, bovine serum, calf serum, or other serum known in the art. In some cases, the myotube medium may contain at least 0.5%, 1%, 2%, 3%, 5%, 7%, 10%, 15%, or 20% serum (e.g., horse serum). In some cases, the myotube medium may contain less than 0.5%, 1%, 2%, 3%, 5%, 7%, 10%, 15%, or 20% serum, e.g., the myotube medium may contain 0.5%-8% serum (e.g., horse serum). In some particular cases, myotube medium may contain 5% horse serum (Thermo fisher Scientific Life Sciences).

In some cases, myotube medium may be supplemented with other factors, including, but not limited to, insulin, oncostatin, necrosulfonamide and/or ascorbic acid. In some cases, myotube medium may contain insulin in a concentration of at least about 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 12 μg/ml, 18 μg/ml, 19 μg/ml, or 20 μg/ml. In some cases, myotube medium may contain oncostatin in a concentration of at least about 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 21 μg/ml, 22 μg/ml, 23 μg/ml, 24 μg/ml, 25 μg/ml, 26 μg/ml, 27 μg/ml, 28 g/ml, 29 g/ml, or 30 μg/ml. In some cases myotube medium may contain necrosulfonamide at a concentration of at least about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, or 100 nM. In some cases, myotube medium may contain ascorbic acid in a concentration of at least about 10 μM, 25 μM, 50 μM, 75 μM, 100 μM, 125 μM, 150 μM, 175 μM, 200 μM, 225 μM, 250 μM, 275 μM, 300 μM, 325 μM, 350 μM, 375 μM, or 400 μM.

The myoblasts may be cultured in the same myotube medium over time, often with medium changes. In some cases, the myotube medium may be changed or added to daily. In some cases, the myotube medium may be changed or added to every other day, twice-a-week, once-a-week, every two weeks, every three weeks or longer.

B. Contacting Myoblasts with Compounds

The methods provided herein include contacting myoblasts and myoblast-like cells with one or more compounds by culturing the cells in myotube medium supplemented with the one or more compounds. In some cases, the methods provided herein include administering one or more compounds to a subject in order to promote myotube production, particularly production of mature myotubes in the subject. In such cases, a subject's cells may be contacted in vivo with one or more compounds described herein.

Myoblasts and myoblast-like cells may be contacted with compounds that include but are not limited to small molecules, peptides, peptoids, antisense oligonucleotides, RNAs and aptamers. Myoblasts and myoblast-like cells may be contacted with one or more compounds that are known or suspected to target molecules in various signaling pathways, including but not limited to cell cycle signaling pathways, DNA repair pathways, MAPK signaling pathways, PI3K/Akt signaling pathways, mTOR signaling pathways, G-protein coupled receptor (GPCR) pathways, and muscarinic acetylcholine receptor (mAChR) pathways.

In some cases the compound or compounds that contact the myoblast or myoblast-like cells may include kinase inhibitors that target kinase enzymes involved in cell cycle signaling and DNA repair pathways. The compound or compounds may include inhibitors of cyclin-dependent kinases (CDK). The compound or compounds may include but are not limited to CDK inhibitors palbociclib, SNS-032, dinaciclib, K03861, JNJ-7706621, AZD5438, PHA-793887, BS-181, abemaciclib, BMS-265246, PHA-767491, milciclib, R547, ribociclib (LEE011), P276-00, LDC000067, and/or Ro-3306. The compound or compounds may include inhibitors of Checkpoint Kinase 1 (Chk1), including but not limited to MK-8776, AZD7762, LY2603618, CHIR-124, and/or PF-477736. The compound or compounds may include inhibitors of the kinase Akt1, including, but not limited to A-674563. The compound or compounds may include inhibitors of cell division cycle (CDC) kinases or CDC-like (Clk) kinases, including, but not limited to: TG003, ML167, and/or XL413. The compound or compounds may include inhibitors of the aurora cell cycle kinases, including but not limited to: alisertib, barasertib, ZM447439, MLN8054, danusertib, Aurora-A Inhibitor I, SNS-314, MK-5108, PHA-680632, CYC116, PF-03814735, AMG-900, and/or GSK1070916.

In some cases the compound or compounds that contact the myoblast or myoblast-like cells may include poly ADP-ribose polymerase (PARP) inhibitors. The compound or compounds may include but are not limited to the PARP inhibitors olaparib, veliparib, rucaparib, iniparib, talazoparib, AG 14361, INO-1001, A966492, PJ 34, UPF 1069, AZD2461, ME0328, and/or NU1025.

In some cases the compound or compounds that contact the myoblast or myoblast-like cells may include kinase inhibitors that target kinase enzymes or receptors involved in PI3K/Akt, mTOR, and MAPK signaling pathways. The compound or compounds may include but are not limited to the kinase inhibitors BEZ235 (dactolisib), omipalsib, LY2228820, AZD8055, BI-D1879, danusertib, MK2206, and/or refametinib. The compound or compounds may include but are not limited to the IGF-1 receptor inhibitor BMS754807.

In some cases the compound or compounds that contact the myoblast or myoblast-like cells may include modulators of GPCR signaling. The compounds may include modulators of GPR119. The compounds may include but are not limited to the GPR119 agonists APD597, APD668, PSN632408, MBX-2982, and GSK1292263. The compounds may include modulators of the cannabinoid receptors CB1, CB2 and/or GPR55, including but not limited to Org 27569, WIN 55,212-2, AM251, CID 16020046, Abn- CBD, O-1602, and/or noladin ether. The compounds may include modulators of any GPCR or GPCR-mediated signaling molecule.

In some cases the compound or compounds that contact the myoblast or myoblast-like cells may include modulators of muscarinic acetylcholine receptors (mAChR). The compounds may include mAChR agonist and mAChR antagonists, including but not limited to: MK 7622, pilocarpine, methacholine, cevimeline, arecholine, bethanechol, xanomeline, homatropine, benzetimide, camylofin, atropine, propantheline, clidinium, pipenzolate, and/or scopolamine. The compounds may include modulators of any mAChR or mAChR-mediated signaling molecule.

In some cases, the compound or compounds that contact the myoblasts or myoblast-like cells may modulate activity of a molecule or molecules involved in various signaling pathways. The compound or compounds may modulate activity of a molecule or molecules involved in, but not limited to, Wnt/Fzd/beta-catenin signaling pathways, telomere structure and telomerase activity pathways, cytoskeleton structure signaling pathways, JAK/STAT signaling pathways, apoptosis signaling pathways, metabolic signaling pathways, and ubiquitin signaling pathways.

In some cases, the compound or compounds that contact the myoblasts or myoblast-like cells may activate or inhibit enzymes. The compound or compounds may activate or inhibit enzymes including, but not limited to, kinases, phosphatases, lipases, ligases, glycosylases, hydrolases, carboxylases, transferases, and oxidoreductases.

According to the methods provided herein, the compound or compounds may be in contact with the myoblast or myoblast-like cells at various concentrations. In some examples the compound or compounds that contact the myoblast or myoblast-like cells may be present in the myotube medium at a concentration of about 10 pM, about 50 pM, about 100 pM, about 500 pM, about 1 nM, about 5 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1 µM, about 2 µM, about 3 µM, about 4 µM, about 5 µM, about 10 µM, about 20 µM, about 30 µM, about 40 µM, about 50 µM, about 60 µM, about 70 µM, about 80 µM, about 90 µM, about 100 µM or greater than 100 µM. In some examples the compound or compounds that contact the myoblast or myoblast-like cells may be present in the myotube medium at a concentration of less than about 10 pM, less than about 50 pM, less than about 100 pM, less than about 500 pM, less than about 1 nM, less than about 5 nM, less than about 10 nM, less than about 20 nM, less than about 30 nM, less than about 40 nM, less than about 50 nM, less than about 60 nM, less than about 70 nM, less than about 80 nM, less than about 90 nM, less than about 100 nM, less than about 200 nM, less than about 300 nM, less than about 400 nM, less than about 500 nM, less than about 600 nM, less than about 700 nM, less than about 800 nM, less than about 900 nM, less than about 1 µM, less than about 2 µM, less than about 3 µM, less than about 4 µM, less than about 5 µM, less than about 10 µM, less than about 20 µM, less than about 30 µM, less than about 40 µM, less than about 50 µM, less than about 60 µM, less than about 70 µM, less than about 80 µM, less than about 90 µM, or less than about 100 µM. In some examples the compound or compounds that contact the myoblast or myoblast-like cells may be present in the myotube medium at a concentration of between at least 60 nM and at most 5 µM, at least 10 nM and at most 50 µM, at least 60 pM and at most 90 µM, or other range of concentrations.

According to the methods provided herein, the compound or compounds may contact the myoblast or myoblast-like cells for various periods of time. In some examples the compound or compounds may contact the myoblast or myoblast-like cells for about 1 day, about 1.5 days, about 2 days, about 2.5 days, about 3 days, about 3.5 days, about 4 days, about 4.5 days, about 5 days, about 5.5 days, about 6 days, about 6.5 days, about 7 days, about 7.5 days, about 8 days, about 8.5 days, about 9 days, about 9.5 days, about 10 days, or greater than 5 days, greater than 7 days, greater than 10 days, greater than 14 days, greater than 20 days, greater than 25 days, greater than 30 days, greater than 35 days, or more. In some examples the compound or compounds may contact the myoblast or myoblast-like cells for less than about 1 day, less than about 1.5 days, less than about 2 days, less than about 2.5 days, less than about 3 days, less than about 3.5 days, less than about 4 days, less than about 4.5 days, less than about 5 days, less than about 5.5 days, less than about 6 days, less than about 6.5 days, less than about 7 days, less than about 7.5 days, less than about 8 days, less than about 8.5 days, less than about 9 days, less than about 9.5 days, less than about 10, less than about 2 weeks, less than about 2.5 weeks, less than about 3 weeks, less than about 4 weeks, or other amount of time.

According to the methods provided herein, the compound or compounds may have a half maximal effective concentration ($EC_{50}$) of less than 50 µM. In some examples, the compound or compounds may have an $EC_{50}$ of less than about 50 µM, less than about 40 µM, less than about 30 µM, less than about 20 µM, less than about 15 µM, less than about 10 µM, less than about 5 µM, or less than about 1 µM. In a preferred embodiment, the compound or compounds have an $EC_{50}$ of less than about 5 µM.

Myotubes or myotube-like cells generated according to the methods provided herein may be detected by any method known in the art. For example, myotubes or myotube-like cells may be detected by assaying expression of myotube protein markers using immunofluorescence. Myotubes or myotube-like cells may be detected by incubating fixed cells antibodies that bind to one or more myotube protein markers, including, but not limited to Myogenin, α-dystrophin, MF20, and skMHC. Myotubes or myotube-like cells may be detected by incubating fixed cells with stains that identify organelles or other cell components (e.g., Hoechst stain to identify nuclei). Myotubes or myotube-like cells that have been fixed and stained may be detected by imaging according to any method known in the art. In some cases, myotubes or myotube-like cells that have been fixed and stained may be detected by imaging with a high content analysis system (e.g., IN Cell Analyzer 6000 imager and Developer Toolbox software).

Myotubes or myotube-like cells generated according to the methods provided herein may further be detected by assaying for mRNA transcript of genes encoding myotube protein markers. Myotubes or myotube-like cells may be detected by assaying for mRNA transcript using methods including, but not limited to, RT-PCR, RNA sequencing, cDNA sequencing, and in situ hybridization.

Mature myotubes or myotube-like cells generated by the methods provided herein may be selected for use in methods of cell therapy and drug screening provided further herein. Mature myotubes or myotube-like cells may be selected for use in cell therapy and/or drug screening by morphological features of mature myoblasts (e.g., long, branched myotubes with many nuclei and large diameters), gene expression data, or other methods known in the art.

i) Chk1 Inhibitors

In some cases, checkpoint inhibitors, particularly Chk1 inhibitors, are used to enhance or promote production of mature myotubes, as described herein (either in vitro or in vivo). In some cases, the Chk 1 inhibitor is added to a culture medium to promote mature myotube formation in vitro. In some cases, the Chk 1 inhibitor is administered to a subject to promote mature myotube formation in vivo. Chk1 inhibitors may have different chemical structures or different scaffolds. In some embodiments, a Chk1 inhibitor as described herein is a quinolinone Chk1 inhibitor, such as CHIR-124. In some embodiments, CHIR-124 is administered via a suitable method to achieve a local concentration of about 0.10 μM to about 1 μM (e.g., 0.25 μM, 0.50 μM) to enhance or promote production of mature myotubes in vitro or in vivo. In some embodiments, CHIR-124 is administered in a 100 mg dose once daily in a human to enhance or promote production of mature myotubes. In some embodiments, CHIR-124 is administered in a 50-75 mg dose twice daily in a human to enhance or promote production of mature myotubes. Synthesis of quinolinone Chk1 inhibitors has been described elsewhere, e.g. in Li et al. Bioorg Med Chem Lett. 2006 Jun. 15; 16(12):3121-4 and in U.S. Pat. Nos. 7,825,132B2, 7,838,527B2, 7,470,709B2, and US 20050256157A1. In some embodiments, a Chk1 inhibitor as described herein is a quinolinone Chk1 inhibitor according to formula (I):

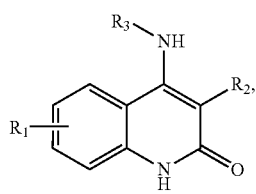

(I)

or a salt thereof, wherein
R1 is selected from methyl, fluoro, chloro, trifluoromethyl, and difluoromethyl;
R2 is selected from benzimidazolyl, benzoxazolyl, benzothiazolyl, 3H-indolyl, benzofuryl, benzothiophenyl, and 1H-indenyl; and
R3 is selected from quinuclidinyl and 1,4-diazabicyclo[2.2.2]octanyl.

In some embodiments, a Chk1 inhibitor as described herein is a quinolinone Chk1 inhibitor according to formula (II):

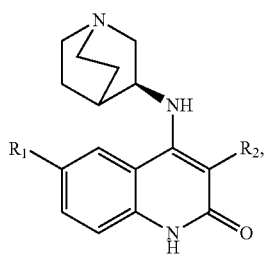

(II)

or a salt thereof, wherein
R1 is selected from methyl, halogen, and halomethyl; and
R2 is a 5+6 bicyclic fused ring system containing 0-4 heteroatoms independently selected from O, S or N.

In some embodiments, a Chk1 inhibitor as described herein is a quinolinone Chk1 inhibitor according to formula (III):

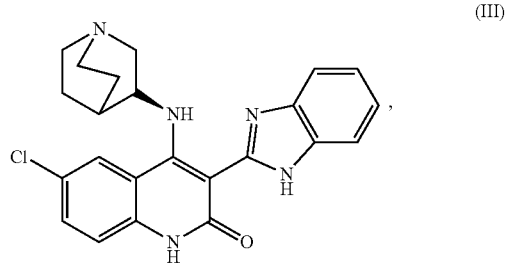

(III)

or a salt thereof (CHIR-124).

In some embodiments, Chk1 inhibitors are not quinolinones. Other cases of scaffolds or exemplary molecules that inhibit Chk1 include pyrazolo[1,5-a]pyrimidines (e.g. MK-8776/SCH900776), thiophenecarboxamide ureas (e.g. AZD7762), pyrizinyl ureas (e.g. LY2603618) and PF 477736.

ii) mTOR Inhibitors

In some cases, mTOR inhibitors, particularly macrolide mTOR inhibitors (e.g. rapamycin), are used to enhance or promote production of mature myotubes (either in vitro or in vivo), as described herein. In some cases, the mTOR inhibitor is added to a culture medium to promote mature myotube formation or generation in vitro. In some cases, the mTOR inhibitor is administered to a subject to promote mature myotube formation in vivo. In some embodiments, an mTOR inhibitor as described herein is a macrolide mTOR inhibitor (e.g. rapamycin) according to formula (IV):

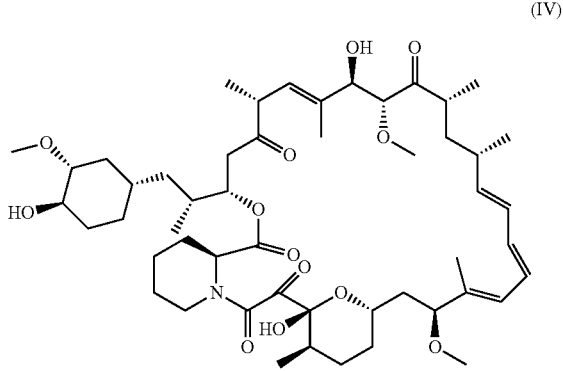

(IV)

iii) Raf Inhibitors

In some cases, Raf inhibitors, particularly benzyl urea Raf inhibitors (e.g. Sorafenib), are used to enhance or promote production of mature myotubes (either in vitro or in vivo), as described herein. In some cases, the Raf inhibitor is added to a culture medium to promote mature myotube formation in vitro. In some cases, the Raf inhibitor is administered to a subject to promote mature myotube formation in vivo. In some embodiments, a Raf inhibitor described herein is a benzyl urea Raf inhibitor (e.g. Sorafenib) according to formula (V):

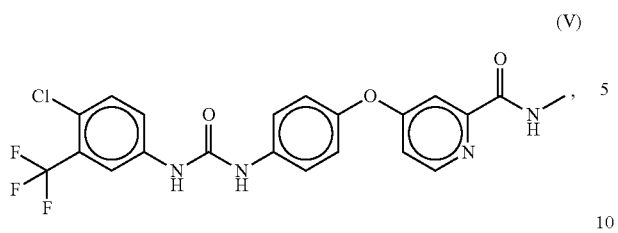
(V)

or a salt thereof.

iv) GPCR Agonists

In some cases, GPCR agonists, particularly agonists of GPR119, S1P1, or mAChR (e.g. GSK1292263, TC-G1006, or pilocarpine), are used to enhance or promote production of mature myotubes (either in vitro or in vivo), as described herein. In some cases, the agonists of GPR119, S1P1, or mAChR are added to a culture medium to promote mature myotube formation in vitro. In some cases, the agonists of GPR119, S1P1, or mAChR are administered to a subject to promote mature myotube formation in vivo. In some embodiments, a GPCR agonist as described herein is a GPR119 agonist (e.g. GSK1292263) according to formula (VI):

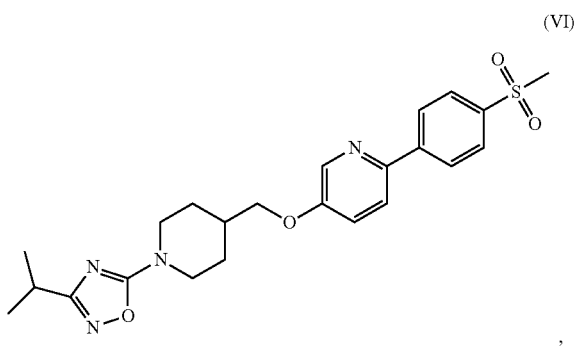 [SMILES: CC(C)c1noc(N2CCC(COc3ccc(-c4ccc(S(C)(=O)=O)cc4)nc3)CC2)n1]
(VI)

or a salt thereof.

In some embodiments, a GPCR agonist as described herein is an S1P1 agonist (e.g. TC-G1006) according to formula (VII):

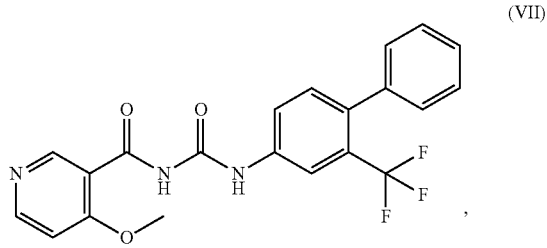 [SMILES: COc1ccncc1C(=O)NC(=O)Nc1ccc(-c2ccccc2)c(C(F)(F)F)c1]
(VII)

or a salt thereof.

In some embodiments, a GPCR agonist as described herein is a mAChR agonist (e.g. pilocarpine) according to formula (VIII):

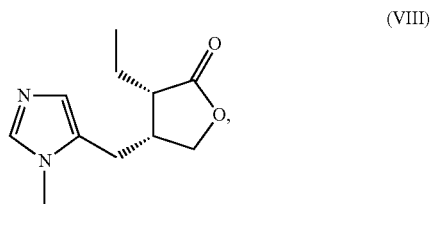
(VIII)

or a salt thereof.

v) GPCR Antagonists

In some cases, GPCR antagonists, particularly agonists of mAChR (e.g. atropine) are used to enhance or promote production of mature myotubes (either in vitro or in vivo), as described herein. In some cases, the GPCR antagonist (e.g., atropine) is added to a culture medium to promote mature myotube formation in vitro. In some cases, the GPCR antagonist (e.g., atropine) is administered to a subject to promote mature myotube formation in vivo. In some embodiments, a GPCR antagonist as described herein is a mAChR antagonist (e.g. atropine) according to formula (IX):

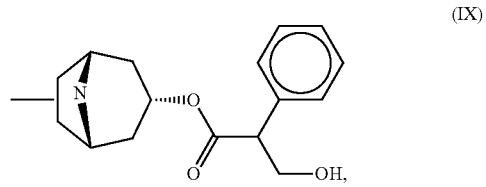
(IX)

or a salt thereof.

vi) PARP Inhibitors

In some cases, PARP inhibitors are used to enhance or promote production of mature myotubes (either in vitro or in vivo), as described herein. In some cases, the PARP inhibitors are added to a culture medium to promote mature myotube formation in vitro. In some cases, the PARP inhibitors are administered to a subject to promote mature myotube formation in vivo. In some embodiments, a PARP inhibitor as described herein is talazoparib, a compound according to formula (X):

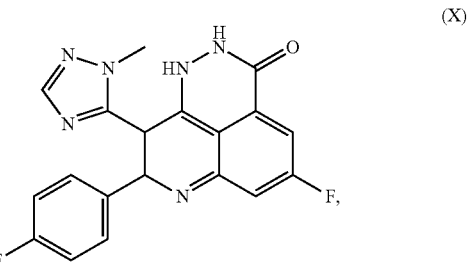
(X)

or a salt thereof.

vii) MEK Inhibitors

In some cases, MEK inhibitors are used to enhance or promote production of mature myotubes (either in vitro or in vivo), as described herein. In some cases, the MEK inhibitors are added to a culture medium to promote mature myotube formation in vitro. In some cases, the MEK inhibitors are administered to a subject to promote mature myotube formation in vivo. In some embodiments, a MEK inhibitor as described herein is MEK162 (binimetinib), a compound according to formula (X):

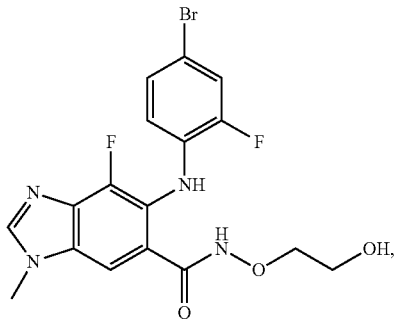

(XI)

or a salt thereof.

C. Features of Myotubes or Myotube-Like Cells Generated by the Methods Provided Herein As used herein, the term "myotube-like cell" refers to any cell that possesses structural or functional features associated with a naturally-occurring myotube (e.g., myotubes within an organism such as a human) but yet also possesses at least one structural or functional feature distinguishing the myotube-like cell from a naturally-occurring myotube. In preferred embodiments, a myotube-like cell is a cell that is (a) produced in vitro from a myoblast or (b) derived from a myotube-like cell, such as cells resulting from proliferation of a myotube-like cell.

As used herein, the term "myotube" refers to a cell that possesses the structural and functional features exhibited by a naturally-occurring myotube, and may or may not possess at least one structural or functional feature that distinguishes it. Naturally-occurring mature myotubes are generally large and branched and have multiple nuclei.

Generally, the myotubes and myotube-like cells produced by the methods provided herein are fibers with various characteristics. The fibers often have striations. They generally have functional sarcomeric organization. For example, they may have periodic distribution of sarcomeric proteins (e.g., Titin, fast MyHC) and may twitch spontaneously. In some cases, they may exhibit a fast-twitch. In some cases, they may exhibit a slow-twitch.

The methods provided herein include generating mature myotubes or myotube-like cells with adult-like morphology, generally indicated by having one or more of the following features (or two or more, or three or more, etc.): elongated morphology, large diameter, high degrees of multi-nucleation and/or branch-like features. In some instances, the adult-like morphology is indicated, at least in part, by the length of the myotubes or myotube-like cells, with relative elongation being an indicator of maturity or adult-like morphology. The myotubes or myotube-like cells with mature or adult-like morphology may, in some instances, have a length of at least about 200 µm, 250 µm, 300 µm, 350 µm, 400 µm, 450 µm, 500 µm, 550 µm, 600 µm, 650 µm, 700 µm, 1 mm, 1.25 mm, 1.5 mm, 1.75 mm, 2 mm, or greater in length. In some instances, the adult-like morphology is indicated, at least in part, by the myotubes or myotube-like cells having large diameters. The mature myotubes or myotube-like cells may, in some cases, have diameters (or maximal diameters) of at least about 2 µm, at least about 3 µm, at least about 3.5 µm, at least about 4 µm, at least about 4.5 µm, at least about 5 µm, at least about 5.5 µm, at least about 5.6 µm, at least about 5.7 µm, at least about 5.8 µm, at least about 5.9 µm, at least about 6.0 µm, at least about 6.1 µm, at least about 6.2 µm, at least about 6.3 µm, at least about 6.4 µm, at least about 6.5 µm, at least about 6.6 µm, at least about 6.7 µm, at least about 6.8 µm, at least about 6.9 µm, at least about 7.0 µm, at least about 12.0 µm, at least about 12.5 µm, at least about 13.0 µm, at least about 13.5 µm, at least about 14 µm, at least about 14.5 µm, at least about 15 µm, at least about 16 µm, at least about 17 µm, or larger. In preferred embodiments, the mature myotubes have a diameter of at least at least about 6.0 µm, at least 10 µm, or at least 12 µm. In some cases, myotubes or myotube-like cells in a culture may be made of mostly cells (e.g., greater than 50%, 75%, 80%, 90%, or 95% of total cells in the culture) with relatively large diameters in the absence of purification or selection for mature myotubes. For example, the myotubes or myotube-like cells in such culture may be made of mostly cells (e.g., greater than 50%, 75%, 80%, 90%, or 95% of total cells in the culture) at least about 6.0 µm, 6.1 µm, 6.2 µm, 6.3 µm, 6.4 µm, 6.5 µm, 6.6 µm, 6.7 µm, 6.8 µm, 6.9 µm, 7.0 µm, 12.0 µm, 12.5 µm, 13.0 µm, 13.5 µm, 14 µm, 14.5 µm, 15 µm or larger. In some instances, the percentage of mature myotubes in a culture is achieved without prior purification. In some instances, the adult-like morphology is indicated, at least in part, by the myotubes or myotube-like cells being highly multinucleated. In general, highly-nucleated myotubes or myotube-like cells may contain at least about 12, 13, 14, 15, 16, 17, 18, 19, 20, 21, 22, 23, 24, 25, 26, 27, 28, 29, 30, 31, 32, 33, 34, 35, 36, 37, 38, 39, 40 or even more nuclei per myotube or myotube-like cells. In some cases, the mature myotubes or myotube-like cells provided herein may comprise cells with multiple different numbers of nuclei. For example, many of the cells in a culture may have 12 or more nuclei per cell, while a few cells have 12 nuclei or few. In some cases, at least 50%, 75%, 80%, 90%, or 95% of the cells in a culture have a nuclei number of 12 or more. In some cases, myotubes or myotube-like cells in a culture may be made of mostly cells (e.g., greater than 50%, 75%, 80%, 90%, or 95% of total cells in the culture) with relatively large numbers of nuclei in the absence of purification or selection for mature myotubes. In some instances, the adult-like morphology is indicated, at least in part, by the cells having branches. For example, the myotubes or myotube-like cells may have at least 1, 2, 3, 4, 5, 6, 7, 8, 9, or 10 branching points. In some cases, myotubes or myotube-like cells in a culture may be made of mostly cells (e.g., greater than 50%, 75%, 80%, 90%, or 95% of total cells in the culture) with relatively high numbers of branching points in the absence of purification or selection for mature myotubes.

In some cases the methods herein provided may include generating myotubes or myotube-like cells that are immature. In general, myotubes or myotube-like cells may be considered to be immature if the cells are not more than about 100 µm in length, have average diameters of no more than about 6 µm, and no more than about 5 nuclei per myotube.

The myotubes or myotube-like cells generated according to the methods provided herein may be of various sizes. Area may be measured using a computer to detect total signal from an individual cell. In some cases, area is measured by multiplying the length of the cell by the diameter of the cell. In some cases, area is measured by dividing the total amount of signal emitted in a single field by the number of cells in that field. The individual myotubes or myotube-like cells may have an area (or average area) of at least about 1000 µm$^2$, 1200 µm$^2$, 1400 µm$^2$, 1500 µm$^2$, 1600 µm$^2$, 1700 µm$^2$, 1800 µm², 1900 µm², 2000 µm², 2200 µm², 2300 µm², 2400 µm², 2500 µm², 2600 µm², 2700 µm², 2800 µm², 2900 µm², 3000 µm², 3100 µm², 3200 µm², 3300 µm², 3400 µm², 3500 µm², 3600 µm², 3700 µm², 3800 µm², 3900 µm², 4000 µm², 4500 µm², 5000 µm², 5500 µm², 6000 µm², 6500 µm², 6700 µm², 7000 µm², 8000 µm², 9000 µm², 10000 µm², 15000 µm², 20000 µm², or even greater. In some cases, myotubes or myotube-like cells in a culture may be made of mostly cells (e.g., greater than 50%, 75%, 80%, 90%, or 95% of total cells in the culture) with relatively large areas in the absence of purification or selection for mature myotubes. In some cases, such culture may be made up of mostly cells (e.g., greater than 50%, 75%, 80%, 90%, or 95% of total cells in the culture) with an area of at least about 1000 µm², 1200 µm², 1400 µm², 1500 µm², 1600 µm², 1700 µm², 1800 µm², 1900 µm², 2000 µm², 2200 µm², 2300 µm², 2400 µm², 2500 µm², 2600 µm², 2700 µm², 2800 µm², 2900 µm², 3000 µm², 3100 µm², 3200 µm², 3300 µm², 3400 µm², 3500 µm², 3600 µm², 3700 µm², 3800 µm², 3900 µm², 4000 µm², 4500 µm², 5000 µm², 5500 µm², 6000 µm², 6500 µm², 6700 µm², 7000 µm², 8000 µm², 9000 µm², 10000 µm², 15000 µm², 20000 µm², or even greater.

The methods provided herein include generating myotubes or myotube-like cells with adult-like function. The myotubes or myotube-like cells may have adult-like function if they have high levels of expression of skeletal contractility genes, including, but not limited to: NEB (encoding nebulin), TTN N2A (encoding titin), TNNT (encoding troponin T), TNNI (encoding troponin I), TNNC (encoding troponin C), and MYOM1 (encoding myomesin). The myotubes and myotube-like cells may have adult-like function if they have high levels of expression of genes encoding skeletal muscle-specific enzymes, including but not limited to CKM (encoding muscle-specific creatine kinase). Myotubes or myotube-like cells may have high levels of expression of genes if the level of expression of the genes in myotubes or myotube-like cells is greater than the level of expression of the genes in pluripotent stem cells or non-muscle lineage cells (e.g. fibroblasts).

D. Efficiency and Yield for the Methods of Generating Myotubes or Myotube-Like Cells The methods provided herein for generating myotubes or myotube-like cells from myoblasts or myoblast-like cells may occur in a period of days. In some cases, the period for generating myotubes or myotube-like cells from myoblasts or myoblast-like cells may be about 1 day, 2 days, 3 days, 4 days, 5 days, 6 days, 7 days, 8 days, 9 days, or 10 days.

The methods provided herein may result in high yields of myotubes or myotube-like cells and/or may have high efficiencies. In some cases, the time (or duration) to generate myotubes or myotube-like cells from a plurality of pluripotent stem cells by performing the methods provided herein may be on the order of days to weeks. In some cases, the duration from pluripotent stem cell to myotube or myotube-like cell may be about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. Duration may be calculated as the time from start of differentiation (e.g., plating pluripotent stem cells in differentiation media) to the time when a majority of the pluripotent stem cells have differentiated to myotubes or myotube-like cells, for example, when at least about 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% of the pluripotent stem cells in the culture have differentiated to myotubes or myotube-like cells.

In some cases, the duration of differentiation of pluripotent stem cells to myoblasts by performing the methods provided herein may be on the order of days to weeks. For example, the duration from differentiation of pluripotent stem cells to myoblasts may be about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days or about 30 days. Duration may be calculated as the time from start of differentiation (e.g., plating pluripotent stem cells in differentiation media) to the time when a majority of the pluripotent stem cells have differentiated to myoblasts, for example, when at least about 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% of the pluripotent stem cells in the culture have differentiated to myoblasts.

The methods may also provide high yield in comparison to a starting population of pluripotent stem cells used to produce the myotubes or myotube-like cells (e.g., mature myotubes or myotube-like cells). In some cases, pluripotent stem cells are grown as a population in culture; the culture may undergo the stages of myogenesis in order to yield a 5:1 ratio of myotubes or myotube-like cells compared to the initial number of pluripotent stem cells. In some cases the ratio is at least 2:1, 3:1, 4:1, 5:1, 6:1, 7:1, 8:1, 9:1, 10:1, 11:1, 12:1, 13:1, 14:1, 15:1, 20:1, 50:1, 100:1, 200:1, 500:1, 750:1, 1000:1, 1500:1, 2000:1, or higher. In some cases, the ratio is achieved within 2, 3, 4, 5, 6, 7, 8, 9, 10, 12, 13, 14, 15, 16, 17, 18, 19, 20, 21, 22, 23, 24, 25, 30, 35, 40, 45, 50, 70 or 100 days.

The methods provided herein may generate mature myotubes or myotube-like with a high purity. Purity may refer to the percentage (%) or fraction of total cells in the culture that are mature myotubes or myotube-like cells. In some cases, the purity of myotubes or myotube-like cells (e.g., mature myotubes or myotube-like cells) in the culture, after performing a differentiation method as provided herein, is at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%. In some cases, the purity is obtained without first performing one or more purification or enrichment steps, such as one or more sorting steps (e.g., flow cytometry). In some cases, the purity of myotubes or myotube-like cells (e.g., mature myotubes or myotube-like cells) is at least 90%, 91%, 92%, 93%, 94%, 95%, 96%, 97%, 98%, 99% or 100% without performing one or more purification or enrichment steps, such as one or more sorting steps (e.g., flow cytometry).

In some cases, the population of cells after performing a differentiation method of the present disclosure is substantially free of neural cells or neural progenitor cells. For example, the population of cells after performing a differentiation method provided herein contains no more than about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35% or 40% of neural cells or neural progenitor cells.

V. Generating Myoblasts by Differentiation of Muscle Cell Precursors

The myotubes or myotube-like cells provided herein are generally produced from myoblasts or myoblast-like cells.

Myotubes or myotube-like cells may be generated from myoblasts or myoblast-like cells that are differentiated in vitro from satellite or satellite-like cells and pluripotent stem cells.

As used herein, the term "myoblast-like cell" refers to any cell that possesses structural or functional features associated with a naturally-occurring myoblast (e.g., myoblasts within an organism such as a human) but yet also possesses at least one structural or functional feature distinguishing the myoblast-like cell from a naturally-occurring myoblast. In preferred embodiments, a myoblast-like cell is a cell that is (a) produced in vitro from a satellite cell or satellite-like cell, which may or may not have been produced in vitro from a less-differentiated cell such as a stem cell, preferably a pluripotent stem cell or (b) derived from a myoblast-like cell, such as cells resulting from proliferation of a myoblast-like cell. As used herein, the term "myoblast" refers to a cell that possesses the structural and functional features exhibited by a naturally-occurring myoblast, and may or may not possess at least one structural or functional feature that distinguishes it.

A. Differentiation of Satellite Cells or Satellite-Like Cells into Myoblasts

Satellite cells and satellite-like cells are myoblast precursors. Satellite cells or satellite-like cells may be obtained from any method known in the art. In some cases, satellite cells or satellite-like cells may be produced in vitro by differentiating pluripotent stem cells. In some cases the satellite cells or satellite-like cells may be primary cells obtained directly from mammalian subjects or cadavers.

As used herein, the term "satellite-like cell" refers to any cell that possesses structural or functional features associated with a naturally-occurring satellite cell (e.g., satellite cell within an organism such as a human) but yet also possesses at least one structural or functional feature distinguishing the satellite-like cell from a naturally-occurring satellite cell. In preferred embodiments, a satellite-like cell is a cell that is (a) produced in vitro from a pluripotent stem cell (e.g., embryonic stem cell (ES cell) or induced pluripotent stem cell (iPS cell) or (b) derived from a satellite-like cell, such as cells resulting from proliferation of a satellite-like cell. As used herein, the term "satellite cell" refers to a cell that possesses the structural and functional features exhibited by a naturally-occurring satellite cell, and may or may not possess at least one structural or functional feature that distinguishes it. In some embodiments, satellite-like cells are PAX3- and PAX7-positive. In some embodiments, satellite-like cells are N-CAM/CD56/Leu-19 positive.

After satellite cells or satellite-like cells have been produced or obtained they may be seeded for culturing in vitro. The satellite or satellite-like cells may be seeded at a density of about $5 \times 10^3$ cells/cm$^2$. In some examples, the cells may be seeded at a density of from about $1.5 \times 10^3$ cells/cm$^2$ to about $10^4$ cells/cm$^2$; from about $2 \times 10^3$ cells/cm$^2$ to about $10^4$ cells/cm$^2$; from about $3 \times 10^3$ cells/cm$^2$ out $10^4$ cells/cm$^2$ from about $4 \times 10^3$ cells/cm$^2$ to about $10^4$ cells/cm$^2$; or from about $10^3$ cells/cm$^2$ to about $9 \times 10^3$ cells/cm$^2$.

Satellite cells or satellite-like cells may be cultured directly on tissue culture-grade plastic as a substrate. In some cases, satellite cells or satellite-like cells may be cultured on a coated substrate (e.g., substrate coated with fibronectin, extracellular matrix, collagen, laminin, gelatin, matrigel, geltrex or combinations thereof). In some cases, satellite cells or satellite-like cells may be cultured on a substrate coated with collagen type I.

Satellite cells or satellite-like cells may be grown in cultures in a 37° C., 5% $CO_2$ incubator at an oxygen level equal to that of the atmosphere. In some cases, satellite cells or satellite-like cells may be grown in cultures in a 37° C., 5% $CO_2$/5% $O_2$ incubator (e.g., under hypoxic conditions). Satellite cells or satellite-like cells may be grown in cultures for at least about 1 day, 2 days, 3 days, 4 days, 5 days, 6 days, 7 days, 8 days, 9 days, 10 days, 11 days, 12 days, 13 days, or 14 days. In a preferred embodiment, satellite cells or satellite-like cells are grown in culture until the cells are approximately 80% confluent. In some cases the satellite cells or satellite-like cells may be grown until the cells are approximately 60%, 65%, 70%, 75%, 80%, 85%, 90%, 95% or greater than 95% confluent.

Satellite cells or satellite-like cells may be grown in myoblast differentiation medium (e.g., Genea Biocells Myoblast Medium). Myoblast medium may contain serum-free M2 medium (Genea Biocells). Myoblast medium may contain 5% horse serum. In some cases, myotube medium may be supplemented with other factors, including, but not limited to: insulin, human recombinant epidermal growth factor (hr-EGF), human recombinant hepatocyte growth factor (hr-HGF) (Peprotech), human recombinant platelet-derived growth factor (hr-PDGF) (Peprotech), human recombinant basic fibroblast growth factor (hr-bFGF) (Miltenyi Biotec), oncostatin (Miltenyi Biotec), insulin-like growth factor 1 (Miltenyi Biotec), SB431542 (Miltenyi Biotec) and ascorbic acid. In a preferred embodiment, myoblast medium may contain serum-free M2 medium with 5% horse serum, 10 µg/ml insulin, 10 ng/ml hr-EGF, 20 ng/ml hr-HGF, 10 ng/ml hr-PDGF, 20 ng/ml hr-bFGF, 20 µg/ml oncostatin, 10 ng/ml insulin-like growth factor 1, 2 µM SB431542, and 200 µM ascorbic acid.

B. Differentiation of Pluripotent Stem Cells into Satellite Cells or Satellite-Like Cells Pluripotent stem cells may be differentiated in vitro into satellite cells or satellite-like cells. Pluripotent stem cells may be obtained from any method known in the art. In some cases, pluripotent stem cells may be derived from embryonic stem cells. In some cases, pluripotent stem cells may be derived from induced pluripotent stem cells. In some cases pluripotent stem cells may be obtained from mammalian subjects or cadavers, including, but not limited to human subjects who have a genetic disease.

Pluripotent stem cells may be cultured in a basal medium in the presence of chemical compounds that induce the cells to differentiate into satellite cells or satellite-like cells. In general, the basal medium that contains one or more compounds to induce differentiation of pluripotent stem cells into satellite cells or satellite-like cells is a myogenic induction medium. In some cases myogenic induction medium may contain serum-free M2 medium and 5% horse serum and may be supplemented with compounds including, but not limited to the Wnt pathway activator CHIR99021 (LC Laboratories), Alk5 inhibitor (a TGF-β receptor inhibitor) (Sapphire Bioscience), hr-EGF, insulin, dexamethasone (Sigma-Aldrich), Y27632 (a Rho-associated kinase inhibitor) and ascorbic acid. In a preferred embodiment myogenic induction medium may contain 3 µM CHIR99021, 2 µM Alk5 inhibitor, 10 ng/ml hr-EGF, 10 µg/ml insulin, 0.4 µg/ml dexamethasone, 10 µM Y27632 and 200 µM ascorbic acid.

According to the methods provided herein, satellite cells or satellite-like cells may be differentiated in vitro from pluripotent stem cells incubated in myogenic induction medium. The satellite or satellite-like cells may be differentiated by incubating pluripotent stem cells in myogenic induction medium in a 37° C., 5% $CO_2$ incubator for at least about 7 days, 8 days, 9 days, or 10 days. During differentiation to satellite cells or satellite-like cells the myogenic induction medium may be replaced on the pluripotent stem cells every day or every other day.

According to the methods provided herein, satellite cells or satellite-like cells may be produced by forced expression of genetic markers associated with satellite or satellite-like cells. Satellite cells or satellite-like cells may be produced by forced expression using any method known in the art, including, but limited to: introducing expression vectors encoding desired protein markers into cells, transducing cells with recombinant viruses, introducing exogenous purified polypeptides into cells, and introducing exogenous purified mRNAs encoding polypeptides of interest into cells.

Overview of Production of Satellite Cells

During the differentiation process, a less specialized cell becomes a more specialized cell type. Differentiation may impact aspects of a cell, such as a cell's size, shape, and/or functional capabilities. These changes are largely due to controlled modifications of gene expression. In one example of differentiation, a pluripotent stem cell is differentiated to a satellite cell or satellite-like cell. The differentiated satellite cell or satellite-like cell is then screened for a number of properties that characterize satellite cells or satellite-like cells (e.g., morphological, gene expression). Differentiated satellite cells or satellite-like cells that meet these screening criteria may then be subcloned and expanded. FIG. 3 is an illustration of four stages of differentiation from pluripotent stem cells to myotubes in accordance with embodiments of the present disclosure. Panel 310 of FIG. 3 shows pluripotent stem cells expressing a marker of pluripotency, Nanog, detected by immunofluorescent staining. Additionally, panel 320 of FIG. 3 shows a first stage of differentiation, in which pluripotent stem cells have been chemically differentiated to Pax3/Pax7-expressing satellite cells or satellite-like cells. Panel 330 of FIG. 3 shows a second stage of differentiation, in which satellite cells or satellite-like cells have been differentiated to myoblasts, which are immunofluorescently stained for MyoD, a myoblast marker. Further, panel 340 of FIG. 3 shows a third stage of differentiation, in which myoblasts join together to form myotubes, which is detected by immunofluorescent staining of dystrophin, a marker for myotube formation.

1. Chemical Differentiation of Pluripotent Stem Cells into Satellite Cells or Satellite-Like Cells In order to differentiate pluripotent stem cells into satellite cells or satellite-like cells, pluripotent stem cells may be obtained from a frozen stock or from a growing culture. These pluripotent stem cells can be cultured in a basal medium in the presence of chemical compounds that induce differentiation to satellite cells or satellite-like cells in a one-step process, which may or may not involve multiple media changes. In some cases, the pluripotent stem cells are cultured in a basal medium in the presence of chemical compounds that induce differentiation to satellite cells or satellite-like cells in a multi-step process, such as a process involving consecutive addition of different chemical compounds. In general, the basal medium with one or more compounds added to it to induce differentiation may be referred to as a "differentiation medium."

a. Differentiation Medium Components

Examples of a differentiation medium that may be used in a chemical differentiation process to produce satellite cells or satellite-like cells may include a medium comprising: basal medium, a Wnt activator, and a TGF-β receptor inhibitor. In some cases, the differentiation medium may include a ROCK inhibitor, a serum component, or a combination thereof. In some cases, the differentiation medium may include a LRRK2 inhibitor. Often, a differentiation medium provided herein is growth factor free.

The basal medium that is used in examples of the differentiation medium can vary, but generally comprises a nutrient-replete medium. Examples of basal media that may be used are MCDB120, Skeletal Muscle Cell Basal Medium (manufactured by Promocell), SkBM Basal Medium (manufactured by Lonza), SkBM-2 Basal Medium (manufactured by Lonza), Stem Cell Technologies 'APEL Medium' (manufactured by Stem Cell Technologies), or DMEM/F12.

Additionally, a ROCK inhibitor may be present in the differentiation medium. The ROCK inhibitor may reduce apoptosis at low cell densities. In some cases the concentration of the ROCK inhibitor, such as GSK429286A, Y-27632, LX7101, SAR407899, AT13148, GSK269962A, SR3677, RKI-1447, TTP 22, SLx-2119, Chroman 1, Y-33075 or Fasudil, is about 100 nM, 500 nM, 1 μM, 2.5 μM, 5 μM, 10 μM, 15 μM, 20 μM, 40 μM, 50 μM, 60 μM or more. In some cases, the ROCK inhibitor is continuously present during the differentiation process from pluripotent stem cell to satellite-like cell. In some cases, the ROCK inhibitor is present during a substantial portion of the differentiation process from originating pluripotent stem cell to satellite-like cell (e.g., greater than 1 day, greater than 2 days, greater than 3 days, greater than 4 days, greater than 5 days, greater than 10 days, or greater than 15 days).

The basal medium may additionally comprise a media described, or a media similar to one described, above with additional serum-like components. Such serum-like components can include BSA, fibroblast growth factor (FGF), insulin, fetuin, epidermal growth factor (EGF), horse serum, knock-out replacement serum, dexamethasone, or a combination thereof.

BSA may, in some examples, be present at a final concentration of at least about 0.1%, 0.5%, 1%, 2%, 3%, 4%, 5%, 6%, 7%, 8%, 9%, or 10%, or at most about 0.1%, 0.5%, 1%, 2%, 3%, 4%, 5%, 6%, 7%, 8%, 9%, or 10%. In some cases, cells can be contacted with BSA for more than 1 day, more than 2 days, more than 3 days, more than 4 days, more than 5 days, more than 6 days, more than 7 days, more than 8 days, or more than 9 days.

FGF (or other growth factor) may, in some examples, be present at a final concentration of at least about 0.5 ng/ml, 1 ng/ml, 1.5 ng/ml, 2 ng/ml, 2.5 ng/ml, 3 ng/ml, 3.5 ng/ml, 4 ng/ml, 4.5 ng/ml, 5 ng/ml, 6 ng/ml, 7 ng/ml, 8 ng/ml, 9 ng/ml, 10 ng/ml, 15 ng/ml, 20 ng/ml or 25 ng/ml. In some cases, FGF is present in a concentration of at most about 0.5 ng/ml, 1 ng/ml, 1.5 ng/ml, 2 ng/ml, 2.5 ng/ml, 3 ng/ml, 3.5 ng/ml, 4 ng/ml, 4.5 ng/ml, 5 ng/ml, 6 ng/ml, 7 ng/ml, 8 ng/ml, 9 ng/ml, 10 ng/ml, 15 ng/ml, 20 ng/ml or 25 ng/ml. In some cases, cells can be contacted with FGF for more than 1 day, more than 2 days, more than 3 days, more than 4 days, more than 5 days, more than 6 days, more than 7 days, more than 8 days, or more than 9 days.

Insulin may, in some examples, be present at a concentration of at least about 2 μg/ml, 3 μg/ml, 4 μg/ml, 5 μg/ml, 6 μg/ml, 7 μg/ml, 8 μg/ml, 9 μg/ml or 10 μg/ml. In some cases, cells can be contacted with insulin for more than 1 day, more than 2 days, more than 3 days, more than 4 days, more than 5 days, more than 6 days, more than 7 days, more than 8 days, or more than 9 days.

In some cases, the differentiation medium is substantially growth-factor free or absent of any growth factors (e.g., without EGF, FGF, FGF2, insulin, and the like). In some cases, the differentiation medium is substantially xenogeneic-free ("xeno-free") or substantially absent of components derived from non-human organisms. In some cases, the differentiation medium is both growth factor free and xeno-free.

Fetuin may, in some examples, be present at a final concentration of 10 µg/ml, 20 µg/ml, 30 µg/ml, 40 µg/ml, 50 µg/ml, 60 µg/ml, 70 µg/ml, 80 µg/ml, 90 µg/ml, or 100 µg/ml. EGF can be added to a final concentration of 5 ng/ml, 10 ng/ml, 15 ng/ml, and 20 ng/ml. In some cases, cells can be contacted with fetuin for more than 1 day, more than 2 days, more than 3 days, more than 4 days, more than 5 days, more than 6 days, more than 7 days, more than 8 days, or more than 9 days.

Horse serum may, in some examples, be present at a final concentration of 0.1%, 0.5%, 1%, 2%, 3%, 4%, 5%, 6%, 7%, 8%, 9%, or 10%. In some cases, cells can be contacted with horse serum for more than 1 day, more than 2 days, more than 3 days, more than 4 days, more than 5 days, more than 6 days, more than 7 days, more than 8 days, or more than 9 days.

Knock-out replacement serum may, in some examples, be present at a final concentration of 0.1%, 0.5%, 1%, 2%, 3%, 4%, 5%, 6%, 7%, 8%, 9%, or 10%. In some cases, cells can be contacted with a knock-out replacement serum for more than 1 day, more than 2 days, more than 3 days, more than 4 days, more than 5 days, more than 6 days, more than 7 days, more than 8 days, or more than 9 days.

Dexamethasone may, in some examples, be present at a final concentration of about 0.1 µg/ml and 1 µg/ml, such as 0.1 µg/ml, 0.2 µg/ml, 0.3 µg/ml, 0.4 µg/ml, 0.5 µg/ml, 0.6 µg/ml, 0.7 µg/ml, 0.8 µg/ml, 0.9 µg/ml, or 1 µg/ml. In some cases, cells can be contacted with dexamethasone for more than 1 day, more than 2 days, more than 3 days, more than 4 days, more than 5 days, more than 6 days, more than 7 days, more than 8 days, or more than 9 days.

In addition to basal medium and, optionally, a ROCK inhibitor and/or a serum component, the differentiation medium may include compounds that contribute to differentiation of pluripotent stem cells (or other type of stem cell such as multipotent stem cell) to satellite cells or satellite-like cells. In particular, pluripotent stem cells (or other type of stem cells) that are exposed to a Wnt pathway activator as well as a TGF-β receptor inhibitor (singly or in combination) may differentiate into satellite cells or satellite-like cells. Additionally, the satellite cells or satellite-like cells that are produced using this method may be capable of forming myoblasts.

In some cases, a compound that is present in a differentiation medium for differentiation of pluripotent stem cells to satellite cells or satellite-like cells is a Wnt pathway activator. Such activators can include CHIR99021, AR-A014418, AZD-1080, CHIR-98014, IM-12, Kenpaullone, 1-Azakenpaullone, LY2090314, SB 216763, SB 415286, TDZD-8, Tideglusib, TWS119, AZD-2858, WAY-316606, BML-284, QS11, IQ1, Enzastaurin, Sotrastaurin, Staurosporin, Go 6983, Go 6976, Ro 31-8220, Midostaurin, valproic acid (VPA), or deoxycholic acid (DCA). In particular, the use of a Wnt pathway activator may act as a GSK inhibitor, (e.g., GSK3-β inhibitor).

The Wnt pathway activator CHIR99021 may, in some examples, be present in the differentiation medium in concentrations of about 0.01 µM, 0.05 µM, 0.1 µM, 0.2 µM 0.5 µM, 0.7 µM, 1 µM, 1.5 µM, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, 25 µM, 30 µM, 35 µM, 40 µM, or 50 µM, or more. In some cases, cells can be contacted with the Wnt pathway activator, CHIR99021, for more than 1 day, more than 2 days, more than 3 days, more than 4 days, more than 5 days, more than 6 days, more than 7 days, more than 8 days, or more than 9 days.

The Wnt pathway activator AZD1080 may, in some examples, be present in the differentiation medium in concentrations of about 0.01 µM, 0.05 µM, 0.1 µM, 0.2 µM 0.5 µM, 0.7 µM, 1 µM, 1.5 µM, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, 25 µM, 30 µM, 35 µM, 40 µM, or 50 µM, or more. In some instances, cells can be contacted with AZD1080 for more than 1 day, more than 2 days, more than 3 days, more than 4 days, more than 5 days, more than 6 days, more than 7 days, more than 8 days, or more than 9 days.

The Wnt pathway activator QS11 may, in some examples, be present in the differentiation medium in concentrations of about 0.01 µM, 0.05 µM, 0.1 µM, 0.2 µM 0.5 µM, 0.7 µM, 1 µM, 1.5 µM, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, 25 µM, 30 µM, 35 µM, 40 µM, or 50 µM, or more. In some cases, cells can be contacted with QS11 for more than 1 day, more than 2 days, more than 3 days, more than 4 days, more than 5 days, more than 6 days, more than 7 days, more than 8 days, or more than 9 days.

The Wnt pathway activator IQ1 may, in some examples, be present in the differentiation medium in concentrations ranging of about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, or 20 µg/ml, or more. In some cases, cells can be contacted with IQ1 for more than 1 day, more than 2 days, more than 3 days, more than 4 days, more than 5 days, more than 6 days, more than 7 days, more than 8 days, or more than 9 days.

VPA may, in some examples, be present in the differentiation medium in concentrations of 0.005 µM, 0.01 µM, 0.05 µM, 0.1 µM, 0.5 µM, 1 µM, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, or more. In some cases, cells can be contacted with VPA for more than 1 day, more than 2 days, more than 3 days, more than 4 days, more than 5 days, more than 6 days, more than 7 days, more than 8 days, or more than 9 days.

The Wnt pathway activator DCA may, in some examples, be present in the differentiation medium in concentrations of about 0.1 µM, 0.5 µM, 1 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, or 100 µM, or more. In some cases, cells can be contacted with DCA for more than 1 day, more than 2 days, more than 3 days, more than 4 days, more than 5 days, more than 6 days, more than 7 days, more than 8 days, or more than 9 days.

In some cases, a TGF-β receptor inhibitor is present in the differentiation medium, either singly or in combination with another chemical agent such as a Wnt pathway activator. The TGF-β receptor inhibitor is generally capable of inhibiting at least a portion of a TGF-β receptor signaling pathway. In some cases, the TGF-β receptor inhibitor may inhibit at least a portion of a type I TGF-β receptor signaling pathway; in some cases, the TGF-β receptor inhibitor may inhibit type II TGF-β receptor signaling pathway. Examples of a TGF-β receptor inhibitor can include Alk5 inhibitor(s), SB431542, and A83-01. In particular, the use of a TGF-β receptor inhibitor may act as an Alk inhibitor, such as an Alk5 inhibitor.

The TGF-β receptor inhibitor (e.g., Alk5 inhibitor(s)) may, in some examples, be present in the differentiation medium at a concentration of about 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM, or more. In some cases, cells can be contacted with a TGF-β receptor inhibitor (e.g., Alk5 inhibitor(s)) for more than 1 day, more than 2 days, more than 3 days, more than 4 days, more than 5 days, more than 6 days, more than 7 days, more than 8 days, or more than 9 days.

SB431542 may, in some examples, be present in the differentiation medium in concentrations about 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM, or more. In some cases, the cells can be contacted with SB431542 for more than 1 day, more than 2 days, more than 3 days, more than 4 days, more than 5 days, more than 6 days, more than 7 days, more than 8 days, or more than 9 days.

A83-01 may, in some examples, be present in the differentiation medium in concentrations of about 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM, or more. In some cases, cells can be contacted with A83-01 for more than 1 day, more than 2 days, more than 3 days, more than 4 days, more than 5 days, more than 6 days, more than 7 days, more than 8 days, or more than 9 days.

In addition to presence of a Wnt pathway activator and a TGF-β receptor inhibitor, additionally signaling molecules may be present. Such signaling molecules can include transferrin, ascorbic acid, XAV939, VEGF, FGF, BIX01294, IGF-1, noggin, creatine, PD169316, SMO antagonist(s), horse serum, or sodium butyrate.

Transferrin may, in some examples, be present in the cell culture in concentrations of about 10 μg/mL, 30 μg/mL, 50 μg/mL, 70 μg/mL, 90 μg/mL, 110 μg/mL, 130 μg/mL, 150 μg/mL, 170 μg/mL, 190 μg/mL, 210 μg/mL, 230 μg/mL, 250 μg/mL, 270 μg/mL, or 300 μg/mL, or more. In some cases, cells can be contacted with transferrin for more than 1 day, more than 2 days, more than 3 days, more than 4 days, more than 5 days, more than 6 days, more than 7 days, more than 8 days, or more than 9 days.

Ascorbic acid may, in some examples, be present in the differentiation medium in concentrations of about 10 μM, 30 μM, 50 μM, 70 μM, 90 μM, 110 μM, 130 μM, 150 μM, 170 μM, 190 μM, 210 μM, 230 μM, 250 μM, 270 μM, or 290 μM, 310 μM, 330 μM, 350 μM, 370 μM, or 400 μM, or more. In some cases, cells can be contacted with ascorbic acid for more than 1 day, more than 2 days, more than 3 days, more than 4 days, more than 5 days, more than 6 days, more than 7 days, more than 8 days, or more than 9 days.

XAV939 may, in some examples, be present in the differentiation medium in concentrations of about 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM, or more. In some cases, cells can be contacted with XAV939 for more than 1 day, more than 2 days, more than 3 days, more than 4 days, more than 5 days, more than 6 days, more than 7 days, more than 8 days, or more than 9 days.

VEGF may, in some examples, be present in the differentiation medium in concentrations of 5 ng/ml, 10 ng/ml, 15 ng/ml, 20 ng/ml, 25 ng/ml, 30 ng/ml, 35 ng/ml, 40 ng/ml, 45 ng/ml, or 50 ng/ml. In some cases, cells can be contacted with VEGF for more than 1 day, more than 2 days, more than 3 days, more than 4 days, more than 5 days, more than 6 days, more than 7 days, more than 8 days, or more than 9 days.

A fibroblast growth factor (FGF) family member (e.g., FGF, FGF1, FGF2, FGF3, etc.) may, in some examples, be present in the differentiation medium in concentrations of about 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 100 ng/ml, 250 ng/ml or 500 ng/ml, or more. Cells, in some cases, can be contacted with FGF for more than 1 day, more than 2 days, more than 3 days, more than 4 days, more than 5 days, more than 6 days, more than 7 days, more than 8 days, or more than 9 days.

A histone methyltransferase inhibitor (e.g., BIX01294) may, in some examples, be present in the differentiation medium in concentrations of about 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM, or more. Cells, in some examples, can be contacted with BIX01294 for more than 1 day, more than 2 days, more than 3 days, more than 4 days, more than 5 days, more than 6 days, more than 7 days, more than 8 days, or more than 9 days.

IGF-1 may, in some examples, be present in the differentiation medium in concentrations of 0.5 ng/ml, 1 ng/ml, 5 ng/ml, 10 ng/ml, 15 ng/ml, 20 ng/ml, 25 ng/ml, 30 ng/ml, 35 ng/ml, 40 ng/ml, 45 ng/ml, or 50 ng/ml. Cells, in some examples, can be contacted with FGF for more than 1 day, more than 2 days, more than 3 days, more than 4 days, more than 5 days, more than 6 days, more than 7 days, more than 8 days, or more than 9 days.

Noggin may, in some examples, be present in the differentiation medium in concentrations of 10 ng/ml, 30 ng/ml, 50 ng/ml, 70 ng/ml, 90 ng/ml, 110 ng/ml, 130 ng/ml, 150 ng/ml, 170 ng/ml, or 190 ng/ml, 210 ng/ml, 230 ng/ml, or 250 ng/ml. Cells, in some examples, can be contacted with noggin for more than 1 day, more than 2 days, more than 3 days, more than 4 days, more than 5 days, more than 6 days, more than 7 days, more than 8 days, or more than 9 days.

Creatine may, in some examples, be present in the differentiation medium in concentrations of about 0.1 mM, 0.5 mM, 1 mM, 2 mM, 5 mM, 10 mM, 20 mM, 50 mM, or more. Cells can be contacted, in some cases, with creatine for more than 1 day, more than 2 days, more than 3 days, more than 4 days, more than 5 days, more than 6 days, more than 7 days, more than 8 days, or more than 9 days.

PD169316 may, in some examples, be present in the differentiation medium in concentrations of about 0.001 μM, 0.005 μM, 0.01 μM, 0.05 μM, 0.1 μM, 0.2 μM 0.5 μM, 0.7 μM, 1 μM, 1.5 μM, 2 μM, 2.5 μM, 3 μM, 4 μM, 5 μM, 6 μM, 7 μM, 8 μM, 9 μM, 10 μM, 11 μM, 12 μM, 12.5 μM, 13 μM, 14 μM, 15 μM, 16 μM, 17 μM, 18 μM, 19 μM, 20 μM, 25 μM, 30 μM, 35 μM, 40 μM, or 50 μM. In some cases, cells can be contacted with PD169316 for more than 1 day, more than 2 days, more than 3 days, more than 4 days, more than 5 days, more than 6 days, more than 7 days, more than 8 days, or more than 9 days.

SMO antagonist(s) may, in some examples, be present in the differentiation medium in concentrations of about 0.001 µM, 0.005 µM, 0.01 µM, 0.05 µM, 0.1 µM, 0.2 µM 0.5 µM, 0.7 µM, 1 µM, 1.5 µM, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, 25 µM, 30 µM, 35 µM, 40 µM, or 50 µM, or more. In some cases, cells can be contacted with SMO antagonist for more than 1 day, more than 2 days, more than 3 days, more than 4 days, more than 5 days, more than 6 days, more than 7 days, more than 8 days, or more than 9 days.

Horse serum may, in some examples, be present in the differentiation medium in concentrations of about 0.1%, 0.5%, 1%, 2%, 3%, 4%, 5%, 6%, 7%, 8%, 9%, or 10% or more. In some cases, cells can be contacted with horse serum for more than 1 day, more than 2 days, more than 3 days, more than 4 days, more than 5 days, more than 6 days, more than 7 days, more than 8 days, or more than 9 days.

Sodium butyrate may, in some examples, be present in the differentiation medium in concentrations of about 0.1 µM, 0.5 µM, 1 µM, 2 µM, 5 µM, 10 µM, 30 µM, 50 µM, 70 µM, 90 µM, 110 µM, 130 µM, 150 µM, 170 µM, 190 µM, 210 µM, 230 µM, 250 µM, 270 µM, or 290 µM, 310 µM, 330 µM, 350 µM, 370 µM, or 400 µM, or more. In some instances, cells can be contacted with sodium butyrate for more than 1 day, more than 2 days, more than 3 days, more than 4 days, more than 5 days, more than 6 days, more than 7 days, more than 8 days, or more than 9 days.

In some cases, Alk5 inhibitors can comprise 2-(3-(6-methylpyridine-2-yl)-1H-pyrazol-4-yl)-1,5-naphthyridine, that may, in some examples, be present in concentrations of 0.01 µM, 0.05 µM, 0.1 µM, 0.5 µM, 1 j M, 2 µM, 2.5 µM, 3 µM, 4 µM, 5 µM, 6 µM, 7 µM, 8 µM, 9 µM, 10 µM, 11 µM, 12 µM, 12.5 µM, 13 µM, 14 µM, 15 µM, 16 µM, 17 µM, 18 µM, 19 µM, 20 µM, 25 µM, 30 µM, 35 µM, 40 µM, or 50 µM, or more. In one particular embodiment the concentration of Alk5 inhibitor 2-(3-(6-methylpyridine-2-yl)-1H-pyrazol-4-yl)-1,5-naphthyridine is 2 µM or about 2 µM.

In some cases, a compound that is present in a differentiation medium for differentiation of pluripotent stem cells to satellite cells or satellite-like cells is a Leucine-rich repeat kinase 2 (LRRK2) inhibitor. Such inhibitors can include, without limitation, LRRK2-IN-1, CZC 54252, GSK2578215A, GNE-0877, GNE-7915, GNE-9605 and PF 06447475.

In some examples, the LRRK2 inhibitor is LRRK2-IN-1. LRRK2-IN-1 may be present in the differentiation medium at a concentration of about 1 nM, 5 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 10 µM, 20 µM, 30 µM, 40 µM, 50 µM, 60 µM, 70 µM, 80 µM, 90 µM, 100 µM or more than 100 µM. In some cases, the cells can be contacted with LRRK2-IN-1 for more than 1 day, more than 2 days, more than 3 days, more than 4 days, more than 5 days, more than 6 days, more than 7 days, more than 8 days, or more than 9 days.

b. Exposing Pluripotent Stem Cells to Differentiation Medium

Pluripotent stem cells (or other type of stem cell) may be differentiated to satellite cells, or satellite-like cells, by contacting the pluripotent stem cells (or other type of stem cell) with one or more differentiation media. The methods provided herein include one-step methods of differentiating a pluripotent stem cell (or other stem cell) wherein a single agent, or single combination of agents provided at the same time, triggers the differentiation pathway. In some cases, the method may comprise introducing a nucleic acid into a pluripotent stem cell (e.g., via transfection, transduction, viral transduction, electroporation, etc.) such that the pluripotent stem cell expresses the nucleic acid. In some cases, the method does not comprise introducing a nucleic acid into a pluripotent stem cell, or does not comprise transfecting a nucleic acid into a pluripotent stem cell, or does not comprise electroporating a nucleic acid into a pluripotent stem cell, or does not comprise transducing a nucleic acid (e.g., via viral vector) into a pluripotent stem cell, such that the nucleic acid is expressed by the cell and causes, or contributes to the differentiation of the pluripotent stem cell into a satellite cell or satellite-like cell. In some cases, the method comprises introducing a myogenic protein to the pluripotent stem cells. In some cases, the method does not comprise introducing a myogenic protein to the pluripotent stem cells.

In some examples, pluripotent stem cells can be plated and cultured as described herein or by any method known in the art, e.g., by plating as single cells in appropriate culture medium. In some cases, the pluripotent stem cells are contacted with the differentiation medium in a single step, thereby causing differentiation of the pluripotent stem cells into satellite cells or satellite-like cells or otherwise generating satellite cells or satellite-like cells.

In general, the single-step contacting may comprise contacting the pluripotent stem cells with a single differentiation medium that is provided to the cells at once, or serially over time (e.g., via media changes). In some cases, the single-step contacting may comprise contacting the pluripotent stem cells with a single differentiation medium that is provided to the cells at different concentrations over time (e.g., media changes involving altering the concentrations of differentiation media). In some embodiments, the components present in the single differentiation medium are sufficient to cause the pluripotent stem cells to differentiate into satellite cells or satellite-like cells (e.g., cells with functional, structural, morphological, or expression marker characteristics resembling those of a naturally-occurring satellite cell). In some embodiments, the component(s) present in the single differentiation medium are sufficient to cause satellite cells or satellite-like cells to be generated from the pluripotent stem cells. In some cases, the components present in the single differentiation medium are sufficient to cause the pluripotent stem cells to differentiate into satellite cells or satellite-like cells when the cells are serially exposed to the components (e.g., via one or more media changes). In some cases, contacting the pluripotent stem cells with the single differentiation medium comprises continuously contacting the cells with the differentiation medium. In other cases, contacting the pluripotent stem cells with the single differentiation medium comprises sporadically or serially contacting the cells with the differentiation medium.

In some cases, a component or set of components within a medium provided herein may be able to directly cause the generation of satellite cells or satellite-like cells from one or more pluripotent stem cells. For example, in some cases, a Wnt pathway activator and a TGF-β receptor inhibitor may, together, be capable of causing the generation of satellite cells or satellite-like cells from pluripotent stem cells without the addition of an additional differentiation agent.

In some cases, the contacting comprises contacting the pluripotent stem cells with two or more different differentiation media. The two or more different differentiation media may comprise different components. In some cases, the two or more different differentiation media are 2 or more, 3 or more, 4 or more, 5 or more, 6 or more, 7 or more, 8 or more, 9 or more, or 10 or more different differentiation media.

In some cases, the pluripotent stem cells may be contacted by or exposed to the one or more differentiation media (with or without media changes) for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 21 days, or at least 28 days. In some cases, the pluripotent stem cells may be contacted by the one or more differentiation media (with or without media changes) for at most 1 day, at most 2 days, at most 3 days, at most 4 days, at most 5 days, at most 6 days, at most 7 days, at most 8 days, at most 9 days, at most 10 days, at most 11 days, at most 12 days, at most 13 days, at most 14 days, at most 21 days, or at most 28 days. In some cases, the pluripotent stem cells are contacted with or exposed to the differentiation medium for about 12 hours, 1 day, 2 days, 3 days, 4 days, 5 days, 6 days, 7 days, 8 days, 9 days, 10 days, 11 days, 12 days, 13 days, 14 days, 21 days, 28 days, 30 days, 35 days, 40 days, 45 days, 50 days, 55 days, 60 days, 65 days, or 70 days.

The one or more pluripotent stem cells may be concurrently contacted by compounds of the differentiation medium, e.g., two or more compounds are administered to the pluripotent stem cells during an overlapping time-frame. For example, the pluripotent stem cells may be contacted with one compound on days 1-3 and with a second compound from days 2-5. In some cases, the one or more pluripotent stem cells may be simultaneously contacted by compounds of the differentiation medium. For example, the pluripotent stem cells may be contacted with two compounds during the same timeframe (e.g., contacted with two compounds for days 1-3). In some cases, the pluripotent stem cells are serially or sequentially contacted with two or more compounds of the differentiation media. For example, the pluripotent stem cells may be contacted with one compound on days 1-3 and with a second compound from days 4-6.

Components of the differentiation medium can be added in a single step. Components of the medium can be added sequentially. Additionally, components of the differentiation medium can be added simultaneously. Components of the differentiation medium can also be added in an overlapping manner, by contacting the cells with one component for a period of time before applying a second component. Components of the medium can also be added to cells individually or in mixtures. These additions can be performed without changing the composition of the medium throughout the process, such that the differentiation occurs due to the exposure to a single medium composition.

As mentioned herein, the differentiation medium (or media) may be changed or exchanged over time. In some cases, the differentiation medium is changed, added to, or replaced. Often, throughout these media exchanges the composition of the differentiation medium stays steady throughout the differentiation of the pluripotent stem cells to satellite cells or satellite-like cells. In some cases, the composition of the differentiation medium is varied. Media changes can be performed regularly, such as every six hours, every 12 hours, every day, every other day, every third day, every fourth day, or every fifth day. In some cases, the differentiation medium (or media) is changed at least 1, 2, 3, 4, 5, 6, 7, 8, 9, 10 or 15 times during the process of differentiating the pluripotent stem cells into satellite cells or satellite-like cells. Media can also be continuously added and removed, such as in a chemostat culture.

Pluripotent stem cells can be exposed to the differentiation medium continuously. Pluripotent stem cells can be exposed to the differentiation medium for a period of time before being returned to a maintenance medium. Further, differentiation can continue for a specific quantity of time (e.g. three days, five days, seven days, ten days, or fifteen days) or until a given gene or morphological marker is detected.

c. Yield, Efficiency, and Other Beneficial Features of the Methods of Producing Satellite Cells and Satellite-Like Cells The methods provided herein may result in high yields of satellite cells or satellite-like cell and/or may have high efficiencies. For example, when a plurality of pluripotent stem cells in an in vitro culture are differentiated using a differentiation medium as described herein, greater than 40% of the cells differentiated from said plurality of pluripotent stem cells may express Pax3, Pax7, and/or CD56. In some cases, greater than 20%, 30%, 40%, 45%, 50%, 55%, 60%, 65%, 70%, 75%, 80%, 85%, 90%, 91%, 92%, 93%, 94%, 95%, 96%, 97%, 98%, or 99% of the cells differentiated from said plurality of pluripotent stem cells may express Pax3, Pax7, and/or CD56. In some cases, greater than 20%, 30%, 40%, 45%, 50%, 55%, 60%, 65%, 70%, 75%, 80%, 85%, 90%, 91%, 92%, 93%, 94%, 95%, 96%, 97%, 98%, or 99% of the cells differentiated from said plurality of pluripotent stem cells are capable of differentiating into myoblasts. In some cases, greater than 20%, 30%, 40%, 45%, 50%, 55%, 60%, 65%, 70%, 75%, 80%, 85%, 90%, 91%, 92%, 93%, 94%, 95%, 96%, 97%, 98%, or 99% of the cells differentiated from said plurality of pluripotent stem cells are capable of differentiating into functional myoblasts.

In some cases, the time (or duration) to generate satellite cells or satellite-like cells from a plurality of pluripotent stem cells by performing the methods provided herein may be on the order of days to weeks. In some cases, the duration from pluripotent stem cell to satellite cell or satellite-like cell may be about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. Duration may be calculated as the time from start of differentiation (e.g., plating pluripotent stem cells in differentiation media) to the time when a majority of the pluripotent stem cells have differentiated to satellite cells or satellite-like cells, for example, when at least about 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% of the pluripotent stem cells in the culture have differentiated to satellite cells or satellite-like cells.

In some cases, the duration of differentiation of pluripotent stem cells to myoblasts by performing the methods provided herein may be on the order of days to weeks. For example, the duration from differentiation of pluripotent stem cells to myoblasts may be about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days or about 30 days. Duration may be calculated as the time from start of differentiation (e.g., plating pluripotent stem cells in differentiation media) to the time when a majority of the pluripotent stem cells have differentiated to myoblasts, for example, when at least about 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% of the pluripotent stem cells in the culture have differentiated to myoblasts.

A pluripotent stem cell provided in an in vitro culture may be contacted with one compound, or two or more compounds concurrently, thereby differentiating said human pluripotent stem cell into a cell expressing Pax3, Pax7, and/or CD56 (e.g., Pax3/CD56, Pax7/CD56, Pax3/Pax7/CD56). In particular, the cell expressing Pax3, Pax7, and/or CD56 may have the potential to form a myoblast, with a yield such that greater than five cells expressing Pax3, Pax7, and/or CD56 are generated from said pluripotent stem cell within a certain period of time (e.g., a nine-day period). Accordingly, when pluripotent stem cells are grown as a population in culture, the culture may produce cells expressing Pax3, Pax7, and/or CD56 in at least a 5:1 ratio to the initial number of pluripotent stem cells. In some cases the ratio is at least 2:1, 3:1, 4:1, 5:1, 6:1, 7:1, 8:1, 9:1, 10:1, 11:1, 12:1, 13:1, 14:1, 15:1, 20:1, 50:1 or 100:1. In some cases, the ratio is achieved within 2, 3, 4, 5, 6, 7, 8, 9, 10, 12, 13, 14, 15, 16, 17, 18, 19, 20, 21, 22, 23, 24, 25, 30, 35, 40, 45, 50, 70 or 100 days.

VI. Genetic Modifications

Introducing genetic modifications into mature myotubes or myotube-like cells according to the methods provided herein may create useful tools for developing both cell and drug therapies to treat subjects that have a muscular deficiency. For example, mature myotubes or myotube-like cells may be genetically modified to correct a mutation associated with a genetic muscle disease or disorder and then transplanted into a subject who has the disease or disorder in order to ameliorate the subject's symptoms. In some cases, mature myotubes or myotube-like cells may be genetically modified to have a mutation that is known or suspected to cause a genetic muscle disease. Such genetically modified myotubes or myotube-like cells may function as a platform for screening drugs that may reverse or reduce symptoms of the disease.

The genetic modification may be introduced by any method known in the art, e.g., transfection, transduction, CRISPR-mediated. In some cases, the genetic modification may involve introducing a wild-type of mutated gene into the myotubes or myotube-like cells. In some cases, the genetic modification may involve deleting or mutating a wild-type of mutated gene into the myotubes or myotube-like cells.

A mutation or mutations that are known to cause genetic disease may be introduced into healthy stem cell lines that are subsequently differentiated into satellite cells or satellite-like cells, which may ultimately be used to generate mature myotubes or myotube-like cells using the methods provided herein. For example, the dystrophin gene or part of the dystrophin gene, or one or more exons may be deleted in order to cause a frame-shift mutation or otherwise render the gene non-functional. Mutations may be heterozygous or homozygous, in male or female stem cell lines. The resulting modified stem cell lines may be differentiated to satellite cells or satellite-like cells and further to myoblasts and myotubes. These satellite cells, satellite-like cells, myoblasts, and myotubes may show disease-associated phenotypes caused by the introduced mutation(s). The genetically unmodified stem cell line may serve as an isogenic control which may be useful for drug screening, disease modeling, and disease research.

Myoblasts or myoblast-like cells, satellite or satellite-like cells, and pluripotent stem cells may be genetically modified and then used in the methods provided herein. Myoblasts carrying a genetic mutation or mutations causing a disease or disorder may be genetically modified to correct the mutation and thereby mitigate the disease or disorder experienced by a subject. In some cases, stem cells, such as a stem cell line, carrying a genetic mutation or mutations causing a disease or disorder may be genetically modified to correct the mutation and thereby mitigate the disease or disorder experienced by a subject. The genetic modification may be accomplished by any method known in the art.

The methods described herein may comprise obtaining myoblasts directly from a subject with a genetic disease or disorder affecting the subject's muscle tissue. The myoblasts may be genetically modified to correct the mutation. The genetically modified myoblasts may be differentiated into mature myotubes in vitro. In some cases the genetically modified myoblasts may be introduced into the subject and may differentiate into mature myotubes in vivo. In some cases the subject treated with genetically modified myoblasts or myotubes may experience a reduction in symptoms associated with the genetic disease or disorder. In some cases the subject treated with genetically modified myoblasts or myotubes may no longer experience symptoms associated with the genetic disease or disorder. In some cases, the subject treated with genetically modified myoblasts or myotubes may experience a temporary reduction in symptoms associated with the genetic disease or disorder.

Cells other than myoblasts (e.g., blood cells, skin cells) may be obtained from a subject with a genetic disease or disorder and may be subjected to conditions that enable them to become pluripotent stem cells or multipotent stem cells. In some cases cells may be obtained from a subject with a genetic disease or disorder affecting the subject's muscle tissue (e.g., muscular dystrophy, Duchenne muscular dystrophy, spinal muscular atrophy, etc.). The cells may then be subjected to conditions enabling them to become pluripotent stem cells or multipotent stem cells. For example, the cells may undergo de-differentiation and become induced pluripotent stem cells, particularly an induced pluripotent stem cell line. The pluripotent stem cells (or cell line) may be genetically modified to correct the mutation. For example, the subject may have one or more mutations in the dystrophin (DMD) gene and stem cells derived from the subject may be genetically modified to correct such mutations, or a portion of such mutations. The modified pluripotent stem cells may be differentiated into satellite or satellite-like cells using the methods described herein. The modified satellite or satellite-like cells may then be introduced into the subject with the genetic disease or disorder, in order to treat or ameliorate one or more aspects of the disorder. In some cases the modified satellite or satellite-like cells may be differentiated into myoblasts and mature myotubes according to the methods described herein. The resulting modified myoblasts and/or modified mature myotubes may be introduced into the subject with the genetic disease or disorder in order to treat or ameliorate one or more aspects of the disorder.

VII. Applications

The compounds provided herein (e.g., checkpoint inhibitors, Chk1 inhibitors, CHIR-124), mature myotubes or myotube-like cells (or their precursors, such as embryonic stem cells, induced pluripotent stem cells (iPSCs), satellite cells, myoblasts, or myoblast-like cells) generated according to the methods provided herein may be used in a wide variety of clinical and research applications. In some cases, mature myotubes or myotube-like cells (or their precursors) generated in vitro may be transplanted into a subject who has a muscular deficiency. In some cases, mature myotubes or myotube-like cells generated according to the methods provided herein may be used to screen drugs that may offset a muscular deficiency phenotype. This disclosure also provides numerous compounds (e.g., Chk1 inhibitors) that can be used to generate myotubes or myotube-like cells in vitro, or in combination with the administration of cell therapies in vivo. This disclosure also provides drugs comprising any of the compounds provided herein (e.g., Chk1 inhibitors). The drugs may be administered singly, or, in some cases the drugs are administered in combination with another therapy (e.g., synergistic mixture(s), drug therapy, and cell-therapy).

A. Cell Therapies

Embryonic stem cells, iPSCs, satellite cells, satellite-like cells, myoblasts, myotubes or myotube-like cells may be used according to the methods herein as a therapy to treat a subject with a disease or disorder (e.g., a genetic defect), particularly a disease or disorder affecting muscle function. The therapy may be directed to treating the cause of the disease and/or to treat the effects of the disease or condition. The myotubes or myotube-like cells may be transferred to, or close to, an injured site in a subject; or the cells can be introduced to the subject in a manner allowing the cells to migrate, or home, to an injured site. For example, the cells may be enclosed in a material, such as a microcapsule, designed to shuttle the cells to a site of interest. In some examples, the transferred cells may advantageously replace the damaged, diseased, or injured cells and allow improvement in the overall condition of the subject. In some instances, the transferred cells may stimulate tissue generation or repair.

In a representative example, a subject with a muscular degenerative disease or other muscular disorder (e.g., muscle injury) is treated with embryonic stem cells, iPSCs, satellite cells, satellite-like cells, myoblasts, myotubes that have been derived from myoblasts according to methods described herein or myotube-like cells that have been derived from myoblasts according to methods described herein. In some embodiments, the myoblasts may be differentiated by contacting the myoblasts with an agent or agents according to the disclosure herein (e.g. CHIR-124 or other CHK1 inhibitors, especially other quinolinone CHK-1 inhibitors) to differentiate the cells into mature myotubes or myotube-like cells in vitro, which are, in turn, transplanted or grafted into the subject. In preferred embodiments, the myotube precursor cells, the myotubes or the myotube-like cells may be introduced into the muscle of the subject, particularly the muscle of a subject with a muscular degenerative disease or disorder. In some embodiments, myotube-precursor cells (e.g., embryonic stem cells, iPSCs, satellite cells, satellite-like cells, myoblasts, myoblast-like cells, or other muscle precursor cell) are differentiated after transplantation or grafting into the subject by contacting the cells with a compound or compounds to differentiate the myotube precursor cells into myotubes or myotube-like cells. The contacting may occur directly, such as by mixing the cells with the compound prior to transplantation; or indirectly, by administering the compound or compounds to the subject.

In some examples, myotubes or myotube-precursor cells (e.g., embryonic stem cells, iPSCs, satellite cells, satellite-like cells, myoblasts, or myoblast-like cells) that are genetically modified or derived from genetically altered cells (such as genetically modified myoblasts or pluripotent stem cells) are introduced into the subject. In some examples, an induced pluripotent stem cell line may be generated from a patient with a muscular deficiency disease or disorder such as muscular dystrophy that is caused by a genetic mutation. The mutation may be corrected in the induced pluripotent stem cells which may then be differentiated into satellite cells, satellite-like cells, myoblasts, myoblast-like cells, myotubes, or myotube-like cells according to the present disclosure. The satellite cells, satellite-like cells, myoblasts, myoblast-like cells, myotubes, or myotube-like cells with the corrective mutation may then be transplanted into the patient in order to restore, improve, or enhance muscle function. The satellite cells, satellite-like cells, myoblasts, myoblast-like cells, myotubes, or myotube-like cells with the corrective mutation may then be transplanted into the patient followed by in order to restore, improve, or enhance muscle function In some specific examples, induced pluripotent stem cells (or an induced pluripotent stem cell line) may be generated from a patient with a mutation causing muscular dystrophy (e.g., Duchenne muscular dystrophy). The mutation may be corrected in the induced pluripotent stem cells using genetic-modification techniques known in the art. The genetically-modified induced pluripotent stem cells may be differentiated to myotubes or myotube-like cells according to the present disclosure. In some embodiments, the myotubes or myotube-like cells are transplanted into the patient where they may produce functional, non-mutated proteins so as to restore or enhance muscle function. In other embodiments, the genetically-modified induced pluripotent stem cells are differentiated to satellite cells, satellite-like cells, myoblasts, or myoblast-like cells and then transplanted into the patient, followed by treatment with an agent or agents according to the disclosure herein (e.g. CHIR-124 or other CHK1 inhibitors, especially other quinolinone CHK1 inhibitors) that may encourage production of mature myotubes.

The treatment of a muscular degenerative disease such as muscular dystrophy (e.g., Duchenne muscular dystrophy) can be accomplished by injection of mature myotubes or myotube-like cells that have the ability to restore muscle loss, into muscles that are diseased or injured. The myotubes or myotube-like cells may fuse with existing myotubes. The treatment of a muscular degenerative disease such as muscular dystrophy (e.g. Duchenne muscular dystrophy) in a subject can also be accomplished by transplantation of myotube-precursor cells (e.g., embryonic stem cells, iPSCs, satellite cells, satellite-like cells, myoblasts, myoblast-like cells), followed by treatment with an agent or agents according to the disclosure herein (e.g. CHIR-124 or other CHK1 inhibitors, especially other quinolinone CHK1 inhibitors) to differentiate the myotube-precursor cells into myotubes or myotube-like cells that may fuse with existing myotubes. In some embodiments, treatment of the subject is accomplished by administering CHIR-124 via a suitable method to achieve a local concentration of about 0.1 uM to about 1 uM in the subject.

The myotubes, myotube-like cells, or myotube-precursor cells (e.g., embryonic stem cells, iPSCs, satellite cells, satellite-like cells, myoblasts, or myoblast-like cells) may be transferred to subjects suffering from a wide range of diseases and disorders. Subjects suffering from neurological and/or neuromuscular diseases or disorders may especially benefit from satellite cell therapies. In some approaches, the myotubes, myotube-like cells, or myotube-precursor cells (e.g., embryonic stem cells, iPSCs, satellite cells, satellite-like cells, myoblasts, or myoblast-like cells) may be transplanted to a muscle site to treat a neuromuscular condition, e.g. muscular dystrophy, Duchenne muscular dystrophy, etc. A muscular disease or disorder that may be treated by, or ameliorated by, the disclosed myotube-precursor cells (embryonic stem cells, iPSCs, satellite cells, satellite-like cells, myoblasts, or myoblast-like cells), myotubes and myotube-like cells may be a genetic disease or disorder, or may have non-genetic causes. In some cases, the disease or disorder is chronic; in others, the disease or disorder is acute or sub-acute; in still other cases, the disease or disorder is a recurrent disease or disorder. Exemplary diseases or disorders that may be treated by, or ameliorated by, the disclosed myotubes may include genetic diseases as well as non-genetic diseases. Exemplary diseases or disorders may include: muscular dystrophy, Huntington's disease, Merosin deficiency 1A, nemaline myopathy, and Spinal Muscular Atrophy (SMA). Examples of muscular dystrophies that may be treated or improved by the disclosed cells include Becker, congenital, facioscapulohumeral (FSH), myotonic (type I and II), oculopharyngeal, distal, Duchenne muscular dystrophy, and Emery-Dreifuss muscular dystrophy. Duchenne and Becker muscular dystrophies are caused by a mutation of a gene located on the X chromosome and predominantly affect males, although females can sometimes have severe symptoms as well. Additional diseases or disorders that may be treated by, or ameliorated by, the disclosed methods and compositions may include: cachexia, sporadic diseases, sarcopenia, muscle wasting, muscle atrophy, muscle strain, muscle injury, multiple sclerosis, Parkinson's disease, or muscle wasting associated with aging.

Additionally or alternatively, the myotube-precursor cells (e.g., embryonic stem cells, iPSCs, satellite cells, satellite-like cells, myoblasts, myoblast-like cells or other muscle precursor cells), myotubes, or myotube-like cells may be transplanted into a subject using a scaffold, using a scaffold-free method, or using other transplantation devices. The scaffold may be made of any material known in the art. In some cases, the scaffold is a biodegradable scaffold, a resorbable scaffold, or other type of scaffold. In some cases, the scaffold may comprise a matrix (e.g., biodegradable matrix, resorbable matrix). In some cases, the myotubes or myotube-like cells, or cells derived therefrom, are encapsulated in microcapsule(s) prior to transplantation. In some cases, the microcapsule may possess homing features enabling the cells to be directed to a location of interest. In some cases, a scaffold is used along with transplantation of myotube-precursor cells (e.g., embryonic stem cells, iPSCs, satellite cells, satellite-like cells, myoblasts, myoblast-like cells), followed by treatment with an agent or agents according to the disclosure herein (e.g. CHIR-124 or other CHK1 inhibitors, especially other quinolinone CHK1 inhibitors) to differentiate the myotube-precursor cells into myotubes or myotube-like cells. In some embodiments, treatment with the agent or agents (e.g. CHIR-124 or other CHK1 inhibitors, especially other quinolinone CHK1 inhibitors) accelerates differentiation or improves the differentiation yield of the myotube-precursor cells into myotubes or myotube-like cells relative to the use of the transplantation scaffold alone.

Skeletal muscle cells such as myotubes and myotube-like cells may be injected at a number of locations across the body of a subject. For example, the myotubes or myotube-like cells may be injected at locations to access muscle formation, e.g. arm muscles such as coracobrachialis, biceps brachii, and brachialis, leg muscles such as tibialis anterior; extensor hallucis longus; extensor digitorum; and fibularis tertius, or other muscle locations. Myotube-precursor cells (embryonic stem cells, iPSCs, satellite cells, satellite-like cells, myoblasts, or myoblast-like cells) may also be injected at a number of locations across the body of a subject. For example, the myotube precursor cells, myotubes or myotube-like cells may be injected at locations to access muscle formation, e.g. arm muscles such as coracobrachialis, biceps brachii, and brachialis, leg muscles such as tibialis anterior; extensor hallucis longus; extensor digitorum; and fibularis tertius, or other muscle locations.

The number of administrations of treatment to a subject may vary. Introducing the myotube-precursor cells or differentiated cells (e.g. myotubes, myotube-like cells) into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease, and parameters of the individual subject being treated.

In some examples, the cells may be introduced to the subject via any of the following routes: parenteral, intravenous, intraarterial, intramuscular, subcutaneous, transdermal, intraperitoneal, or into spinal fluid. In particular, the cells may be introduced to the subject via direct injection of the cells into skeletal muscle of the subject.

During transplantation of the myotube-precursor cells (e.g., embryonic stem cells, iPSCs, satellite cells, satellite-like cells, myoblasts, or myoblast-like cells), myotubes or myotube-like cells, drugs (e.g., a checkpoint inhibitor, Chk1 inhibitor) may be given to the subject during the same period of time. For example, drugs may be administered prior to, during, or subsequent to transplantation of myotubes or myotube-like cells, or a combination thereof. Examples of drugs that may be administered to the subject include but are not limited to: drugs to treat the disease or injury to the subject, immunosuppressant drugs, or one or more compounds described herein that promote differentiation of myoblasts into mature myotubes (e.g. CHIR-124 or other CHK1 inhibitors, especially other quinolinone CHK1 inhibitors). In some embodiments, CHIR-124 is administered via a suitable method to the subject to achieve a local concentration of about 0.1 uM to about 1 uM in the subject.

Exemplary immunosuppressive drugs include calcineurin inhibitors, such as cyclosporine or tacrolimus, mTOR inhibitors, such as sirolimus or everolimus, purine synthesis inhibitors or purine analogues, such as mycophenolate mofetil or azathioprine, or steroids, such as prednisone. In some cases, the drugs administered to the subject do not include an immunosuppressant drug, particularly when the subject is unlikely to reject the cell therapy (e.g., when the cells are derived from the subject's own cells).

The myotube-precursor cells (e.g., embryonic stem cells, iPSCs, satellite cells, satellite-like cells, myoblast, or myoblast-like cells), myotubes or myotube-like cells can be administered using a variety of instruments, such as syringes. The myotube-precursor cells (e.g., embryonic stem cells, iPSCs, satellite cells, satellite-like cells, myoblasts), myotubes and myotube-like cells may also be injected with a buffer, such as saline, phosphate-buffered saline or serum. Myotube-precursor cells (e.g., embryonic stem cells, iPSCs, satellite cells, satellite-like cells, myoblasts, or myoblast-like cells), myotubes or myotube-like cells may be administered with antibiotics, such as vancomycin or levofloxacin.

The dosage of myotube-precursor cells (e.g., embryonic stem cells, iPSCs, satellite cells, satellite-like cells, myoblasts, or myoblast-like cells), myotubes or myotube-like cells that may be transplanted into a subject may differ based on the disease or injury of the subject, the progression of the disease or injury of the subject, and the degree of severity of the disease or injury of the subject. Additionally, the number of treatments provided to a subject may vary. A single treatment may be administered to the subject or multiple treatments may be given to the subject. In some cases, the subject may be treated about 1, 2, 3, 4, 5, 6, 7, 8, 9, 10, 11, 12, 13, 14, 15, 20, 25 or more times with the cells provided herein. In some cases, the subject may be treated less than 1, 2, 3, 4, 5, 6, 7, 8, 9, 10, 15 or 20 times within a year period. The treatments themselves may also vary in the number of sites that are provided with myotubes or myotube-like cells. In examples, a single treatment of myotubes or myotube-like cell transplantation may include 1, 2, 3, 4, 5, 6, 7, 8, 9, 10, 20, 50 or 100 or more injection sites for the direct skeletal muscle injection of myotubes or myotube-like cells. In some cases, a single dose of cells comprises about $10^1$, about 50, about $10^2$, about $5\times10^2$, about $10^3$, about $5\times10^3$, about $10^4$, about $5\times10^4$, $10^5$, about $5\times10^5$, about $10^6$, about $5\times10^6$, about $10^7$, about $5\times10^7$, about $10^8$, about $5\times10^8$, about $10^9$, about $5\times10^9$, about $10^{10}$, about $5\times10^{10}$, about $10^{11}$, about $5\times10^{11}$, or more cells. In some cases, a single dose of cells comprises at most $10^2$, at most $5\times10^2$, at most $10^3$, at most $5\times10^3$, at most $10^4$, at most $5\times10^4$, at most $10^5$, at most $5\times10^5$, at most $10^6$, at most $5\times10^6$, at most $10^7$, at most $5\times10^7$, at most $10^8$, at most $5\times10^8$, at most $10^9$, at most $5\times10^9$, at most $10^{10}$, at most $5\times10^{10}$, at most $10^{11}$, or at most $5\times10^{11}$ cells.

In some embodiments, once myotubes or myotube-like cells are provided to the patient, the myotubes or myotube-like cells may fuse with myoblasts or myotubes of the subject and may form fused muscle cell components. In other embodiments, myotube-precursor cells (e.g., embryonic stem cells, iPSCs, satellite cells, satellite-like cells, myoblasts, myoblast-like cells) treated with an agent or agents according to the disclosure herein that promote myotube differentiation may fuse with myoblasts or myotubes of the subject and may form fused muscle cell components. Consequences of treatment may include restoration of muscle; halting of muscle degradation; slowing of muscle degradation; improvement of factors associated with a subject's disease or injury such as production of dystrophin; or combinations thereof.

Improvement of factors associated with a subject's disease or injury may be associated with tests of muscle restoration or muscle function. The degree of muscle restoration may be assessed by one or more tests of certain muscle attributes, such as muscle mass, muscle strength as measured by resistance to a force, amount of contraction in response to a stimulus, and strength of contraction in response to a stimulus such as an electric shock, the time performance of a given task, or other examples of muscle-based tests.

The restoration of muscle can be assessed based on the amount, or degree, of improvement of certain muscle attributes. In particular, the muscle attribute (e.g., muscle mass, strength, etc.) may improve by about 1-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 100-fold, 150-fold, 200-fold, 250-fold, or 300-fold or more. In some cases, the muscle attribute may improve by >1%, >5%, >10%, >15%, >20%, >25%, >50%, >60%, >70%, >75%, >80%, >90%, >95%, >99%, >100% or more. In some more particular cases, muscle strength improves by >1%, >5%, >10%, >15%, >20%, >25%, >50%, >60%, >70%, >75%, >80%, >90%, >95%, >99%, >100%, >200% or more. The improvement to the muscle attribute may occur within a certain time period, such as within about 1 day, 2 days, 3 days, 4 days, 5 days, 7 days, 10 days, 2 weeks, 3 weeks, 4 weeks, 1 month, 6 weeks, 2 months, 10 weeks, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1.5 years, or 2 years, or more from the time of introduction of the satellite-like or satellite cells. For example, in some cases, the improvement of the muscle attribute (e.g., strength, mass, etc.) may be >1% within a month, >5% within a month, >10% within a month, >15% within a month, >20% within a month, >25% within a month, >50% within a month, >60% within a month, >70% within a month, >75% within a month, >80% within a month, >90% within a month, >95% within a month, >99% within a month, >100% within a month, >200% within a month, >250% within a month, >300% within a month, >400% within a month, >500% within a month or an even higher percentage within a month.

In some cases, treating a subject with myotube-precursor cells (e.g., embryonic stem cells, iPSCs, satellite cells, satellite-like cells, myoblasts, or myoblast-like cells), myotubes or myotube-like cells can result in the halting or slowing of muscle degeneration within a certain time period. In some cases, the rate of muscle degeneration can be slowed by about >1% within a month, >5% within a month, >10% within a month, >15% within a month, >20% within a month, >25% within a month, >50% within a month, >60% within a month, >70% within a month, >75% within a month, >80% within a month, >90% within a month, >95% within a month, >99% within a month, >100% within a month, >200% within a month, >250% within a month, >300% within a month, >400% within a month, >500% within a month or by an even higher percentage within a month of treatment with the cells. Additionally, muscle degeneration may be completely halted based on cell therapy using myotubes or myotube-like cells. Muscle degeneration may be completely halted within a certain period of time, such as within about 1 day, 2 days, 3 days, 4 days, 5 days, 7 days, 10 days, 2 weeks, 3 weeks, 4 weeks, 1 month, 6 weeks, 2 months, 10 weeks, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1.5 years, or 2 years, or more from the time of introduction of the satellite-like or satellite cells.

B. Drug Screening

In addition to uses in cell therapies, myotubes or myotube-like cells may be used to serve as a platform for drug screening. In particular, drugs may be assayed to test effects on a phenotype of the myotubes or myotube-like cells such as cell morphology, marker expression, proliferation or differentiation. In some cases, the phenotype is associated with muscle function (e.g., muscular dystrophy). The cells provided herein thus may also be useful for disease modeling and disease research for such genetic diseases or disorders.

In one example, cells that are tested are healthy myotubes or myotube-like cells that are chemically differentiated from healthy myoblasts. In another example, cells that are tested are diseased myotubes or myotube-like cells that are differentiated from diseased myoblasts. Diseased myoblasts may include myoblasts that have particular genetic mutations associated with genetic diseases, such as neuromuscular genetic diseases, such as muscular dystrophy. In some cases, the diseased myoblasts are derived from a subject carrying a genetic mutation associated with a muscular degenerative disease. In some cases, the diseased myoblasts are genetically engineered to carry a mutation that causes—or is associated with—a muscular genetic disease. The mutation may be identical to a mutation carried by a subject (e.g., human subject), or may be substantially similar to such mutation. The diseased myotubes or myotube-like cells may be tested for phenotypes of disease. Effects of disease may be characterized at a cellular and tissue level and other assessments may be performed on the diseased myotubes or myotube-like cells. Characterizing the effects of the disease may include assessing function and morphology of the myotubes, marker expression of the myotubes, proliferation and differentiation of myotubes, myotube length, myotube diameter, myotube branching, fusion index, or the number of nuclei per myotube.

According to the methods provided herein, drugs may be assayed on myoblasts or myoblast-like cells to identify drugs that result in differentiation of myoblasts or myoblast-like cells into mature myotubes or myotube-like cells. Differentiation of myoblasts or myoblast-like cells into mature myotubes or myotube-like cells may be measured by any method known in the art including, but not limited to measuring myotube length, myotube diameter and number of nuclei per myotube. Identified drugs may be useful for boosting development of endogenous skeletal muscle cells and therefore increased muscle mass and function in patients with a muscular deficiency.

The drug screening assays and disease modeling assays using the disclosed myoblasts and myoblast-like cells and myotubes and myotube-like cells may be designed for a wide variety of diseases and disorders, particularly genetic diseases or disorders. Exemplary diseases or disorders include, but are not limited to: Huntington's disease, Merosin deficiency 1A, nemaline myopathy, and Spinal Muscular Atrophy (SMA), and muscular dystrophy. Examples of muscular dystrophy include Becker, congenital, facioscapulohumeral (FSH), myotonic (type I and II), oculopharyngeal, distal, Duchenne muscular dystrophy, and Emery-Dreifuss muscular dystrophy. Duchenne and Becker muscular dystrophies are caused by a mutation of a gene located on the X chromosome and predominantly affect males, although females can sometimes have severe symptoms as well. Additionally, most types of muscular dystrophy are multi-system disorders with manifestations in body systems including the heart, gastrointestinal system, nervous system, endocrine glands, eyes and brain.

According to the methods provided herein, small molecules that are known or suspected to target networks and pathways related to muscle development may be used for drug screening assays. The small molecules may have known or suspected targets that are involved in kinome signaling, including, but not limited to, kinases and phosphatases: AAK1, ABL1, ABL2, ACVR1, ACVR1B, ACVR2A, ACVR2B, ACVRL1, ADCK3, AKT1, AKT2, AKT3, ALK, AMPK, ANKK1, NUAK1, M3K5, M3K6, AURKA, AURKB, AURKC, AXL, BIKE, BLK, BMPR1A, BMPR1B, BMPR2, BMX, BRAF, PTK6, BRSK1, BRSK2, BTK, BUB1, CAMK1, CAMK1D, CAMK1G, CAMK2A, CAMK2B, KCC2D, CAMK2G, KCC4, KKCC1, CAMKK2, CASK, CDCL1, CDCL2, CDCL5, CDK11, CDK2, CDK3, CDK4-cyclinsD1/3, CDK5, CDK7, CDK8, CDK9, CDKL1, CDKL2, CDKL3, CDKL5, CHEK1, CHK2, CIT, CLK1, CLK2, CLK3, CLK4, CSF1R, CSK, CSNK1A1, CSNK1A1L, CSNK1D, CSNK1E, KC1G1, KC1G2, CSNK1G3, CSNK2A1, CSNK2A2, CTK, DAPK1, DAPK2, DAPK3, DCLK1, DCAMKL2, DCAMKL3, DDR1, DDR2, M3K12, DMPK, DMPK2, DRAK1, DRAK2, DYRK1A, DYRK1B, DYRK2, EGFR, EIF2AK1, EPHA1, EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, MK03, MK01, ERK3, ERK5, ERK8, ERN1, FAK1, FER, FES, FGFR1, FGFR2, FGFR3, FGFR4, FGR, FLT3, FLT4, FRK, FYN, GAK, GSN, GRK1, GRK4, GRK7, GSK3A, GSK3B, HASP, HCK, HIPK1, HIPK2, HIPK3, HIPK4, M4K1, HUNK, ICK, IGF1R, IKKA, IKKB, IKKE, INSR, INSRR, IRAK1, IRAK3, ITK, JAK1, JAK2, JAK3, JANK1, MK09, KGP1, KGP2, KIT, KPCD, KPCD1, KPCD2, KPCD3, KPCE, KPC1, KPCL, KPCT, LATS1, LATS2, LCK, LIMK1, LIMK2, LKB1, LOK, LRRK, LTK, LYN, M3K13, M3K2, M4K3, MAK, MAP3K1, MAP3K15, MAP3K3, MAP3K4, MAP4K2, MAP4K4, MAP4K5, MAPKAPK2, MAPKAPK5, MAPK1, MARK2, MARK3, MARK4, MAST1, MP2K1, MP2K2, MP2K3, MP2K4, MP2K5, MP2K6, MELK, MERTK, MET, MINK, MP2K7, MP2K7, MKNK1, MKNK2, MLCK, MLK1, MLK2, MLK3, MLTK, MRCKA, MRCKB, MST1, MST1R, MST2, MST3, MTOR, MUSK, MYLK, MYLK2, MYLK4, MYO3A, MYO3B, NDR1, NDR2, NEK1, NEK10, NEK11, NEK2, NEK3, NEK4, NEK5, NEK6, NEK7, NEK9, NIM1, NLK, OSR1, MK14, MK11, MK13, MK12, PAK1, PAK2, PAK3, PAK4, PAK6, PAK7, CDK16, PCTH2, PCTK3, PDPK1, CDK15, CDK14, PGFRA, PGFRB, PHKG1, PHKG2, PIK3C2B, PIK3C2G, PIK3CA, PIK3CB, PIK3CD, PIK3CG, PIK4CB, PIM1, PIM2, PIM3, PIP5K1A, PIP5K1C, PIP5K2B, PI42C, PKAC-alpha, PKAC-beta, PKMYT1, PKN1, PKN2, PLK1, PLK2, PLK3, PLK4, PRKR, PRKX, PRP4, FAK2, SIK3, RAF1, RET, RIOK1, RIOK2, RIOK3, RIPK1, RIPK2, RIPK4, RIPK5, ROCK1, ROCK2, ROS1, RSK1, RPS6KA4, RPS6KA5, S6K1, CBK1, SGK1, SGK2, SGK3, SIK1, SIK2, SLK, SNARK, SNRK, SRC, SRMS, SRPK1, SRPK2, SRPK3, STK16, STK33, STK35, STK36, STK39, SYK, TAK1, TAOK1, TAOK2, TAOK3, TBK1, TEC, TESK1, TGFBR1, TGFBR2, TIE1, TIE2, TLK1, TLK2, TNIK, TNK1, TNK2, TNII3K, TRKA, TRKB, TRKC, TRPM6, TSSK1, TTK, TXK, TYK2, TYRO3, ULK1, ULK2, ULK3, VGFR1, VGFR2, VRK2, WEE1, WEE2, WNK1, WNK3, YANK1, YANK2, YANK3, YES, YSK1, YSK4, ZAP70.

According to the methods provided herein, small molecules that are known or suspected to target networks and pathways related to muscle development may be used for drug screening assays. The small molecules may have known or suspected targets that are Class A G-protein coupled receptors, including, but not limited to: $5\text{-HT}_{1A}$, $5\text{-HT}_{1B}$, $5\text{-HT}_{1D}$, $5\text{-HT}_{1E}$, $5\text{-HT}_{1F}$, $5\text{-HT}_{2A}$, $5\text{-HT}_{2B}$, $5\text{-HT}_{2C}$, $5\text{-HT}_4$, $5\text{-HT}_{5A}$, $5\text{-HT}_{5B}$, $5\text{-HT}_6$, $5\text{-HT}_7$, $M_1$, $M_2$, $M_3$, $M_4$, $M_5$, $A_1$, $A_{2A}$, $A_{2B}$, $A_3$, $\alpha_{1A}$, $\alpha_{1B}$, $\alpha_{1D}$, $\alpha_{2A}$, $\alpha_{2B}$, $\alpha_{2C}$, $\beta_1$, $\beta_2$, $\beta_3$, $AT_1$, 2, apelin receptor, GPBA receptor, $BB_1$, $BB_2$, $BB_3$, $B_1$, $B_2$, $CB_1$, $CB_2$, CCR1, CCR2, CCR3, CCR4, CCR5, CCR6, CCR7, CCR8, CCR9, CCR10, CXCR1, CXCR2, CXCR3, CXCR4, CXCR5, CXCR6, $CX_3CR1$, XCR1, ACKR1, ACKR2, ACKR3, ACKR4, CCRL2, $CCK_1$, $CCK_2$, GPR1, GPR3, GPR4, GPR42, GPR6, GPR12, GPR15, GPR17, GPR18, GPR19, GPR20, GPR21, GPR22, GPR25, GPR26, GPR27, GPR31, GPR32, GPR33, GPR34, GPR35, GPR37, GPR37L1 GPR39, GPR45, GPR50, GPR52, GPR55, GPR61, GPR62, GPR53, GPR65, GPR68, GPR75, GPR79, GPR82, GPR83, GPR6, GPR84, GPR15, GPR85, GPR87, GPR88, GPR101, GPR119, GP132, GPR139, GPR141, GPR142, GPR146, GPR148, GPR149, GPR150, GPR151, GPR152, GPR153, GP60, GPR161, GPR162, GPR171, GPR173, GPR174, GPR176, GPR182, GPR183, LGR4, LGR5, LGR6, MAS1, MAS1L, MRG-PRD, MRGPRE, MRGPRF, MRGPRG, MRGPRX1, MRG-PRX2, MRGPRX3, MRGPRX4, OPN3, OPN4, OPN5, P2RY8, P2RY10, TAAR2, TAAR3, TAAR4P, TAAR5, TAAR6, TAAR8, TAAR9, C3a, $C5a_1$, $C5a_2$, $D_1$, $D_2$, $D_3$, $D_4$, $D_5$, $ET_A$, $ET_B$, FPR1, FPR2/ALX, FPR3, FFA1, FFA2, FFA3, $GAL_1$, $GAL_2$, $GAL_3$, Ghrelin Receptor, FSHR, LHR, TSHR, $GnRH_1$, $GnRH_2$, GPER, $H_1$, $H_2$, $H_3$, $H_4$, Kisspeptin Receptor, $BLT_1$, $BLT_2$, $CysLT_1$, $CysLT_2$, OXER, $LPA_1$, $LPA_2$, $LPA_3$, $LPA_4$, $LPA_5$, $LPA_6$, $S1P_1$, $S1P_2$, $S1P_3$, $S1P_4$, $S1P_5$, $MCH_1$, $MCH_2$, $MC_1$, $MC_2$, $MC_3$, $MC_4$, $MC_5$, $MT_1$, $MT_2$, Motilin Receptor, NMU1, NMU2, NPFF1, NPFF2, NPBW1, NPBW2, $Y_1$ receptor, $Y_2$ receptor, $Y_3$ receptor, $Y_4$ receptor, $Y_5$ receptor, $Y_6$ receptor, $NTS_1$, $NTS_2$, δ opioid receptor, κ opioid receptor, μ opioid receptor, NOP receptor, $OX_1$ receptor, $OX_2$ receptor, Oxoglutarate Receptor, $P2Y_1$, $P2Y_2$, $P2Y_4$, $P2Y_6$, $P2Y_1$, $P2Y_{12}$, $P2Y_{13}$, $P2Y_{14}$, $PKR_1$, $PKR_2$, PrRP, $DP_1$, $DP_2$, $EP_1$, $EP_2$, $EP_3$, $EP_4$, FP, IP, TP, PAR1, PAR2, PAR3, PAR4, QRFP receptor, RXFP1, RXFP2, RXFP3, RXFP4, $sst_1$ receptor, $sst_2$ receptor, $sst_3$ receptor, $sst_4$ receptor, $sst_5$ receptor, $NK_1$ receptor, $NK_2$ receptor, $NK_3$ receptor, $TRH_1$ receptor, $TRH_2$ receptor, TA receptor, UT receptor, $V_{1A}$ receptor, $V_{1B}$ receptor, $V_2$ receptor, or OT receptor. The small molecules may have known or suspected targets that are Class B G-protein coupled receptors, including, but not limited to: CT receptor, $AMY_1$ receptor, $AMY_2$ receptor, $AMY_3$ receptor, CGRP receptor, $AM_1$ receptor, $AM_2$ receptor, $CRF_1$ receptor, $CRF_2$ receptor, GHRH, GIP, GLP-1 receptor, GLP-2 receptor, Glucagon receptor, Secretin receptor, PTH1 receptor, PTH2 receptor, $PAC_1$ receptor, $VPAC_1$ receptor, or $VPAC_2$ receptor. The small molecules may have known or suspected targets that are Class C G-protein coupled receptors, including, but not limited to: CaS receptor, $GPRC_6$ receptor, $GABAB_{B1}$ receptor, $GABAB_{B2}$ receptor, $GABAB_B$ receptor, $mGlu_1$ receptor, $mGlu_2$ receptor, $mGlu_3$ receptor, $mGlu_4$ receptor, $mGlu_5$ receptor, $mGlu_6$ receptor, $mGlu_7$ receptor, or $mGlu_8$ receptor. The small molecules may have known or suspected targets that are Class Frizzled G-protein coupled receptors, including, but not limited to: $FZD_1$, $FZD_2$, $FZD_3$, $FZD_4$, $FZD_5$, $FZD_6$, $FZD_7$, $FZD_8$, $FZD_9$, $FZD_{10}$, or SMO. The small molecules may have known or suspected targets that are Class Adhesion G-protein coupled receptors, including, but not limited to: ADGRA1, ADGRA2, ADGRA3, ADGRB1, ADGRB2, ADGRB3, CELSR1, CELSR2, CELSR3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRTG1, ADGRG2, ADGRG3, ADGRG4, ADGRG5, ADGRG6, ADGRG7, ADGRL1, ADGRL2, ADGRL3, ADGRL4, or ADGRV1.

According to the methods provided herein, small molecules that are known or suspected to target networks and pathways related to muscle development may be used for drug screening assays. The small molecules may have known or suspected targets that include, but are not limited to PARP1 and PARP2.

According to the methods provided herein, small molecules that are known or suspected to target networks and pathways related to muscle development may be used for drug screening assays. The small molecules may have known or suspected targets in the Wnt/Frizzled/β-catenin signaling pathways including but not limited to multiple isoforms of Wnt ligands including but not limited to Wnt3a, Wnt5a, Wnt9, WIF, sFRP, Kremens, N-cadherin, LRP5/6/Frizzled, RYK/RORα/β/γ, Dkk, multiple isoforms of CK1, GSK3α/β, multiple isoforms of PKC, multiple isoforms of PLC, RhoA, Rac1, ROCK1/2, multiple isoforms of PDEs, Src, CamKI/II, β-catenin or β-catenin/transcription factor(s) interface as exemplified but not limited to Apc, Tcf-1, Tcf-4, Bcl-9, TANK1/2, TAK-1, NLK, multiple isoforms of JNK, multiple isoforms of p38, MKK3/6, multiple isoforms of PPAR.

According to the methods provided herein, small molecules that are known or suspected to target networks and pathways related to muscle development may be used for drug screening assays. The small molecules may have known or suspected targets involved in telomere structure and telomerase activity.

According to the methods provided herein, small molecules that are known or suspected to target networks and pathways related to muscle development may be used for drug screening assays. The small molecules may have known or suspected targets that are involved in cytoskeleton structure and/or JAK/STAT signaling, including, but not limited to: IGF1R/InR, PI3K, Akt, mTOR, PKCs, Srk, FAK, Raf, MEK, ERK, ROCK kinases, laminins, agrin, dystroglycans, neurexin, sarcoglycans, integrins, syntrophins, dystrobrevin, dystrophin, actin, NMDA/Ca2+, Tyk, JAK, p38, Pim1, Bcl-2, c-Myc, and Cdks.

According to the methods provided herein, small molecules that are known or suspected to target networks and pathways related to muscle development may be used for drug screening assays. The small molecules may have known or suspected targets that are involved in apoptosis, including, but not limited to: TNF-a, IKKa/b, NFkB, Survivin, cIAP, Caspases 3/8/9, p53/Mdm2, JAK/STAT, PKC, Ras, Raf, ERK1/2, JNK, Bcl-2, Bcl-xL PI3K, Akt, DNA-PK, mTOR, p70S6K, and ATM.

According to the methods provided herein, small molecules that are known or suspected to target networks and pathways related to muscle development may be used for drug screening assays. The small molecules may have known or suspected targets that are involved in ubiquitin signaling, including, but not limited to: the proteasome, DUBs, E1 activating enzymes, E2 conjugating enzymes, and E3-ligases.

C. Drug Therapies

The compounds disclosed herein may, in some cases, be used as a drug therapy to treat a subject with a muscle deficiency. The compounds may promote myogenesis and/or muscle regeneration in vivo.

The compounds disclosed herein can be used along with non-drug therapies (e.g. as an adjunct), as a monotherapy, or as part of a combination therapy. In some cases, the compounds disclosed herein (e.g. Chk1 inhibitors, mTOR inhibitors, Raf inhibitors, MEK inhibitors, mAChR agonists, mAChR antagonists) are administered alongside a cell therapy (e.g. transplanted pluripotent stem cells, satellite, satellite-like, myoblast, myoblast-like, myotube, or myotube-like cells). In some cases, the compounds may enhance the yield or rate of differentiation of the cells to myoblasts transplanted into the subject. In some cases, the compounds may enhance engraftment of the transplanted cells or fusion of the transplanted cells with native myotubes in the subject. In other cases, the compounds disclosed herein (e.g. Chk1 inhibitors, mTOR inhibitors, Raf inhibitors, MEK inhibitors, mAChR agonists, mAChR antagonists) are administered as a monotherapy without the transplantation of cells into the subject. In some cases, the compounds may enhance the differentiation of native satellite cells or myoblasts into myotubes. Subjects (e.g. patients with genetic diseases affecting muscular function, or subjects suffering from non-genetic muscle dysfunction) may be treated with any of the compounds described herein to enhance myotube structure or function or to improve muscle function. In some embodiments, the subject is treated with a Chk1 inhibitor (e.g. CHIR-124). In other embodiments, the subject is treated with an mTOR inhibitor (e.g. rapamycin). In other embodiments, the subject is treated with a Raf inhibitor (e.g. sorafenib). In other embodiments, the subject is treated with a MEK inhibitor (e.g. MEK162). In other embodiments, the subject is treated with a GPR119 agonist (e.g. GSK1292263). In other embodiments, the subject is treated with an S1P1 agonist (e.g. TC-G 1006). In other embodiments, the subject is treated with a mAChR agonist (e.g. pilocarpine). In other embodiments, the subject is treated with a mAChR antagonist (e.g. atropine). In other embodiments, the subject is treated with a PARP inhibitor (e.g. talazoparib).

In some particular cases, checkpoint inhibitors, particularly Chk1 inhibitors (e.g., CHIR-124), are used to enhance or promote production of mature myotubes in a subject, as described herein. In some cases, the Chk 1 inhibitor (e.g., CHIR-124) is administered to a subject to promote mature myotube formation in vivo. In some embodiments, the Chk 1 inhibitor (e.g., CHIR-124) is administered via a suitable method to achieve a local concentration of about 0.10 µM to about 1 µM (e.g., 0.25 µM, 0.50 µM) to enhance or promote production of mature myotubes in vivo. The local concentration may be, for example, the concentration of the compound at or near a site (e.g., muscle tissue) intended to be treated by the therapy.

In some particular embodiments, the Chk 1 inhibitor (e.g., CHIR-124) is administered in a 100 mg dose once daily to a subject (e.g., human subject) to enhance or promote production of mature myotubes in the subject. In some embodiments, the Chk 1 inhibitor (e.g., CHIR-124) is administered in a 100 mg dose to a subject, but at a different frequency, such as once every other day. In some embodiments, the Chk 1 inhibitor (e.g., CHIR-124) is administered in a 50-75 mg dose. In some cases, such dose is administered twice daily to a subject (e.g., human subject) to enhance or promote production of mature myotubes in the subject.

Chk1 inhibitors used herein for drug therapies may have different chemical structures or different scaffolds. In some embodiments, a Chk1 inhibitor as described herein is a quinolinone Chk1 inhibitor, such as CHIR-124. Synthesis of quinolinone Chk1 inhibitors has been described elsewhere, e.g. in Li et al. Bioorg Med Chem Lett. 2006 Jun. 15; 16(12):3121-4 and in U.S. Pat. Nos. 7,825,132B2, 7,838,527B2, 7,470,709B2, and US 20050256157A1. In some embodiments, a Chk1 inhibitor as described herein is a quinolinone Chk1 inhibitor according to formula (I):

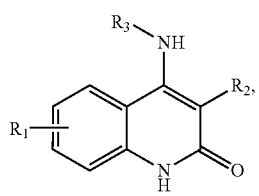

(I)

or a salt thereof, wherein
R1 is selected from methyl, fluoro, chloro, trifluoromethyl, and difluoromethyl;

R2 is selected from benzimidazolyl, benzoxazolyl, benzothiazolyl, 3H-indolyl, benzofuryl, benzothiophenyl, and 1H-indenyl; and
R3 is selected from quinuclidinyl and 1,4-diazabicyclo [2.2.2]octanyl.

In some embodiments, a Chk1 inhibitor as described herein is a quinolinone Chk1 inhibitor according to formula (II):

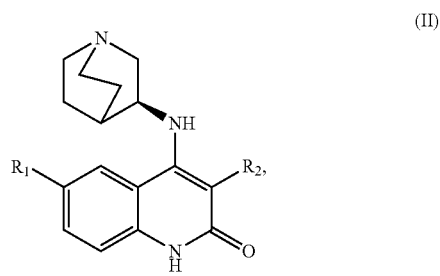

(II)

or a salt thereof, wherein
R1 is selected from methyl, halogen, and halomethyl; and
R2 is a 5+6 bicyclic fused ring system containing 0-4 heteroatoms independently selected from O, S or N.

In some embodiments, a Chk1 inhibitor as described herein is a quinolinone Chk1 inhibitor according to formula (III):

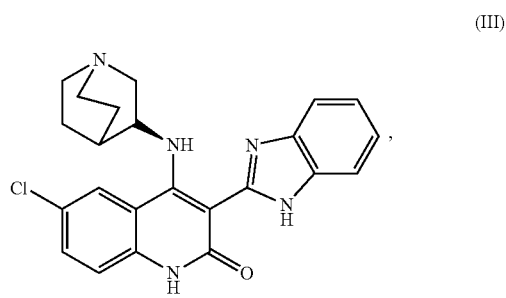

(III)

or a salt thereof (CHIR-124).

In some embodiments, Chk1 inhibitors are not quinolinones. Other cases of scaffolds or exemplary molecules that inhibit Chk1 include pyrazolo[1,5-a]pyrimidines (e.g. MK-8776/SCH900776), thiophenecarboxamide ureas (e.g. AZD7762), pyrizinyl ureas (e.g. LY2603618) and PF 477736.

Any of the compounds provided herein (including the checkpoint inhibitors and other compound described herein) may be administered to a subject in combination with a cell therapy. The effects of the combination may be additive; in some cases, the effects of the combination are synergistic. The compounds may be administered before, during or after the administration of the cell therapy. In some cases, the compounds are administered separately from the cell therapy. In some cases, the cell therapy is mixed with one or more of the compounds. In some particular examples, the cell therapy may involve introducing myotube-precursor cells (e.g., embryonic stem cells, iPSCs, satellite cells, satellite-like cells, myoblasts, or myoblast-like cells), mature myotubes or myotube-like cells into the subject and the compound may aid with the grafting of the cells, or with the differentiation of myoblasts. In other examples, the cell therapy may involve introducing myoblasts or myoblast-like cells into a subject and a compound provided herein (e.g., checkpoint inhibitor, Chk 1 inhibitor, CHIR-124) is also administered into the subject in order to promote in vivo generation of myotubes or myotube-like cells from the introduced myoblasts or myoblast-like cells.

The compounds of the current disclosure may be administered by any of the accepted modes of administration of agents having similar utilities, for example, by cutaneous, oral, topical, intradermal, intrathecal, intravenous, subcutaneous, intramuscular, intra-articular, intraspinal or spinal, nasal, epidural, rectal, vaginal, or transdermal/transmucosal routes. The most suitable route will depend on the nature and severity of the condition being treated. Subcutaneous, intradermal and percutaneous injections can be routes for the compounds of this disclosure. Sublingual administration may be a route of administration for compounds of this disclosure. Intravenous administration may be a route of administration for compounds of this disclosure. In a particular example, the pharmaceutical composition provided herein may be administered to a patient orally.

A pharmaceutical composition (e.g., for oral administration or for injection, infusion, buccal delivery, subcutaneous delivery, intramuscular delivery, intraperitoneal delivery, sublingual delivery, or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the compounds or agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in a pharmaceutical composition may be formulated for oral delivery with a flavoring agent, e.g., in a liquid, solid or semi-solid formulation and/or with an enteric coating. In some cases, the compounds of this disclosure may be solubilized and encapsulated (e.g., in a liposome or a biodegradable polymer), or used in the form of microcrystals coated with an appropriate nontoxic lipid.

A pharmaceutical composition comprising any one of the compounds or agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

In some cases, administering a compound herein to a patient may comprise administering a daily dose of greater than 0 mg/m$^2$, 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 100 mg/m$^2$, 150 mg/m$^2$, 200 mg/m$^2$, 300 mg/m$^2$, 350 mg/m$^2$, 400 mg/m$^2$, 450 mg/m$^2$, 500 mg/m$^2$, 750 mg/m$^2$, 1000 mg/m$^2$, 1250 mg/m$^2$, 1500 mg/m$^2$, 1750 mg/m$^2$, or 2000 mg/m$^2$ of a compound to a subject.

In some cases, administering a compound herein to a patient may comprise administering a daily dose of 0.1 mg/m$^2$, 0.2 mg/m$^2$, 0.3 mg/m$^2$, 0.4 mg/m$^2$, 0.5 mg/m$^2$, 0.6 mg/m$^2$, 0.7 mg/m$^2$, 0.8 mg/m$^2$, 0.9 mg/m$^2$, 1 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3 mg/m$^2$, 3.1 mg/m$^2$, 3.2 mg/m$^2$, 3.3 mg/m$^2$, 3.4 mg/m$^2$, 3.5 mg/m$^2$, 3.6 mg/m$^2$, 3.7 mg/m$^2$, 3.8 mg/m$^2$, 3.9 mg/m$^2$, 4 mg/m$^2$, 4.1 mg/m$^2$, 4.2 mg/m$^2$, 4.3 mg/m$^2$, 4.4 mg/m$^2$, 4.5 mg/m$^2$, 4.6 mg/m$^2$, 4.7 mg/m$^2$, 4.8 mg/m$^2$, 4.9 mg/m$^2$, 5 mg/m$^2$, 5.1 mg/m$^2$, 5.2 mg/m$^2$, 5.3 mg/m$^2$, 5.4 mg/m$^2$, 5.5 mg/m$^2$, 5.6 mg/m$^2$, 5.7 mg/m$^2$, 5.8 mg/m$^2$, 5.9 mg/m$^2$, 6 mg/m$^2$, 6.1 mg/m$^2$, 6.2 mg/m$^2$, 6.3 mg/m$^2$, 6.4 mg/m$^2$, 6.5 mg/m$^2$, 6.6 mg/m$^2$, 6.7 mg/m$^2$, 6.8 mg/m$^2$, 6.9 mg/m$^2$, 7 mg/m$^2$, 7.1 mg/m$^2$, 7.2 mg/m$^2$, 7.3 mg/m$^2$, 7.4 mg/m$^2$, 7.5 mg/m$^2$, 7.6 mg/m$^2$, 7.7 mg/m$^2$, 7.8 mg/m$^2$, 7.9 mg/m$^2$, 8 mg/m$^2$, 8.1 mg/m$^2$, 8.2 mg/m$^2$, 8.3 mg/m$^2$, 8.4 mg/m$^2$, 8.5 mg/m$^2$, 8.6 mg/m$^2$, 8.7 mg/m$^2$, 8.8 mg/m$^2$, 8.9 mg/m$^2$, 9 mg/m$^2$, 9.1 mg/m$^2$, 9.2 mg/m$^2$, 9.3 mg/m$^2$, 9.4 mg/m$^2$, 9.5 mg/m$^2$, 9.6 mg/m$^2$, 9.7 mg/m$^2$, 9.8 mg/m$^2$, 9.9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 51 mg/m$^2$, 52 mg/m$^2$, 53 mg/m$^2$, 54 mg/m$^2$, 55 mg/m$^2$, 56 mg/m$^2$, 57 mg/m$^2$, 58 mg/m$^2$, 59 mg/m$^2$, 60 mg/m$^2$, 61 mg/m$^2$, 62 mg/m$^2$, 63 mg/m$^2$, 64 mg/m$^2$, 65 mg/m$^2$, 66 mg/m$^2$, 67 mg/m$^2$, 68 mg/m$^2$, 69 mg/m$^2$, 70 mg/m$^2$, 71 mg/m$^2$, 72 mg/m$^2$, 73 mg/m$^2$, 74 mg/m$^2$, 75 mg/m$^2$, 76 mg/m$^2$, 77 mg/m$^2$, 78 mg/m$^2$, 79 mg/m$^2$, 80 mg/m$^2$, 81 mg/m$^2$, 82 mg/m$^2$, 83 mg/m$^2$, 84 mg/m$^2$, 85 mg/m$^2$, 86 mg/m$^2$, 87 mg/m$^2$, 88 mg/m$^2$, 89 mg/m$^2$, 90 mg/m$^2$, 91 mg/m$^2$, 92 mg/m$^2$, 93 mg/m$^2$, 94 mg/m$^2$, 95 mg/m$^2$, 96 mg/m$^2$, 97 mg/m$^2$, 98 mg/m$^2$, 99 mg/m$^2$, or 100 mg/m$^2$ of the compound.

The daily dose of can be greater than 0 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 150 mg, 200 mg, 300 mg, 350 mg, 400 mg, 450 mg, 500 mg, 750 mg, 1 g, 5 g, 10 g, or higher.

In some cases, the daily dose may be administered in a single dose. In some cases, the daily dose may be divided into 1, 2, 3, 4, 5, 6, 7, 8, 9, or 10 doses per day. For example, the daily dose can be divided into 3 doses per day. In some cases, the daily dose of the chemotherapeutic drug may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a chemotherapeutic drug may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours.

The compounds described herein may be administered to a patient one or more times per day. In some cases, the compounds may be administered to a patient one time per day. In some cases, the compounds may be administered to a patient at least 2 times, 3 times, 4 times 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, or 24 times per day. For example, a compound may be administered to a patient 3 times per day.

The compound described herein may be administered to a patient for one or more days. In some cases, the compound may be administered to a patient for one day. In some cases, the pharmaceutical composition may be administered to the patient for at least 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, or 50 years.

The compounds described herein may be effective over time. In some cases, the compounds may be effective for one or more days. In some cases, the duration of efficacy of the compounds is over a long period of time. In some cases, the efficacy of the compound may be greater than 2 days, 3 days, 4 days, 5 days, 6 days, 1 week, 2 weeks, 3 weeks, or 1 month.

The compounds of the current disclosure, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diasteroisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Compounds may be dosed in their enantiomerically pure form. In some examples, the compound has an enantiomeric excess greater than about 50%, 60%, 70%, 80%, 90%, 95%, 96%, 97%, 98%, or 99%. Compounds may be dosed in their diasteriomerically pure form. In some examples, the compound has a diasteriomeric excess greater than about 50%, 60%, 70%, 80%, 90%, 95%, 96%, 97%, 98%, or 99%.

Stereocenters may be defined using the Cahn-Ingold-Prelog priority rules. Compounds may have stereocenters in the R-configuration. Compounds may have stereocenters in the S-configuration.

Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

In certain particular embodiments, more than one compound of the current disclosure may be administered at a time to a subject. In some embodiments, two compounds of the current disclosure in combination make act synergistically or additively, and either compound may be used in a lesser amount than if administered alone.

In certain embodiments, compounds disclosed herein and/or pharmaceutical compositions thereof can be used in combination therapy with other therapeutic agents. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent. In other embodiments, compounds disclosed herein and/or pharmaceutical compositions thereof are administered prior or subsequent to administration of other therapeutic agents.

The compounds of the present disclosure, or their pharmaceutically acceptable salts, are generally administered in a therapeutically effective amount. The amount of the compound actually administered may be determined by a physician or caregiver, in the light of the relevant circumstances, including the condition to be treated, the chosen route of administration, the compound administered and its relative activity, the age, weight, the response of the individual patient, the severity of the patient's symptoms, and the like.

The present disclosure further provides salts of any compound described herein. The term "salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p toluenesulfonic acid, salicylic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like.

Acid addition salts can arise from the addition of an acid to a compound described herein. In some cases, the acid can be organic. In some cases, the acid can be inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccharate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, caesium, cerium, magnesium, manganese, iron, calcium, strontium, cobalt, titanium, aluminium, copper, cadmium, and zinc.

Non-limiting examples of suitable metal salts include a lithium salt, a sodium salt, a potassium salt, a caesium salt, a cerium salt, a magnesium salt, a manganese salt, an iron salt, a calcium salt, a strontium salt, a cobalt salt, a titanium salt, an aluminium salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts can be a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

The term "therapeutically effective amount" may generally refer to the amount (or dose) of a compound or other therapy that is minimally sufficient to prevent, reduce, treat or eliminate a condition, or risk thereof, when administered to a subject in need of such compound or other therapy. In some instances the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which may be determined by one of ordinary skill in the art.

The pharmaceutical compositions disclosed herein may be any type of formulation including solid formulations. In some cases the solid formulation (or other type of formulation) comprises at least 0.01 mg, 0.1 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of In some cases, the liquid formulation may comprise at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml In some cases, a pharmaceutical composition or formulation described herein may comprise a combination of different agents. In some cases, a pharmaceutical composition described herein may comprise at least 2 agents. The molar ratio of one agent to at least one other protective agent can be about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:1,000, about 1:10,000, or about 1:>10,000.

In some cases, the pharmaceutical compositions disclosed herein may be assembled into kits. In some cases, the kit can comprise one or more compounds provide herein. In some cases, the kit may also comprise instructions for use. The kit may also comprise vials, tubes, needles, packaging, or other material.

Kits with unit doses of one or more of the compounds described herein, usually in oral or injectable doses, are provided. Such kits may include a container containing the unit dose, an informational package insert describing the use and attendant benefits of the drugs in treating the disease, and optionally an appliance or device for delivery of the composition.

The kit may further comprise any device suitable for administration of the composition. For example, a kit comprising an injectable formulation of pharmaceutical compositions may comprise a needle suitable for subcutaneous administration and an alcohol wipe for sterilization of the injection site.

In some cases, kits may be provided with instructions. The instructions may be provided in the kit or they may be accessed electronically (e.g., on the World Wide Web). The instructions may provide information on how to use the compositions of the present disclosure. The instructions may further provide information on how to use the devices of the present disclosure. The instructions may provide information on how to perform the methods of the disclosure. In some cases, the instructions may provide dosing information. The instructions may provide drug information such as the mechanism of action, the formulation of the drug, adverse risks, contraindications, and the like. In some cases, the kit is purchased by a physician or health care provider for administration at a clinic or hospital. In some cases, the kit is purchased by a laboratory and used for screening candidate compounds.

VIII. Some Definitions

As used herein, the term "or" is used to refer to a nonexclusive or, such as "A or B" includes "A but not B," "B but not A," and "A and B," unless otherwise indicated.

As used herein, the term "about" when referring to a number or a numerical range means that the number or numerical range referred to is an approximation within experimental variability (or within statistical experimental error), and thus the number or numerical range may vary from, for example, between 1% and 15% of the stated number or numerical range. In examples, the term "about" refers to ±10% of a stated number or value.

As used herein, the terms "treat," "ameliorate," "treatment," and "treating" are used interchangeably. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For a prophylactic benefit, a compound provided herein and/or cells (e.g., myotube precursor cells, myoblasts, myoblast-like cells, satellite cells, satellite-like cells, the myotubes or myotube-like cells) may be administered to a patient at risk of developing a particular disease, or to a patient reporting one or more of the physiological symptoms of a disease, even though a diagnosis of this disease may not have been made.

IX. Examples

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1: Screening for Myogenic Induction Conditions

Human pluripotent stem cells (hPSC) were expanded feeder-free on collagen I-coated surfaces using commercially available M2 culture medium (manufactured by Genea Biocells) and following standard protocols. This method dissociates cultures to single cells at each passage. Batches of each cell line were frozen in M2 medium plus 10% DMSO following standard protocols. Each batch was quality control tested for viability, morphology, sterility, karyotype, DNA fingerprint, pluripotency marker expression (Oct4, Nanog, SSEA-4, Tra1-60) and Pluritest (Müller et al., 2011).

Commercially available hESC cell lines GENEA017 and GENEA020 were used to screen for myogenic induction culture conditions. Basal culture medium was prepared by adding Skeletal Muscle Cell Growth Medium Supplement Mix (manufactured by Promocell) to Skeletal Muscle Cell Basal Medium (manufactured by Promocell) according to the manufacturer's instructions to produce a medium similar to MCDB120 (U.S. Pat. No. 5,143,842), to which Rho-associated kinase inhibitor Y27632 (10 μM) was also added. Cells were cultured in 384-well optical bottom microtiter plates coated with collagen I (100 μg/mL), hFibronectin (10 μg/mL), mLaminin (5 μg/mL) or hFibronectin (10 μg/mL) with mLaminin (5 μg/mL).

To screen for myogenic induction culture conditions, the cell lines were dissociated to single cells and plated in 20 μL of basal culture medium at a density of $8\times10^3$ cells/cm$^2$ in the 384-well plates. Compounds from Table 1 were added to basal culture medium in combinations of two (for a total of 378 combinations) in a 384-deep-well plate at 2× the final concentration. 20 μL of this compound-supplemented medium was added to the cultured cells in order to culture the cells in 40 μL of culture medium containing the compounds at their final concentrations. The cells were cultured at 37° C., 5% $CO_2$ and 5% $O_2$ for nine days. Media was changed every other day while maintaining the concentration of compounds being screened at their final concentration.

At the end of the culture period, cells were fixed with 4% formalin solution, immunofluorescence stained for satellite cell markers Pax3, Pax7 and CD56 and analyzed by high-content imaging. None of the cells grown only in basal medium exhibited staining for satellite-cell markers. Of the 378 conditions screened, 34 were highly toxic to the cells. Four conditions resulted in cells that were positive for CD56 but negative for both Pax3 and Pax7. Fifteen of the conditions tested resulted in more than 50% of the cells exhibiting satellite-cell characteristics and positive staining for CD56, Pax3 and Pax7. Cells were further stained for myoblast marker MyoD, but no positive cells were observed, indicating that the satellite cells had not further differentiated to myoblasts.

TABLE 1

| Compounds used in screen | | |
|---|---|---|
| # | Compound/Component | Final Concentration |
| 1 | Retinoic acid | 3 nM |
| 2 | dbcAMP | 1 mM |
| 3 | Creatine | 1 mM |
| 4 | Noggin | 100 ng/mL |
| 5 | IGF-1 | 10 ng/mL |
| 6 | Activin A | 6 ng/mL |
| 7 | Transferrin | 150 μg/mL |
| 8 | FGF | 20 ng/mL |
| 9 | Horse serum | 5% |
| 10 | XAV939 | 2.5 μM |
| 11 | VEGF | 25 ng/mL |
| 12 | 5-azacytidine | 10 mM |
| 13 | CHIR99021 | 3 μM |
| 14 | Forskolin | 100 μM |
| 15 | DAPT | 10 μM |
| 16 | Valproic acid (VPA) | 0.5 μM |
| 17 | PD173074 | 0.02 μM |
| 18 | SU5402 | 10 μM |
| 19 | SMO antagonist | 0.5 μM |
| 20 | Ascorbic Acid | 200 μM |
| 21 | BMP4 | 10 ng/mL |
| 22 | Alk5 inhibitor | 2 μM |
| 23 | SB431542 | 2 μM |
| 24 | BIX01294 | 1 μM |
| 25 | PD0325901 | 0.5 μM |
| 26 | PD169316 | 5 μM |
| 27 | sodium butyrate | 250 μM |
| 28 | blank | Medium w/o compound |

Example 2: Myogenic Conditions are not Critically Dependent on Serum, Growth Factors, or Specific Basal Media Satellite cells were prepared from GENEA002, GENEA019 and GENEA020 as described in Example 1 using the combination of CHIR99021 and Alk5 inhibitor identified in Example 1 while varying the composition of the basal medium. The components of the Skeletal Muscle Cell Growth Medium Supplement were kept at their final concentration (e.g. 50 μg/mL bovine fetuin, 10 ng/mL EGF, 1 ng/mL bFGF, 10 μg/mL insulin and 0.4 μg/mL dexamethasone) and the basal medium and serum listed in Table 2 were mixed in combinations of two. Pax3, Pax7 and CD56 positive satellite-like cells were obtained under all conditions. However, cell viability was poor in the absence of serum or albumin. The cell density was dependent on media and serum component used, indicating that differentiation is robust across different conditions and the effect of media is largely on cell viability. The proportion of positive cells, cell expansion, and robustness across all cell lines varied. The Promocell and Lonza 1 basal media performed very similarly; both media are based on MCDB120. Horse serum appeared to support differentiation most consistently for all cell lines.

TABLE 2

Basal media and serum components tested

| # | Basal Media |
|---|---|
| 1 | Promocell 'Skeletal Muscle Cell Basal Medium' (Promocell) |
| 2 | Lonza 'SkBM Basal Medium' (Lonza 1) |
| 3 | Lonza 'SkBM-2 Basal Medium' (Lonza 2) |
| 4 | Stem Cell Technologies 'APEL Medium' (APEL) |
| 5 | DMEM/F12 |

| # | serum component |
|---|---|
| 1 | 5% fetal bovine serum (FBS) |
| 2 | 2.5% horse serum (HS) |
| 3 | 5% human serum albumin |
| 4 | 2.5% PLT-Max human platelet extract |
| 5 | 1.8% bovine serum albumin |
| 6 | 5% knock-out serum replacement (KOSR) |
| 7 | no serum |

Next, the dependence on the components of the Skeletal Muscle Cell Growth Medium Supplement was tested by differentiating GENEA019 in MCDB120-like basal medium supplemented with CHIR99021 and Alk5 inhibitor, but in which one of the components of the Skeletal Muscle Cell Growth Medium Supplement (50 µg/ml bovine fetuin, 10 ng/ml EGF, 1 ng/ml bFGF, 10 µg/ml insulin and 0.4 µg/ml dexamethasone) had been omitted or, in the case of 5% horse serum, replaced with 1.5% Albumax (bovine serum albumin manufactured by Life Technologies). Satellite-like cells positive for Pax3, Pax7 and CD56 were obtained under each condition, demonstrating that no single growth factor is required for myogenic induction. Differentiation was largely similar across all conditions, indicating that no one serum component is critical for differentiation.

Example 3: Preparation of Satellite Cells from Pluripotent Stem Cells Using CHIR99021 (3 µM) and Alk5 Inhibitor (2 µM) as Contributing Components Cultures of hPSC were grown as described in Example 1 in basal medium supplemented with CHIR99021 (3 µM) and Alk5 inhibitor (2 µM) to induce differentiation. Cells that had been differentiated were fixed and immunostained for satellite cell markers Pax3, Pax7 and CD56. While no positive cells were observed in cells cultured in basal medium only, those cultured in basal medium supplemented with CHIR99021 (3 µM) and Alk5 inhibitor (2 µM) resulted in >50% of cells positively staining for said markers. These satellite-like cells were produced in all extracellular matrices tested, although hFibronectin produced the highest levels of satellite-like cells. Cells were further stained for myoblast marker MyoD, but no positive cells were identified, indicating that the cells had not further differentiated to myoblasts.

Example 4: Stem Cell Culture and Skeletal Muscle Differentiation

In this example, human embryonic stem cell lines listed in Table 3 were differentiated into satellite-like cells, myoblasts and myotubes. Stem cell lines were cultured in commercially available media, mTeSR (Stem Cell Technologies) or M2 (Genea Biocells) and dissociated into single cells using Passaging Solution (Genea Biocells). Cells were plated in Myogenic Induction Medium (MCDB 120 base medium, 5% Horse Serum, 50 µg/mL Fetuin (Bovine), 10 ng/mL hr-EGF, 10 µg/mL Insulin (Human), 0.4 µg/mL Dexamethasone, 10 µM Rock Inhibitor (Y-27632-dihydrochloride), 50 µg/mL Ascorbic Acid (Vitamin C), 2 µM SB431542, 20 ng/mL HGF, 1 ng/mL hr-bFGF, 10 ng/mL IGF1, 10 ng/mL Oncostatin M, 10 ng/mL PDGF) to induce myogenic differentiation and incubated at 37° C. and 5% $CO_2$ for 7 to 10 days while performing media changes every other day. Once confluent, cells were dissociated into single cells using Passaging Solution. These satellite-like cells were frozen at 3 million cells per ml and per cryovial in Myogenic Induction Medium supplemented with 10% DMSO. Vials were cooled slowly to −80° C. and then transferred to liquid nitrogen for long-term storage. Alternatively, instead of freezing, satellite-like cells were plated in Myoblast Medium (Genea Biocells) in collagen I-coated culture flasks or plates and cultured for 7-10 days at 37° C. and 5% $CO_2$ with media changes performed every other day until confluency was reached. At that stage the resulting cells (myoblast cultures) were either switched to Myotube Medium (Genea Biocells) for further differentiation or were dissociated into single cells using Passaging Solution for freezing at 3 million cells per ml and per cryovial in Myoblast Medium supplemented with 10% DMSO. Vials were cooled slowly to −80° C. and then transferred to liquid nitrogen for long-term storage.

TABLE 3

Human embryonic stem cell lines.

| line | karyotype |
|---|---|
| GENEA019 | 46, XX |
| GENEA002 | 46, XY |

Example 5: Assembly of Chemical Compound Libraries

Compounds that target known/suspected epigenetic modifying enzymes as well as many additional targets, pathways, and networks, including but not limited to kinome, Wnt/Fzd/b-catenin, apoptosis, cytoskeletal signaling, cell cycle, DNA repair, and G-protein coupled receptor were assembled into libraries. Lead-like compounds were obtained from several commercial providers including MedChem Express, Tocris and Selleck Chemicals. Together they represent about 5,000 modulators of known and suspected proteins and other targets relevant to myotube maintenance and/or neuromuscular biology.

TABLE 4

Representative biologically diverse chemical series tested

| BioDiverse Set COMPOUND | TARGET | Epigenetics Set COMPOUND | TARGET |
|---|---|---|---|
| Dasatinib | Src | GSK J4 | JMJD3 and UTX |
| PD173074 | FGFR1/3 | GSK J1 | JMJD3 (KDM6B) and UTX (KDM6A), |
| RO4929097 | Notch | OG-L002 | LSD1 |
| Thiazovivin (TAV) | ROCK | IOX1 | IOX1 |
| Tacrolimus | PP2B | GSK-LSD1 | LSD1 |
| Amiodarone | IC blocker | ML324 | JMJD2 |
| Forskolin | PKA Act | Anacardic Acid | p300/CBP |
| TTNPB | RAR | Decitabine | DNA methylation |
| LDE225 Diphosphate | Hh | Azacitidine | DNA methylation |
| MLNM4924 | NAE | RG108 | DNA methyltransferase |
| 17-AAG | HSP90 | Thioguanine | DNMT1 |
| KY02111 | Wnt | Zebularine | DNA methylation |
| CHIR-99021 | GSK3b | Lomeguatrib | $O^6$-alkylguanine-DNA-alkyltransferase |
| PD98059 | MEK | Procainamide | DNA methyltransferase inhibitor |
| GW788388 | Alk5 | EPZ5676 | DOT1L |
| AR-42 | Epi | EPZ005687 | EZH2 |
| EPZ-6438 | Epi | GSK343 | EZH2 |
| Indomethacin | Notch | BIX 01294 | G9a histone methyltransferase |
| IOX2 | HIF-1a | EPZ-6438 | EZH2 |
| PluriSlnl | SCD1 (desaturase) inh | CPI-360 | EZH1 |
| (R)-Rolipram | PDE4 | GSK503 | EZH2 |
| Lenalidomide | TNFa | CPI-169 | EZH2 |
| GSK429286A | ROCKI | EPZ015666 | PRMT5 |
| 1-Azakenpaullone | GSK3b | GSK126 | EZH2 |
| Sorafenib | Raf | El1 | EZH2 |
| Dinaciclib | CDKs | UNC0631 | histone methyltransferase G9a |
| GSK1059615 | PI3Ka | MI-2 | menin-MLL interaction |
| SR-3677 | ROCK | PFI-2 | SETD7 |
| PP1 | Src | 3-Deazaneplanocin A | S-adenosylhomocysteine hydrolase |
| Dexamethasone | Glucocorticoid Receptors | UNC1999 | EZH2 and EZH1 |
| TTP 22 | CK2 | SGC0946 | DOT1L |
| LH846 | CK1d | EPZ004777 | DOT1L |
| BIBR 1532 | Telomerase | I-BET151 | BRD2, BRD3 and BRD4 |
| Decitabine | Epi | PFI-1 | BRD4 |
| EX 527 | Epi | I-BET-762 | BET proteins |
| OAC1 | Oct4 act | RVX-208 | BD2 |
| Rapamycin | mTOR Ant, BMP/Smad mod | OF-1 | BRPF1B and BRPF2 bromodomain |
| TSU-68 | PDGFR, FGFR, VEGFR | GSK1324726A | BRD2, BRD3, and BRD4 |
| LDN193189 (Hydrochloride) | BMP | PFI-3 | SMARCA2, SMARCA4 and PB1(5) |
| GSK126 | EZH2 | SGC-CBP30 | CREBBP/EP300 |
| PR-619 (DUBi) | Deubiquitinase DUB | Bromosporine | BRD2, BRD4, BRD9 and CECR2 |
| Reversine | MEK | UNC1215 | MBT (malignant brain tumor) |
| Pifithrin-a | p53 inh | OTX015 | BRD2, BRD3, and BRD4 |
| OTX-015 | Epi | CPI-203 | BET bromodomain inhibitor |
| Rosiglitasone (BRL 49653) | PPAR | EX527 | SIRT1 |
| Disulfiram | Aldehyde dehydrogenase | Nicotinamide | active component of coenzymes NAD and NADP |
| TWS119 | GSK3b | SRT2104 | SIRT1 |
| IOX1 | Epi | Roxadustat | HIF α prolyl hydroxylase inhibitor |
| Vorinostat | Epi | 2-Methoxyestradiol | HIF-1α |
| Gatifloxacin | DNA Gyrase | IOX2 | IHIF-1α prolyl hydroxylase-2 (PHD2) |
| 3-Deazaneplanocin | EZH2 | BAY 87-2243 | HIF-1 |
| GSK343 | Epi | Olaparib | PARP1/2 |
| KY02111 | Wnt | \veliparib | PARP1 and PARP2 |
| StemRegenin 1 | AhR | Rucaparib | PARP |
| JANEX-1 | JAK3 | Talazoparib | PARP |
| GNE-617 | NAMPT | G007-LK | TNKS1/2 |
| A-769662 | AMPK | AG-14361 | PARP1 |
| Sodium butyrate | Epi | INO-1001 | PARP |
| Pifithrin-u | p53/Bcl PPI | A-966492 | PARP1 and PARP2 |
| AZ191 | Dyrk1B | PJ34 | PARP |
| Bortezomib | Proteasome | Panobinostat | HDAC |
| Y-27632 (dihydrochloride) | ROCK | Mocetinostat | HDAC1 |
| IBMX | PDEs | CUDC-101 | HDAC, EGFR and HER2 |
| SB-505124 | Alk4, 5, 7 | Quisinostat | HDAC1, HDACs 2, 4, 10, and 11 |
| IWP-2 | Wnt | Tubastatin | HDAC6 |
| Purmorphamine | Hh | PCI-34051 | HDAC8 i |
| EPZ005687 | Epi | RGFP966 | HDAC6 |
| IWP-L6 | Wnt | AR-42 | HDAC |
| KU-0063794 | mTOR | Rocilinostat | HDAC6 |
| Niclosamide | Wnt | BRD73954 | HDAC |
| Tranylcypromine | Epi | CAY10603 | HDAC6 |
| CYCLOHEXAMIDE | Epi | LMK-235 | HDAC4 and HDAC5 |
| PD0325901 | MEK | Nexturastat A | HDAC6 |

TABLE 4-continued

Representative biologically diverse chemical series tested

| BioDiverse Set COMPOUND | TARGET | Epigenetics Set COMPOUND | TARGET |
|---|---|---|---|
| BIX-01294 | Epi | TMP269 | THDAC4, HDAC5, HDAC7 and HDAC9 |
| GSK1838705A | AlK5/IGF1R | HPOB | HDAC6 |
| Etoposide | TopoII | Ruxolitinib | JAK1/2 |
| GSK1324726A | Epi | Tofacitinib | JAK3 |
| XAV-939 | Wnt | AZD1480 | JAK2 |
| Ell | Epi | AT9283 | JAK2/3 |
| AMD 3465 (hexahydrobromide) | CXCR4 | Tofacitinib | JAK3 |
| CX-4945 | CK2 | Gandotinib | JAK2 |
| Taxifolin | EGFR, PI3K | NVP-BSK805 | JAK2 |
| Noscapine | Autophagy Ag | Cerdulatinib | JAK1/JAK2/JAK3/TYK2 and Syk |
| Cardionogen | Wnt | CEP-33779 | JAK2 |
| SB203580 | MAPK | Alisertib | Aurora A |
| LRRK-IN-1 | LRRK2 | VX-680 | Aurora A |
| GSK525768A | Epi | Barasertib | Aurora B |
| RG108 | Epi | Danusertib | Aurora A/B/C |
| BMS-378806 | gp120-CD4 | SNS-314 | Aurora A, Aurora B and Aurora C |
| MEK162 | MEK | PF-0381473 | Aurora A/B |
| UNC199 | EZH1/2 | MK-5108 | Aurora A |
| Kartogenin | Pheno | SGI-1776 | Pim1 |
| FK866 | NMPRT | STF-118804 | NAMPT |
| Vismodegib | Hh | FK866 | nicotinamide phosphoribosyltransferase (NMPRTase) |
| Cilengitide | Integrin aVb3 | Tipifarnib | farnesyltransferase (FTase) |
| IQ1S | JNK3 | LB42708 | farnesyltransferase (FTase) |

Example 6: Compound Screening and Myotube Formation Assay

For screening, frozen satellite-like cells, prepared as described in Example 1, were thawed in a water bath at 37° C., resuspended in 3 mL of warm Myoblast Medium (Genea Biocells) and centrifuged at 400×g for 4 min. The supernatant was removed and the cell pellet was resuspended in 1 mL of medium for cell count. Cells were seeded at a density of 5,000 cells/cm$^2$ in collagen I-coated plastic flasks (Biocoat, BD Bioscience) and incubated at 5% $CO_2$, 37° C. Every other day the culture medium was exchanged until cells reached a confluency of 80%, then cells were trypsinized, counted and seeded in collagen-coated 96-well plate (Biocoat) at density of 30,000 cells/cm$^2$ in Myoblast Medium using an automated liquid handling system (Fluent, Tecan Trading AG, Switzerland). Cells were incubated at 5% $CO_2$, 37° C. and the medium was changed every other day until cells reached a confluence of 80%. The medium was exchanged for Myotube Medium (Genea Biocells) containing the test compounds. No further media changes were performed. In general, 3 to 6 concentrations were tested ranging from 3 µM to 1 nM; one plate per dilution was used. Media and DMSO control wells were placed randomly. No media changes were performed at this stage. After five days of myotube differentiation in the presence of compounds, cells were fixed with 10% formalin (Sigma) for 15 minutes at room temperature and washed once with phosphate-buffered saline (PBS). Next, cells were stained with an antibody specific for myosin heavy chain (Developmental Studies of Hybridoma Bank, University of Iowa, Iowa City; anti mouse A4.1519; dilution 1:1000) in PBS solution containing 5% bovine serum albumin (BSA, Sigma) and 0.3% Triton-X (Sigma) and incubated for 1 hour at room temperature. The cells were washed once with PBS and then incubated for 1 hour with a second antibody, Alexa Fluor 488-conjugated goat anti-mouse IgG (Invitrogen, 1:1000), and counterstained for nuclei with Hoechst 33342 (Molecular probes 1:5000) in a PBS solution containing 5% BSA and 0.3% Triton-X. Cells were washed with PBS prior microscopic analysis. Cells were imaged using an IN Cell Analyzer 6000 (GE-Healthcare) high content analysis system. Developer Toolbox v1.9.3 was utilized for image analysis to determine the number of nuclei, and the number of nuclei within MHC-positive myotubes. To evaluate the effect of compounds in either decrease or increase these measures untreated controls were set as the baseline.

Example 7: Improved Myotube Formation Via Cell Cycle Inhibition

Myoblasts were prepared or frozen myoblasts were thawed as described in Example 4. Once cultures reached confluency the medium was changed to Myotube Medium supplemented with 0.2, 0.5 or 1 µM CHIR-124 (Chk1 inhibitor). The cultures were left in an incubator at 37° C. and 5% $CO_2$ for 5 days. During that period myoblasts differentiated to myotubes. Cells were fixed with 10% formalin (Sigma) for 15 minutes at room temperature and washed once with phosphate-buffered saline (PBS). Next, cells were stained for with antibodies specific for myosin heavy chain (Developmental Studies of Hybridoma Bank, University of Iowa, Iowa City; anti mouse A4.1519; dilution 1:1000) and MyoG (Santa Cruz, anti-rabbit; dilution 1:500) in PBS solution containing 5% bovine serum albumin (BSA, Sigma) and 0.3% Triton-X (Sigma) and incubated for 1 hour at room temperature. The cells were washed once with PBS and then incubated for 1 hour with a second antibody, Alexa Fluor 488-conjugated goat anti-mouse IgG and Alexa Fluor 647-conjugated anti-rabbit (both Invitrogen, 1:1000), and counterstained for nuclei with Hoechst 33342 (Molecular probes 1:5000) in a PBS solution containing 5% BSA and 0.3% Triton-X. Cells were washed with PBS prior to microscopic analysis. Cells were imaged using an IN Cell Analyzer 6000 (GE-Healthcare) high content analysis system. Developer Toolbox v1.9.3 was utilized for image analysis to determine the number of nuclei, MyoG-positive nuclei, nuclei within MHC-positive myotubes, nuclei per myotube and average myotube diameter. Visually, many of the cells exposed to 0.2 µM, 0.5 µM, or 1 µM CHIR-124 formed thick, large myotubes that are morphologically similar to myotubes formed by human primary myoblasts from biopsy material (FIG. 10A). At the 1 µM concentration, the CHIR-124 exhibited some toxicity and overall fewer myotubes were observed. Images were quantitatively analyzed and revealed that myotubes generated in the presence of 0.2 or 0.5 µM CHIR-124 showed >80% larger average diameters (FIG. 10B, upper panel), and more than double the average number of nuclei per myotube from 2 to about 4 compared to myotubes formed in the absence of CHIR-124. In addition, many myotubes exposed to CHIR-124 contained more than 30 nuclei (FIG. 10C, upper panel) whereas untreated controls contained few multi-nucleated cells exceeding 10-12 nuclei per myotube. Increases were also seen in myotube area (FIG. 10C, lower panel), the number of cells with larger myotube area (FIG. 10D, upper panel), the mean area of myotubes (FIG. 10D, lower panel), and the number of cells with more than one nucleus (FIG. 10B, lower panel).

Example 8: Modulation of Myotube Formation Via MEK/Raf/mTOR Inhibition

Myoblasts were prepared or frozen myoblasts were thawed as described in Example 4. Once cultures reached confluency the medium was changed to Myotube Medium supplemented with 0.1, 0.3 or 1 µM rapamycin (mTOR inhibitor) or MEK162 (binimetinib, MEK inhibitor) or sorafenib (Raf inhibitor). The cultures were left in an incubator at 37° C. and 5% $CO_2$ for 5 days. During that period myoblasts differentiated to myotubes. Cells were fixed with 10% formalin (Sigma) for 15 minutes at room temperature and washed once with phosphate-buffered saline (PBS). Next, cells were stained for with antibodies specific for myosin heavy chain (Developmental Studies of Hybridoma Bank, University of Iowa, Iowa City; anti mouse A4.1519; dilution 1:1000) and MyoG (Santa Cruz, anti-rabbit; dilution 1:500) in PBS solution containing 5% bovine serum albumin (BSA, Sigma) and 0.3% Triton-X (Sigma) and incubated for 1 hour at room temperature. The cells were washed once with PBS and then incubated for 1 hour with a second antibody, Alexa Fluor 488-conjugated goat anti-mouse IgG and Alexa Fluor 647-conjugated anti-rabbit (both Invitrogen, 1:1000), and counterstained for nuclei with Hoechst 33342 (Molecular probes 1:5000) in a PBS solution containing 5% BSA and 0.3% Triton-X. Cells were washed with PBS prior to microscopic analysis. Cells were imaged using an IN Cell Analyzer 6000 (GE-Healthcare) high content analysis system. Developer Toolbox v1.9.3 was utilized for image analysis to determine the number of nuclei, MyoG-positive nuclei, nuclei within MHC-positive myotubes, nuclei per myotube and average myotube diameter. Visually, cells exposed to the inhibitors formed more and longer and thicker myotubes than control cultures (FIGS. 11-13).

Example 9: Modulation of Myotube Formation Via G-Protein Coupled Receptor Lipid Signaling Myoblasts were prepared or frozen myoblasts were thawed as described in Example 4. Once cultures reached confluency the medium was changed to Myotube Medium supplemented with 0.1, 0.3 or 1 µM GSK1292263 (GPR119 agonist) or TC-G 1006 (S1P1 agonist). The cultures were left in an incubator at 37° C. and 5% $CO_2$ for 5 days. During that period myoblasts differentiated to myotubes. Cells were fixed with 10% formalin (Sigma) for 15 minutes at room temperature and washed once with phosphate-buffered saline (PBS). Next, cells were stained for with antibodies specific for myosin heavy chain (Developmental Studies of Hybridoma Bank, University of Iowa, Iowa City; anti mouse A4.1519; dilution 1:1000) and MyoG (Santa Cruz, anti-rabbit; dilution 1:500) in PBS solution containing 5% bovine serum albumin (BSA, Sigma) and 0.3% Triton-X (Sigma) and incubated for 1 hour at room temperature. The cells were washed once with PBS and then incubated for 1 hour with a second antibody, Alexa Fluor 488-conjugated goat anti-mouse IgG and Alexa Fluor 647-conjugated anti-rabbit (both Invitrogen, 1:1000), and counterstained for nuclei with Hoechst 33342 (Molecular probes 1:5000) in a PBS solution containing 5% BSA and 0.3% Triton-X. Cells were washed with PBS prior to microscopic analysis. Cells were imaged using an IN Cell Analyzer 6000 (GE-Healthcare) high content analysis system. Developer Toolbox v1.9.3 was utilized for image analysis to determine the number of nuclei, MyoG-positive nuclei, nuclei within MHC-positive myotubes, nuclei per myotube and average myotube diameter. Visually, cells exposed to the agonists formed longer and thicker myotubes than control cultures (FIGS. 14-15).

Example 10: Modulation of Myotube Formation by Modulating mAChR Signaling

Myoblasts were prepared or frozen myoblasts were thawed as described in Example 4. Once cultures reached confluency the medium was changed to the medium was changed to Myotube Medium supplemented with 0.1, 0.3 or 1 µM pilocarpine (mAChR agonist) or 0.2, 0.5 or 1 µM atropine (mAChR antagonist). The cultures were left in an incubator at 37° C. and 5% $CO_2$ for 5 days. During that period myoblasts differentiated to myotubes. Cells were fixed with 10% formalin (Sigma) for 15 minutes at room temperature and washed once with phosphate-buffered saline (PBS). Next, cells were stained for with antibodies specific for myosin heavy chain (Developmental Studies of Hybridoma Bank, University of Iowa, Iowa City; anti mouse A4.1519; dilution 1:1000) and MyoG (Santa Cruz, anti-rabbit; dilution 1:500) in PBS solution containing 5% bovine serum albumin (BSA, Sigma) and 0.3% Triton-X (Sigma) and incubated for 1 hr at room temperature. The cells were washed once with PBS and then incubated for 1 hour with a second antibody, Alexa Fluor 488-conjugated goat anti-mouse IgG and Alexa Fluor 647-conjugated anti-rabbit (both Invitrogen, 1:1000), and counterstained for nuclei with Hoechst 33342 (Molecular probes 1:5000) in a PBS solution containing 5% BSA and 0.3% Triton-X. Cells were washed with PBS prior microscopic analysis. Cells were imaged using an IN Cell Analyzer 6000 (GE-Healthcare) high content analysis system. Developer Toolbox v1.9.3 was utilized for image analysis to determine the number of nuclei, MyoG-positive nuclei, nuclei within MHC-positive myotubes, nuclei per myotube and average myotube diameter. Visually, cells exposed to the mAChR modulators formed longer and thicker myotubes than control cultures (FIGS. 16-17). Atropine at 1 µM was toxic and overall fewer myotubes were observed in cultures incubated with atropine.

Example 11: Modulation of Myotube Formation Via PARP Inhibition

Myoblasts were prepared or frozen myoblasts were thawed as described in Example 4. Once cultures reached confluency the medium was changed to Myotube Medium supplemented with 0.1, 0.3 or 1 µM Talazoparib (PARP inhibitor). The cultures were left in an incubator at 37° C. and 5% $CO_2$ for 5 days. During that period myoblasts differentiated to myotubes. Cells were fixed with 10% formalin (Sigma) for 15 minutes at room temperature and washed once with phosphate-buffered saline (PBS). Next, cells were stained for with antibodies specific for myosin heavy chain (Developmental Studies of Hybridoma Bank, University of Iowa, Iowa City; anti mouse A4.1519; dilution 1:1000) and MyoG (Santa Cruz, anti-rabbit; dilution 1:500) in PBS solution containing 5% bovine serum albumin (BSA, Sigma) and 0.3% Triton-X (Sigma) and incubated for 1 hour at room temperature. The cells were washed once with PBS and then incubated for 1 hour with a second antibody, Alexa Fluor 488-conjugated goat anti-mouse IgG and Alexa Fluor 647-conjugated anti-rabbit (both Invitrogen, 1:1000), and counterstained for nuclei with Hoechst 33342 (Molecular probes 1:5000) in a PBS solution containing 5% BSA and 0.3% Triton-X. Cells were washed with PBS prior microscopic analysis. Cells were imaged using an IN Cell Analyzer 6000 (GE-Healthcare) high content analysis system. Developer Toolbox v1.9.3 was utilized for image analysis to determine the number of nuclei, MyoG-positive nuclei, nuclei within MHC-positive myotubes, nuclei per myotube and average myotube diameter. Visually, cells exposed to the Talazoparib formed more and longer myotubes than control cultures (FIG. 18).

Example 12: Compound Screening by Targeted Biomarker RNASeq

Cells are set up for the screening of compounds according to Example 4. Cells are cultured in collagen I-coated 96-well plates. At the end of the culture period, total RNA is extracted from each well. The concentration and integrity of each RNA sample is confirmed by measuring the absorbance at 260 nm and 280 nm and capillary electrophoresis (Bioanalyzer, Agilent Technologies). RNA samples are then analyzed by targeted RNASeq using the TruSeq system (Illumina) for a custom panel of genes (Table 5). Results are normalized to housekeeping genes (Table 5) and relative gene expression levels and statistical significance are calculated. Hits are defined as compounds that do not alter the expression pattern of muscle and myogenesis-related genes.

TABLE 5

Exemplary panel of myogenic and muscular dystrophy-associated biomarker genes that may be selected for screening by targeted RNASeq

| | | |
|---|---|---|
| TBX6 | CHRNA1 | CAPN2 |
| Mesogenine | CHRNA3 | CASP3 |
| Pax3 | CDC42 | FBXO32 |
| Pax7 | CDCA8 | FOXO3 |
| Myf5 | CDKN1B | NOS2 |
| MyoD | CDKN2B | PPARGC1A |
| MyoG | CDK5R1 | PPARGC1B |
| MRF4 | FOXM1 | RPS6KB1 |
| MYH8 | CCND1 | TRIM63 |
| ACTA2 | NOTCH1 | AKT1 |
| ARHGEF6 | Dll1 | AKT2 |
| PFN2 | WNT2 | MAPK8 (JNK1) |
| LBP | WNT5A | MMP9 |
| NFIX | FRZB | NFKB1 |
| ERBB3 | TGFB | UTRN |
| MSTN | BMP4 | Pax 6 |
| BDNF | Col2A1 | nestin |
| BCL2 | Col19A1 | Alpha fetoprotein |

TABLE 5-continued

Exemplary panel of myogenic and muscular dystrophy-associated biomarker genes that may be selected for screening by targeted RNASeq

| | | |
|---|---|---|
| CAV1 | Col1A1 | Sox 17 |
| MEF2c | Col5A2 | Nanog |
| IGF1 | Col6A1 | Oct-3/4 |
| TGM2 | Col6A2 | DMPK |
| NTM | Col6A3 | MBNL-1 |
| CILP | Col1A1 | MBNL-2 |
| PODXL | Col14A1 | LAP2 |
| AGTPBP1 | Col15A1 | Lamin B receptor |
| MBD3L2 | FBN1 | LMNA |
| TRIM43 | CAMK2G | SYNE2 gene |
| ZSCAN4 | CAPN3 | EDMD |
| COL2A1 | CAV3 | ACTA1 |
| ZNF296 | DAG1 | NEB |
| MEG3 | DMD | TPM2 |
| SPRYD5 | DYSF | TPM3 |
| EGFL6 | LMNA | TNNT1 |
| GSTT1 | MAPK1 (ERK2) | KBTBD13 |
| PRAMEF2 | SGCA | CFL2 |
| KHDC1L | MYH1 | KLHL40 |
| RYR1 | TNNC1 | KLHL41 |
| RYR3 | SLC2A4 (Glut4) | LAMA2 |
| SMCHD1 | GLUT1 | GLUT4 |
| | housekeeping genes: | |
| GUSB | REEP5 | C1orf43 |
| VCP | GPI | |

Example 13: Effect of Cell-Cycle Inhibitor on Differentiation of Disease-Specific Cell Lines Myoblasts prepared via the method of Example 4 from two non-affected hESC cell lines (Genea002 and Genes019) and six verified genetic disease-affected cell lines (Genea020, Genea066, Gen103, Gen158, Gen049 and Gen159, described in Table 6 below) were thawed in Genea Biocells Myoblast Medium in 96-well microtiter plates at 3.0×104 cells/cm2 and incubated at 10% CO2, 37° C. Genea020 was derived from an embryo affected with Huntington's disease (48 CAG repeat expansion in the Huntingtin gene). Genea066 was derived from an embryo affected with Myotonic Dystrophy type II. Genea103 was derived from an embryo affected with Spinal Muscular Atrophy. Genea158 was derived from an embryo affected with Myotonic Dystrophy type I. Genea049 was derived from an embryo affected with FSH Muscular Dystrophy. Genea159 was derived from an embryo affected with Duchenne muscular dystrophy. All hESC cell lines were derived according to approved ethical protocols from donated embryos. Once cells (myoblasts) were confluent (approximately on day 3) media was changed for Genea Biocells Myotube Medium, either alone or with 0.5 µM CHIR-124 (CHIR). Cell cultures were fixed three days post switching to Myotube Medium and stained with an antibody specific for myosin heavy chain (MHC, A4.1025, DSHB, 1:1,000) and co-stained with Hoechst for nuclei visualization. Cultures were imaged with a 10× objective using an IN Cell Analyzer 6000 (GE Healthcare) high-content analyzer. Images were analyzed with IN Cell Developer Toolbox software (GE Healthcare). All cell lines showed improved myotube formation in the presence of CHIR-124 as measured by MHC staining area normalized to cell number (nuclei), which increases in the condition with Myotube Medium+CHIR124 (SII/SIII+ CHIR) relative to the condition with just Myotube Medium (SII/SIII) (see FIG. 19). The ratio between area of MHC and nuclei (um2) was calculated by measuring the area per field divided by the number of nuclei within that field.

The ability of CHIR-124 to affect myotube formation in both disease-affected (Genea020, Genea066, Gen103, Gen158, Gen049 and Gen159) and disease-unaffected cell lines (Genea002 and Genes019) suggests the usefulness of Chk1 inhibition in augmenting myotube formation in muscles of patients affected with disorder such as Huntington's Disease, Myotonic Dystrophy type II, Spinal Muscular Atrophy, Myotonic Dystrophy type 1, FSH Muscular Dystrophy, and Duchenne Muscular Dystrophy.

TABLE 6

Disease-affected and non-affected hESC lines used in this study

| Cell line | Disease status/Mutation | Gene/Locus Affected |
|---|---|---|
| Genea002 | Unaffected | N/A |
| Genea019 | Unaffected | N/A |
| Genea015 | Unaffected | N/A |
| Genea020 | Huntington's Disease | HTT (Huntingtin) 48 CAG repeats |
| Genea066 | Myotonic Dystrophy type II | ZNF9 |
| Genea103 | Spinal Muscular Atrophy | SMN1 |
| Genea158 | Myotonic Dystrophy type 1 | DMPK |
| Genea049 | FSH Muscular Dystrophy | D4Z4 repeat deletion at 4q35 |
| Genea159 | Duchenne muscular dystrophy | Deletion of DMD at Xp21 |

Example 14: Myosin Heavy Chain Analysis in Cells Treated with CHIR-124

Genea015 (a disease-unaffected hESC cell line) myoblasts prepared by the method of Example 4 were thawed and seeded at 30,000 cells/cm$^2$ in Genea Biocells Myoblast Medium and incubated at 37° C., 5% CO$_2$ until confluent (approximately 2 days). Then media was changed for Genea Biocells Myotube Medium either alone or with 0.5 μM CHIR-124. Cell lysates for protein analysis were collected 5 days after treatment with CHIR-124 and quantified by BCA assay (ThermoFisher). Western blotting (Wes, Protein Simple) was performed to analyze the expression of myosin heavy chains (MHC) that are expressed during development and maturation of myotubes (total MHC, or total myosin heavy chain; eMHC, or embryonic myosin heavy chain; fMHC, or foetal myosin heavy chain; pMHC, or perinatal myosin heavy chain; and fast MHC, or fast myosin heavy chain, the most mature MHC found in myotubes). MHC expression was normalized to Vinculin for quantification. A plot of the different MHC forms in the presence of Genea Biocells Myotube Medium (SIII, see FIG. 20) vs. Genea Biocells Myotube Medium plus CHIR-124 (SIII+CHIR, see FIG. 20) demonstrate that the presence of CHIR-124 increases expression of total MHC over the 5 day treatment period. This increase in total MHC involves the increased expression of the most mature forms of MHC (pMHC and fast MHC, which both show increases in expression upon the addition of CHIR-124, see FIG. 20). In total, the data suggests that CHIR-124 accelerates myotube development by driving expression of more mature MHC isoforms.

Example 15: Treatment of Duchenne Muscular Dystrophy (DMD) with a Checkpoint Inhibitor A 5-year old boy diagnosed with Duchenne Muscular Dystrophy (DMD) is seen in a clinic for weakness in his calves and thighs. To treat the muscle weakness, the patient is administered 100 mg once daily of CHIR-124 or 50-75 mg twice daily of CHIR-124 for two months, at which point the symptoms of muscle weakness improve.

Example 16: Treatment of Duchenne Muscular Dystrophy (DMD) with a Checkpoint Inhibitor Combined with a Cell Therapy A 5-year old boy diagnosed with Duchenne Muscular Dystrophy (DMD) is seen in a clinic for weakness in his calves and thighs. To treat the muscle weakness, the patient is administered 100 mg once daily of CHIR-124 or 50-75 mg twice daily of CHIR-124 for two months. At the initial appointment, skin fibroblasts are obtained from the patient. The fibroblasts are subsequently used to produce induced pluripotent stem cells (iPSCs), which are then genetically modified to remove a mutation associated with DMD. The iPSCs are then differentiated into satellite cells in vitro; and the satellite cells, in turn, are differentiated into myoblasts in vitro. The differentiated myoblasts are then administered in 5 M doses to the patient's thighs and calves once a week during the two month period. The patient experiences improved muscle tone as a result of the treatment.

What is claimed is:

1. A method of generating mature myotubes, the method comprising:
   a. providing myoblasts, wherein the myoblasts are derived from a human;
   b. culturing the myoblasts in vitro in a culture comprising a medium comprising CHIR-124, thereby producing mature myotubes exhibiting two or more of the following features: (i) greater than 15 nuclei per myotube; (ii) a length greater than 0.5 mm; (iii) a diameter larger than 6 μm; and (iv) a myotube area greater than 3,000 μm$^2$.

2. The method of claim 1, further comprising incubating the myoblasts in the medium comprising CHIR-124 for at least 12 hours.

3. The method of claim 1, further comprising detecting the mature myotubes in the culture.

4. The method of claim 1, wherein the mature myotubes exhibit greater than 30 nuclei per cell.

5. The method of claim 1, wherein the mature myotubes exhibit a myotube area greater than 4,000 μm$^2$.

6. The method of claim 1, wherein the mature myotubes exhibit a myotube area greater than 5,000 μm$^2$.

7. The method of claim 1, wherein the culture comprises myotubes with a mean myotube area greater than 1,000 μm$^2$.

8. The method of claim 1, wherein the culture comprises myotubes with a mean myotube area greater than 2,000 μm$^2$.

9. The method of claim 1, wherein the mature myotubes exhibit a diameter greater than 6 μm.

10. The method of claim 1, wherein the mature myotubes exhibit a diameter greater than 10 μm.

11. The method of claim 1, wherein the mature myotubes exhibit a diameter larger than 12 μm.

12. The method of claim 1, wherein the mature myotubes exhibiting the two or more features make up at least 50% of a culture in the absence of purification or selection for mature myotubes.

13. The method of claim 1, wherein the mature myotubes exhibiting the two or more features make up at least 50% of a culture in the absence of purification or selection for mature myotubes.

14. The method of claim 1, wherein the mature myotubes exhibiting the two or more features make up at least 60% of the culture in the absence of purification or selection for mature myotubes and exhibit a diameter greater than 10 µm.

15. The method of claim 1, wherein the myoblasts are primary myoblasts.

16. The method of claim 1, wherein the myoblasts are generated by differentiating satellite cells in vitro.

17. The method of claim 1, wherein the mature myotubes are mature myotube-like cells.

18. The method of claim 16, wherein the satellite cells are generated by differentiating pluripotent stem cells in vitro.

19. The method of claim 18, further comprising contacting satellite cells with a compound to generate the myoblasts.

20. The method of claim 19, further comprising contacting pluripotent stem cells with one or more compounds to generate the satellite cells.

21. The method of claim 20, wherein the mature myotubes are generated less than 30 days from the contacting the pluripotent stem cells with the one or more compounds to generate the satellite cells.

22. The method of claim 20, wherein the mature myotubes are generated within 25 days from the contacting the pluripotent stem cells with the one or more compounds to generate the satellite cells.

23. The method of claim 20, wherein the mature myotubes are generated less than 30 days from the contacting the pluripotent stem cells with the one or more compounds to generate the satellite cells and wherein the mature myotubes are generated at a rate of at least five mature myotubes per pluripotent stem cell.

24. The method of claim 20, wherein the mature myotubes are generated less than 30 days from the contacting the pluripotent stem cells with the one or more compounds to generate the satellite cells and wherein the mature myotubes are generated at a rate of at least 50 mature myotubes per pluripotent stem cell.

* * * * *